United States Patent
Heaven et al.

(10) Patent No.: US 9,826,970 B2
(45) Date of Patent: Nov. 28, 2017

(54) SYSTEM AND METHOD FOR SECURING TISSUE TO BONE

(75) Inventors: Malcolm Heaven, Dana Point, CA (US); Michael Ko, Mission Viejo, CA (US); John P. Greelis, Carlsbad, CA (US); Mikxay Sirivong, Escondido, CA (US)

(73) Assignee: CONMED CORPORATION, Utica, NY (US)

( * ) Notice: Subject to any disclaimer, the term of this patent is extended or adjusted under 35 U.S.C. 154(b) by 831 days.

(21) Appl. No.: 12/903,187

(22) Filed: Oct. 12, 2010

(65) Prior Publication Data

US 2011/0112550 A1    May 12, 2011

Related U.S. Application Data

(60) Provisional application No. 61/251,220, filed on Oct. 13, 2009, provisional application No. 61/370,791, filed on Aug. 4, 2010.

(51) Int. Cl.
| | | |
|---|---|---|
| *A61B 17/10* | (2006.01) | |
| *A61B 17/08* | (2006.01) | |
| *A61B 17/04* | (2006.01) | |

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC ........ A61B 17/0401; A61B 2017/0409; A61B 2017/0414; A61B 2017/0424; A61B 2017/0438; A61B 2017/0412
(Continued)

(56) References Cited

U.S. PATENT DOCUMENTS

| 4,590,928 A | 5/1986 | Hunt et al. |
| 4,738,255 A | 4/1988 | Goble et al. |

(Continued)

FOREIGN PATENT DOCUMENTS

| EP | 0 241 240 A2 | 10/1987 |
| EP | 0 270 704 A1 | 6/1988 |

(Continued)

OTHER PUBLICATIONS

Boileau et al., Arthroscopic Biceps Tenodesis: A New Technique Using Bioabsorbable Interference Screw Fixation, Arthroscopy: The Journal of Arthroscopic and Related Surgery, vol. 18, No. 9 Nov.-Dec. 2002, pp. 1002-1012.*

(Continued)

*Primary Examiner* — Jing Ou
(74) *Attorney, Agent, or Firm* — Frederick J M Price; Bond, Schoeneck & King, PLLC

(57) ABSTRACT

Disclosed herein are methods and devices for securing soft tissue to a rigid material such as bone. A tissue capture anchor is described that comprises an anchor body and a spreader such that tissue may be captured or compressed between outside surfaces on the anchor and spreader and inside surfaces of a bone hole to secure the tissue within the hole. A bone anchor is described that comprises an anchor body with expandable tines and a spreader that expands the tines into bone. The spreader captures tissue via a suture loop at the distal end of the bone anchor. Also described is an inserter that can be used to insert the anchor into bone and move the spreader within the anchor to expand the anchor and capture the tissue between the anchor and the bone. Methods are described that allow use of single bone anchor to secure tissue to bone or also to use more than one bone anchor to provide multiple lengths of suture material to compress a large area of soft tissue against bone.

15 Claims, 50 Drawing Sheets

(52) U.S. Cl.
CPC ............... *A61B 2017/0414* (2013.01); *A61B 2017/0424* (2013.01); *A61B 2017/0438* (2013.01)

(58) Field of Classification Search
USPC ........... 606/232, 300–312; 623/11.11, 11.16, 623/16.11, 13.14, 13.15
See application file for complete search history.

(56) References Cited

U.S. PATENT DOCUMENTS

| | | |
|---|---|---|
| 4,851,005 A | 7/1989 | Hunt et al. |
| 4,870,957 A | 10/1989 | Goble et al. |
| 4,960,420 A | 10/1990 | Goble et al. |
| 4,988,351 A | 1/1991 | Paulos et al. |
| 5,037,422 A | 8/1991 | Hayhurst et al. |
| 5,161,916 A | 11/1992 | White et al. |
| 5,167,665 A | 12/1992 | McKinney |
| 5,176,682 A | 1/1993 | Chow |
| 5,192,303 A | 3/1993 | Gatturna et al. |
| 5,197,983 A | 3/1993 | Berman et al. |
| 5,209,756 A | 5/1993 | Seedhom et al. |
| 5,222,963 A | 6/1993 | Brinkerhoff et al. |
| 5,224,946 A | 7/1993 | Hayhurst et al. |
| 5,246,443 A | 9/1993 | Mai |
| 5,268,001 A | 12/1993 | Nicholson et al. |
| 5,326,205 A | 7/1994 | Anspach et al. |
| 5,336,240 A | 8/1994 | Metzler et al. |
| 5,354,298 A | 10/1994 | Lee et al. |
| 5,372,599 A | 12/1994 | Martins |
| 5,380,334 A | 1/1995 | Torrie et al. |
| 5,397,356 A | 3/1995 | Goble et al. |
| 5,417,712 A | 5/1995 | Whittaker et al. |
| 5,472,452 A | 12/1995 | Trott |
| 5,480,403 A | 1/1996 | Lee et al. |
| 5,486,197 A | 1/1996 | Le et al. |
| 5,500,001 A | 3/1996 | Trott |
| 5,501,683 A | 3/1996 | Trott |
| 5,501,695 A | 3/1996 | Anspach et al. |
| 5,505,735 A | 4/1996 | Li |
| 5,522,844 A | 6/1996 | Johnson |
| 5,522,845 A | 6/1996 | Wenstrom |
| 5,522,846 A | 6/1996 | Bonutti |
| 5,545,180 A | 8/1996 | Le et al. |
| 5,554,171 A | 9/1996 | Gatturna et al. |
| 5,569,306 A | 10/1996 | Thal |
| 5,601,557 A | 2/1997 | Hayhurst |
| 5,618,314 A | 4/1997 | Harwin et al. |
| 5,628,751 A | 5/1997 | Sander et al. |
| 5,632,748 A | 5/1997 | Beck et al. |
| 5,643,274 A | 7/1997 | Sander et al. |
| 5,643,321 A | 7/1997 | McDevitt |
| 5,645,589 A | 7/1997 | Li |
| 5,649,963 A | 7/1997 | McDevitt |
| 5,702,215 A | 12/1997 | Li |
| 5,707,395 A | 1/1998 | Li |
| 5,713,903 A | 2/1998 | Sander et al. |
| 5,718,717 A | 2/1998 | Bonutti |
| 5,720,753 A | 2/1998 | Sander et al. |
| 5,725,557 A | 3/1998 | Gatturna et al. |
| 5,733,306 A | 3/1998 | Bonutti |
| 5,741,282 A | 4/1998 | Anspach et al. |
| 5,749,899 A | 5/1998 | Bardin |
| 5,782,865 A | 7/1998 | Grotz |
| 5,797,963 A | 8/1998 | McDevitt |
| 5,814,071 A | 9/1998 | McDevitt et al. |
| 5,814,072 A | 9/1998 | Bonutti |
| 5,849,004 A | 12/1998 | Bramlet |
| 5,891,168 A | 4/1999 | Thal |
| RE36,289 E | 8/1999 | Le et al. |
| 5,948,000 A | 9/1999 | Larsen et al. |
| 5,948,002 A | 9/1999 | Bonutti |
| 5,957,953 A | 9/1999 | DiPoto et al. |
| 5,964,764 A | 10/1999 | West et al. |
| 5,968,078 A | 10/1999 | Grotz |
| 5,980,558 A | 11/1999 | Wiley |
| 6,007,566 A | 12/1999 | Wenstrom |
| 6,022,373 A | 2/2000 | Li |
| 6,024,758 A | 2/2000 | Thal |
| 6,063,037 A | 5/2000 | Mittermeier et al. |
| 6,077,292 A | 6/2000 | Bonutti |
| 6,086,591 A | 7/2000 | Bojarski |
| 6,146,406 A | 11/2000 | Shluzas et al. |
| 6,149,669 A | 11/2000 | Li |
| 6,203,565 B1 | 3/2001 | Bonutti |
| 6,241,732 B1 | 6/2001 | Overaker et al. |
| 6,287,324 B1 | 9/2001 | Yarnitsky et al. |
| 6,312,448 B1 | 11/2001 | Bonutti |
| 6,319,269 B1 | 11/2001 | Li |
| 6,328,758 B1 | 12/2001 | Tornier et al. |
| 6,464,713 B2 | 10/2002 | Bonutti |
| RE37,963 E | 1/2003 | Thal |
| 6,540,770 B1 | 4/2003 | Tornier et al. |
| 6,544,281 B2 | 4/2003 | ElAttrache et al. |
| 6,547,800 B2 | 4/2003 | Foerster et al. |
| 6,554,862 B2 | 4/2003 | Hays et al. |
| 6,562,071 B2 | 5/2003 | Jarvinen |
| 6,582,453 B1 | 6/2003 | Tran et al. |
| 6,585,730 B1 | 7/2003 | Foerster |
| 6,616,694 B1 | 9/2003 | Hart |
| 6,632,224 B2 | 10/2003 | Cachia et al. |
| 6,635,073 B2 | 10/2003 | Bonutti |
| 6,641,597 B2 | 11/2003 | Burkhart et al. |
| 6,648,890 B2 | 11/2003 | Culbert et al. |
| 6,652,561 B1 | 11/2003 | Tran |
| 6,660,022 B1 | 12/2003 | Li et al. |
| 6,673,094 B1 | 1/2004 | McDevitt et al. |
| 6,689,135 B2 | 2/2004 | Enayati |
| 6,692,516 B2 | 2/2004 | West et al. |
| 6,770,076 B2 | 8/2004 | Foerster |
| 6,840,953 B2 | 1/2005 | Martinek |
| 6,846,313 B1 | 1/2005 | Rogers et al. |
| 6,887,271 B2 | 5/2005 | Justin et al. |
| 6,932,834 B2 | 8/2005 | Lizardi et al. |
| 7,008,451 B2 | 3/2006 | Justin et al. |
| 7,037,324 B2 | 5/2006 | Martinek |
| 7,144,413 B2 | 12/2006 | Wilford et al. |
| 7,226,469 B2 | 6/2007 | Benavitz et al. |
| 7,235,100 B2 | 6/2007 | Martinek |
| 7,309,346 B2 | 12/2007 | Martinek |
| 7,309,355 B2 | 12/2007 | Donnelly et al. |
| 7,329,281 B2 | 2/2008 | Hays et al. |
| 6,656,183 C1 | 6/2008 | Colleran et al. |
| 7,381,213 B2 | 6/2008 | Lizardi |
| 7,520,898 B2 | 4/2009 | Re et al. |
| 7,572,283 B1 | 8/2009 | Meridew |
| 7,588,586 B2 | 9/2009 | Whittaker |
| 7,611,521 B2 | 11/2009 | Lubbers et al. |
| D605,763 S | 12/2009 | Griffis, III et al. |
| 7,651,528 B2 | 1/2010 | Montgomery et al. |
| 7,699,893 B2 | 4/2010 | Donnelly et al. |
| 7,713,285 B1 | 5/2010 | Stone et al. |
| 7,828,802 B2 | 11/2010 | Levy et al. |
| 7,879,094 B2 | 2/2011 | Baird et al. |
| 7,967,861 B2 | 6/2011 | Montgomery et al. |
| 8,048,158 B2 | 11/2011 | Hays et al. |
| 5,417,691 C1 | 1/2012 | Hayhurst |
| 8,192,490 B2 | 6/2012 | Baird et al. |
| 8,221,479 B2 | 7/2012 | Glazer et al. |
| 8,317,863 B2 | 11/2012 | Cauldwell et al. |
| 8,435,294 B2 | 5/2013 | Montgomery et al. |
| 8,523,902 B2 | 9/2013 | Heaven et al. |
| 8,906,060 B2 | 12/2014 | Hart |
| 9,044,313 B2 | 6/2015 | Heaven et al. |
| 2001/0041916 A1 | 11/2001 | Bonutti |
| 2003/0004545 A1 | 1/2003 | Burkhart et al. |
| 2003/0100903 A1 | 5/2003 | Cooper |
| 2003/0130695 A1* | 7/2003 | McDevitt et al. ............ 606/232 |
| 2003/0153921 A1* | 8/2003 | Stewart ............. A61B 17/0401 606/232 |
| 2003/0191498 A1 | 10/2003 | Foerster et al. |
| 2003/0195564 A1 | 10/2003 | Tran et al. |
| 2003/0204204 A1 | 10/2003 | Bonutti |
| 2004/0010287 A1 | 1/2004 | Bonutti |

(56) References Cited

U.S. PATENT DOCUMENTS

| | | | |
|---|---|---|---|
| 2004/0093031 A1 | 5/2004 | Burkhart et al. | |
| 2004/0098053 A1 | 5/2004 | Tran | |
| 2004/0138683 A1 | 7/2004 | Shelton et al. | |
| 2004/0193217 A1 | 9/2004 | Lubbers et al. | |
| 2004/0230194 A1 | 11/2004 | Urbanski et al. | |
| 2004/0243179 A1 | 12/2004 | Foerster | |
| 2005/0055027 A1 | 3/2005 | Yeung et al. | |
| 2005/0149122 A1* | 7/2005 | McDevitt et al. | 606/232 |
| 2006/0095131 A1 | 5/2006 | Justin et al. | |
| 2006/0106422 A1 | 5/2006 | Del Rio et al. | |
| 2006/0116719 A1 | 6/2006 | Martinek | |
| 2006/0229617 A1 | 10/2006 | Meller et al. | |
| 2006/0235402 A1 | 10/2006 | Celli et al. | |
| 2006/0235413 A1* | 10/2006 | Denham et al. | 606/72 |
| 2006/0264950 A1 | 11/2006 | Nelson et al. | |
| 2006/0265064 A1 | 11/2006 | Re et al. | |
| 2006/0282081 A1 | 12/2006 | Fanton et al. | |
| 2007/0027477 A1* | 2/2007 | Chudik | 606/232 |
| 2007/0142835 A1 | 6/2007 | Green et al. | |
| 2007/0198018 A1 | 8/2007 | Biedermann et al. | |
| 2008/0033445 A1 | 2/2008 | Zucherman et al. | |
| 2008/0051795 A1 | 2/2008 | Whittaker | |
| 2008/0183220 A1 | 7/2008 | Glazer et al. | |
| 2008/0195221 A1 | 8/2008 | Howald et al. | |
| 2008/0221624 A1* | 9/2008 | Gooch | 606/302 |
| 2008/0262495 A1 | 10/2008 | Coati et al. | |
| 2009/0030516 A1 | 1/2009 | Imbert | |
| 2009/0043342 A1 | 2/2009 | Freedland | |
| 2009/0149884 A1 | 6/2009 | Sayder et al. | |
| 2009/0187216 A1 | 7/2009 | Schmieding et al. | |
| 2009/0248068 A1 | 10/2009 | Lombardo et al. | |
| 2010/0174369 A1 | 7/2010 | Wang et al. | |
| 2010/0185283 A1 | 7/2010 | Baird et al. | |
| 2010/0198258 A1 | 8/2010 | Heaven et al. | |
| 2010/0292732 A1 | 11/2010 | Hirotsuka et al. | |
| 2010/0326452 A1 | 12/2010 | Gall | |
| 2010/0331881 A1 | 12/2010 | Hart | |
| 2011/0067712 A1 | 3/2011 | Gall | |
| 2011/0112550 A1 | 5/2011 | Heaven et al. | |
| 2011/0184516 A1 | 7/2011 | Baird et al. | |
| 2012/0203339 A1 | 8/2012 | Heaven | |
| 2012/0239038 A1 | 9/2012 | Saravia et al. | |
| 2013/0338710 A1 | 12/2013 | Heaven | |
| 2014/0046369 A1 | 2/2014 | Heaven et al. | |

FOREIGN PATENT DOCUMENTS

| | | |
|---|---|---|
| EP | 0 574 707 A1 | 12/1993 |
| EP | 0 409 364 | 1/1994 |
| EP | 0 673 624 A2 | 9/1995 |
| EP | 0 504 915 | 1/1996 |
| EP | 1 348 380 A1 | 10/2003 |
| EP | 2 266 469 A1 | 12/2010 |
| FR | 2 671 717 | 7/1992 |
| WO | WO 95/15726 A1 | 6/1995 |
| WO | WO 97/07741 | 3/1997 |
| WO | WO 02/32345 A2 | 4/2002 |
| WO | WO 03/105700 | 12/2003 |
| WO | WO 2006/055823 | 5/2006 |
| WO | 2008/073588 | 6/2008 |
| WO | 2009/154781 | 12/2009 |
| WO | WO 2010/088561 | 8/2010 |
| WO | WO 2011/046982 | 4/2011 |
| WO | 2012/093961 | 7/2012 |
| WO | WO2012148693 A1 | 11/2012 |
| WO | WO2015059582 | 4/2015 |

OTHER PUBLICATIONS

Sherman et al., "The long-term followup of primary anterior cruciate ligament repair," The American Journal of Sports Medicine, vol. 19, No. 3, 243-255 (1991).

Whipple et al., "A Technique for Arthroscopic Anterior Cruciate Ligament Repair," Clinics in Sports Medicine, vol. 10, No. 3, 463-468 (1991).

Hecker et al., "Pull-out strength of suture anchors for rotator cuff and Bankart lesion repairs," The American Journal of Sports Medicine, vol. 21, No. 6, 874-879 (1993).

Green et al., "Arthroscopic Versus Open Bankart Procedures: A Comparison of Early Morbidity and Complications," The Journal of Arthroscopic and Related Surgery, vol. 9, No. 4, 371-374 (1993).

Shall et al., "Soft Tissue Reconstruction in the Shoulder," The American Journal of Sports Medicine, vol. 22, No. 5, 715-718 (1994).

Richards et al., "A Biomechanical Analysis of Two Biceps Tenodesis Fixation Techniques," Arthroscopy: The Journal of Arthroscopic and Related Surgery, vol. 21, No. 7, 2005: pp. 861-866.

"Executive Interview: Chris Fair, Chief Operations Officer; Ken Gall, Ph.D., Director & Chief Techical Officer, MedShape Solutions, Inc.," Orthopreneur, pp. 22-25, Jan./Feb. 2010.

Yakacki et al., "The Design and Pullout Strength of a Novel Shape-Memory PEEK Suture Anchor," 56$^{th}$ Annual Meeting of the Orthopaedic Research Society, Poster No. 1801 presented on approximately Mar. 1, 2010.

"Scope This Out: A Technical Pearls Newsletter for Arthroscopists," Spring 2010, pp. 1-8, vol. 12, No. 1, Arthrex, Inc.

International Search Report and Written Opinion dated Aug. 19, 2010 for International Application No. PCT/US2010/022661, filed Jan. 29, 2010.

International Search Report and Written Opinion dated Dec. 9, 2010, for International Patent Application No. PCT/US2010/052398, filed Oct. 12, 2010.

USS Sports Medicine presents POLYSORB 3mm Soft Tissue Anchor System, US Surgical Corp., Date of Publication unknown.

International Search Report and Written Opinion dated Jan. 18, 2013 for International Application No. PCT/US2012/058786, filed Oct. 4, 2012.

International Preliminary Report on Patentability dated Aug. 2, 2011 for International Application No. PCT/US2010/022661, filed Jan. 29, 2010.

International Search Report and Written Opinion dated Aug. 6, 2012, for International Patent Application No. PCT/US2012/033392, filed Apr. 12, 2012.

International Search Report and Written Opinion dated Feb. 3, 2014 for International Application No. PCT/US2013/063275, filed Oct. 3, 2013.

International Preliminary Report on Patentability dated Apr. 7, 2015 for International Application No. PCT/US2013/063275, filed Oct. 3, 2013.

Boileau et al., "Arthroscopic Biceps Tenodesis: A New Technique Using Bioabsorbable Interference Screw Fixation," J Arthrosc Related Surgery, vol. 18, No. 9, (Nov.-Dec. 2002), 1002-1012.

Extended European search Report dated Oct. 13, 2016, for International Application No. PCT/US2014/021774.

Extended European Search Report dated Feb. 27, 2017, PCT/US2014/022014; 10 pages.

* cited by examiner

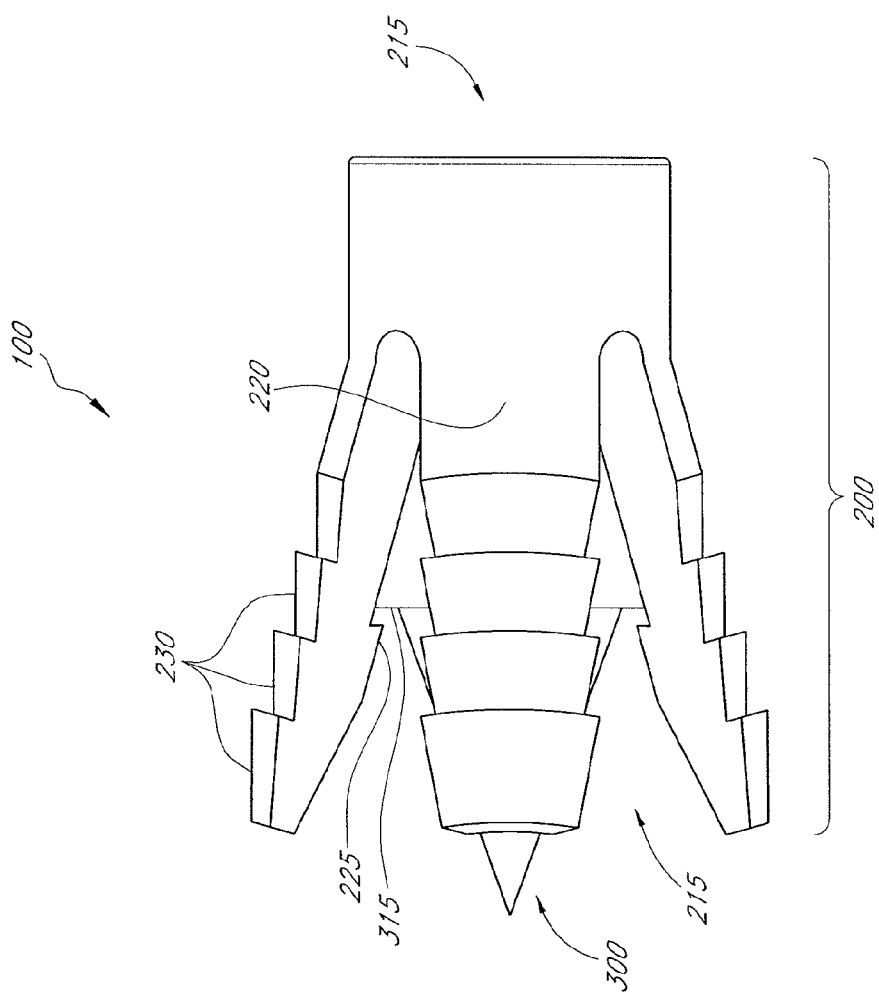

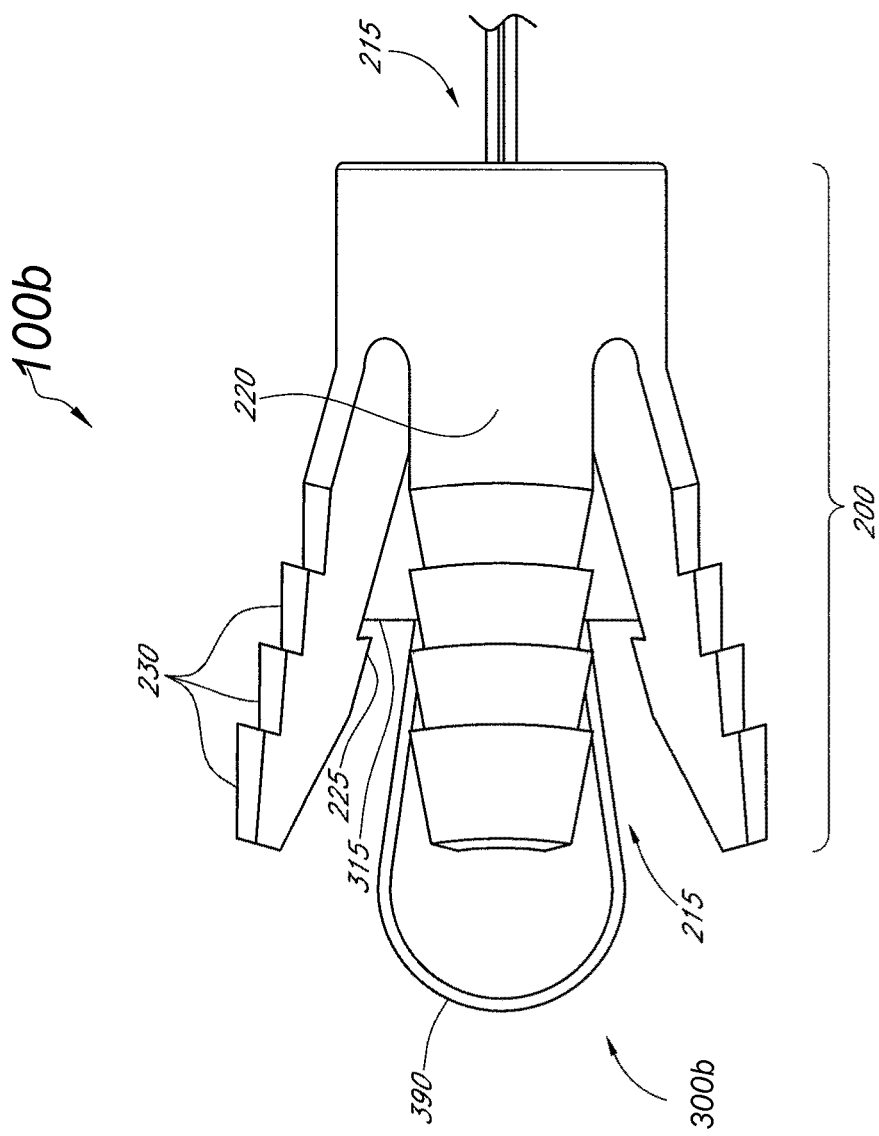

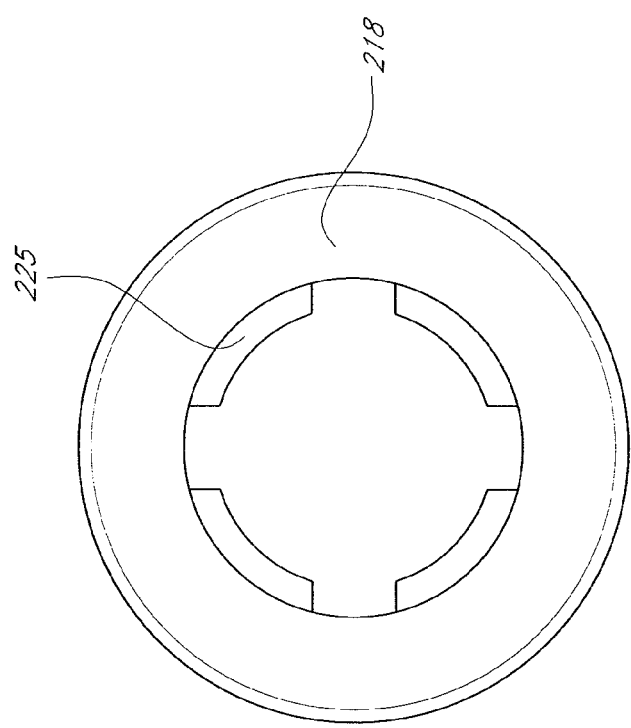

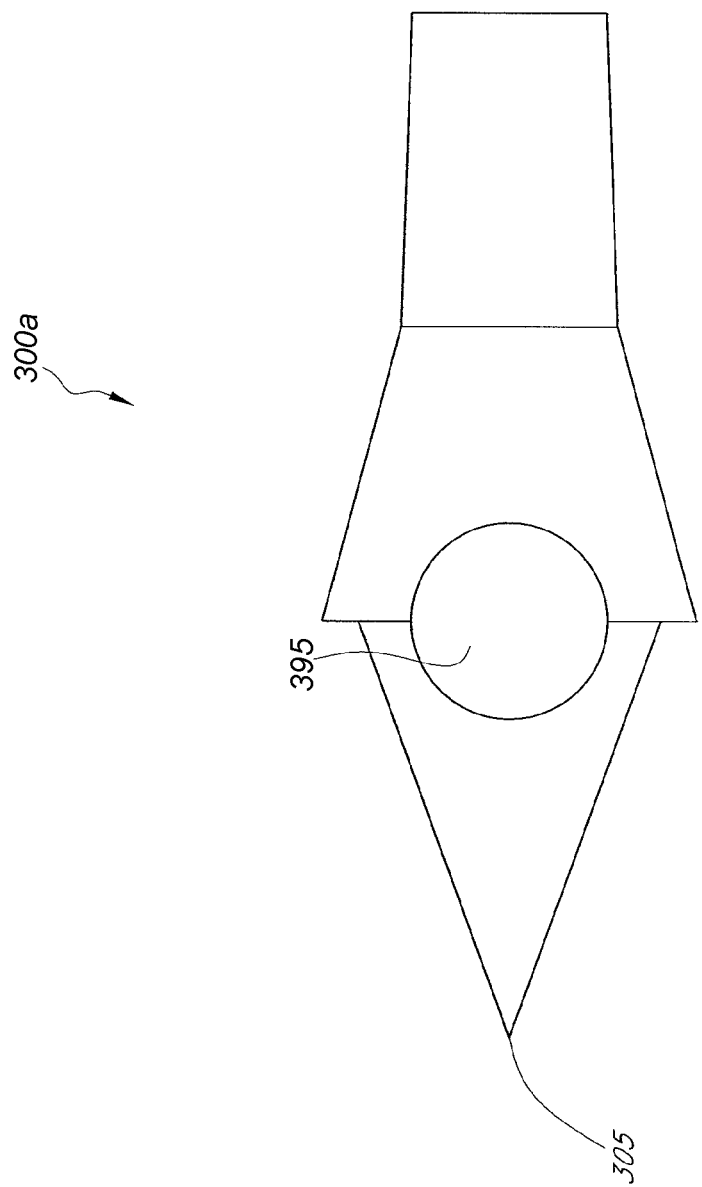

SYSTEM AND METHOD FOR SECURING TISSUE TO BONE

RELATED APPLICATIONS

This application claims priority to U.S. Provisional Application Nos. 61/251,220, filed on Oct. 13, 2009; and 61/370,791, filed on Aug. 4, 2010; both of which are incorporated herein by reference in their entirety.

BACKGROUND OF THE INVENTION

Field of the Invention

The present invention relates to medical devices and procedures. More particularly, the present invention relates to devices and methods for securing soft tissue to a rigid material such as bone.

Description of the Related Art

There are several medical procedures where a surgeon needs to attach soft tissue such as tendons or other soft connective tissue to bone. One common example is a biceps tenodesis, a surgical procedure usually performed for the treatment of biceps tendonitis of the shoulder. A biceps tenodesis may be performed as an isolated procedure, but more often is part of a larger shoulder surgery such as a rotator cuff repair.

The biceps tendon connects the biceps muscle to the bone. The tendon passes from the muscle to the shoulder joint. Patients with biceps tendon problems may have a detachment of the biceps tendon from the radial tuberosity, for example, or they may have inflammation and irritation of the biceps tendon itself. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

To perform a biceps tenodesis repair, typically a surgical procedure is used and requires the multiple steps of externalizing the tendon, whip stitching it, threading suture through a tenodesis screw, drilling the necessary bone hole and anchor insertion via screwing it in. This is a difficult procedure arthroscopically. Systems recently brought to market still require multiple steps and tools.

Another common example is a anterior cruciate ligament repair, a surgical procedure usually performed for the treatment of the ligament of the knee. An ACL repair may be performed as an isolated procedure, but is often part of multiple-repair surgery.

SUMMARY OF THE INVENTION

In one embodiment, a tissue capture anchor for attaching tissue to bone is disclosed, the anchor comprising an anchor body comprising at least two expandable tines, and a spreader configured to fit within the anchor body. The spreader comprises a pointed tip configured to spear tissue and an angled portion configured to force the expandable tines to deploy as the spreader is advanced through the anchor body. In some embodiments, the anchor body comprises a central hold adapted to receive the proximal end of the spreader. In yet another embodiment, the outside surface of the spreader comprises a lateral protrusion and the central hole of the anchor body comprises indentations adapted to engage the lateral protrusion for inhibiting movement of the proximal end of the spreader relative to the central hole. In another embodiment, the inside surface of the central hole in the anchor body comprises a groove and the proximal end of the spreader comprises a ridge adapted to fixedly snap within the anchor body's groove. Another embodiment of the anchor body is comprised of polyether-ether-ketone (PEEK). In some embodiments, the outside surface of each tine comprises at least two teeth. In other embodiments, an outside surface of the tines comprise ridges or teeth which are configured to secure the anchor body within bone.

In one method, a tissue capture anchor for attaching tissue to bone, the anchor is disclosed. The anchor includes an anchor body including at least two expandable tines; and a spreader configured to fit within the anchor body, the spreader including an angled portion configured to force the expandable tines outward as the spreader is moved relative to the anchor body. In one embodiment, the tissue capture anchor also included a distal tip comprising a suture loop extending therefrom configured to receive tissue. In one embodiment, the flat tip comprises two holes through which two limbs of the suture loop extend. In one embodiment, the anchor body further comprises a central hole adapted to receive a proximal end of the spreader, the central hole including indentations adapted to engage the lateral protrusion to thereby inhibit movement of the proximal end of the spreader relative to the central hole and also wherein the inside surface of the central hole in the anchor body comprises a groove and the proximal end of the spreader comprises a ridge adapted to fixedly snap within the anchor body's groove. In one embodiment, the anchor is made of polyether-ether-ketone (PEEK). In one embodiment, the anchor comprises at least two tines comprising at least two teeth per tine which are configured to secure the anchor body within bone.

In another embodiment, a tissue capture anchor and inserter combination is disclosed, where the combination comprises an anchor comprising a handle, an outer tube coupled to the handle, an inner rod or tube positioned within the outer tube and coupled to the spreader, an actuator shaft positioned within the handle and coupled to the inner rod, and a deployment knob coupled to the handle and the actuator shaft and configured to move the actuator shaft relative to the handle and the inner rod or tube relative to the outer tube wherein the inserter tool is configured to draw the spreader into the bone anchor to fully deploy the tissue capture anchor and secure tissue to the bone.

In another embodiment a tissue capture anchor and inserter combination is disclosed, the anchor comprising an anchor as described above, a handle; an outer tube coupled to the handle, an inner tube or rod positioned within the outer tube and coupled to the spreader, an actuator shaft positioned within the handle and coupled to the inner tube or rod; and a deployment knob coupled to the handle and the actuator shaft and configured to move the actuator shaft relative to the handle and the inner tube relative to the outer tube and wherein the inserter tool is configured to draw the spreader into the anchor body to expand the tines and secure tissue to the bone. In one embodiment, the captured tissue is folded around the anchor longitudinally. In one embodiment, the anchor further comprises a curved distal end comprising a suture loop, an angled portion, interior to the spreader, configured to force the expandable tines outward as the spreader is moved relative to the anchor body, and wherein the suture loop is configured to receive tissue. In one embodiment, the curved end comprises two holes configured to receive suture and the spreader comprises a central hole adapted to receive the proximal end of anchor body.

In yet another embodiment, a method of attaching soft tissue to bone is disclosed, the method comprising spearing the soft tissue with a bone anchor and inserting the anchor and speared tissue into the bone; wherein the anchor comprises expandable tines which are configured with teeth to engage the bone and deploying the anchor to secure it and the soft tissue in the bone. In another embodiment, the method further comprises making a clearance hole for the tissue capture anchor. In another embodiment, the clearance hole is drilled in the bicipital groove. In yet another embodiment, the clearance hole is sized to receive an anchor. In another embodiment, method further comprises making a bone hole for the tissue capture anchor. In one embodiment, he bone hole is made using an awl. In yet another embodiment, the bone hole is made with a drill. In another embodiment, the bone hole is made with the tip of the spreader.

In one embodiment, a tissue capture anchor for attaching tissue to bone is disclosed, the anchor comprising an anchor body comprising at least two expandable tines, and a spreader configured to fit within the anchor body. The spreader comprises a flat tip with apertures for sutures to form a loop and capture tissue and an angled portion configured to force the expandable tines to deploy as the spreader is advanced through the anchor body. In some embodiments, the anchor body comprises a central hold adapted to receive the proximal end of the spreader. In yet another embodiment, the outside surface of the spreader comprises a lateral protrusion and the central hole of the anchor body comprises indentations adapted to engage the lateral protrusion for inhibiting movement of the proximal end of the spreader relative to the central hole. In another embodiment, the inside surface of the central hole in the anchor body comprises a groove and the proximal end of the spreader comprises a ridge adapted to fixedly snap within the anchor body's groove. Another embodiment of the anchor body is comprised of polyether-ether-ketone (PEEK). In some embodiments, the outside surface of each tine comprises at least two teeth. In other embodiments, an outside surface of the tines comprise ridges or teeth which are configured to secure the anchor body within bone.

In some embodiments, the tissue is secured without the use of sutures or knots.

In one embodiment, the method is conducted arthroscopically. In another embodiment, the method is conducted percutaneously. In yet another embodiment, the method is conducted in open surgery.

In one embodiment, spearing the tissue and inserting the anchor comprises moving the anchor into the bone so as to capture the soft tissue into the bone.

In another embodiment, the soft tissue is secured within the bone by forcing the anchor within the bone after the tissue has been speared by the anchor.

In one embodiment, capturing the tissue and inserting the anchor comprises moving the anchor into the bone so as to capture the soft tissue into the bone.

In another embodiment, the soft tissue is secured within the bone by forcing the anchor within the bone after the tissue has been captured and secured by the anchor.

The present invention is particularly suited for use in arthroscopic procedures, including but not limited to biceps tenodesis. More broadly, it can be used in any procedure in which it is desired to capture tissue and secure to bone without the use of sutures and without tying of knots, including not only arthroscopic procedures, but also open surgery.

BRIEF DESCRIPTION OF THE DRAWINGS

FIG. 1C shows a side view of one embodiment of a tissue capture anchor in the deployed or expanded state.

FIG. 1H shows a side view of one embodiment of a tissue capture anchor in the deployed or expanded state.

FIG. 2C depicts another perspective proximal view of one embodiment of an anchor body.

FIG. 3C depicts a side view of an alternative embodiment of a spreader comprising a through-hole.

DETAILED DESCRIPTION OF THE CERTAIN EMBODIMENTS

Figure 1A:
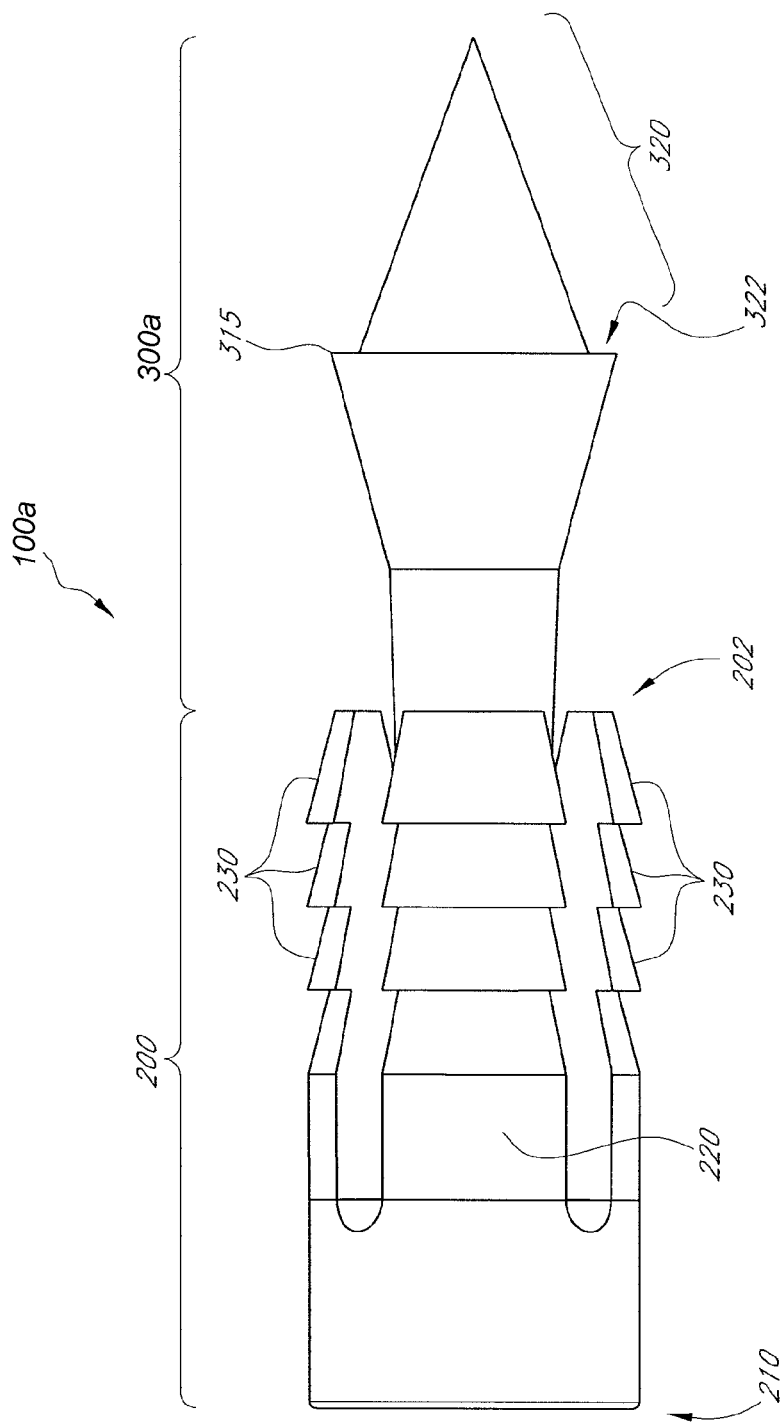
FIG. 1A shows a side view of one embodiment of a tissue capture anchor in an undeployed or unexpanded state.

In various embodiments, soft tissue may be attached to bone utilizing one or more tissue capture anchors. In the following non-limiting examples elements 100a and 100b illustrate two embodiments of a bone anchor, and likewise elements 300a and 300b illustrate a spreader element of the bone anchors. In the following paragraphs, where element 100 is used, it is assumed that elements 100a and 100b are contemplated. Where element 300 is used, it is assumed that elements 300a and 300b are contemplated. The elements 300a and 300b or their corresponding anchor embodiments 100a and 100b are referenced specifically when pertinent.

In one non-limiting example illustrated in FIGS. 1A-1E, a pointed tip is used to capture tissue. In another non-limiting example illustrated in FIGS. 1F-1J, suture loop is used to capture tissue. FIGS. 1A and 1F depict a side view of a tissue capture anchor 100 comprising an anchor body 200 and a spreader 300. FIG. 1F additionally comprises a suture loop 390. The anchor body 200 is comprised of tines 220 and teeth 230. The tines 220 expand from the distal end 210 of the anchor body 200 when the spreader 300 is engaged with the anchor body 200. The proximal end of the spreader 300 is configured to fit into the distal end 202 of the anchor body 200. In FIGS. 1A and 1F, the tissue capture anchor 100 is in the undeployed, or unexpanded position.

Figure 1B:
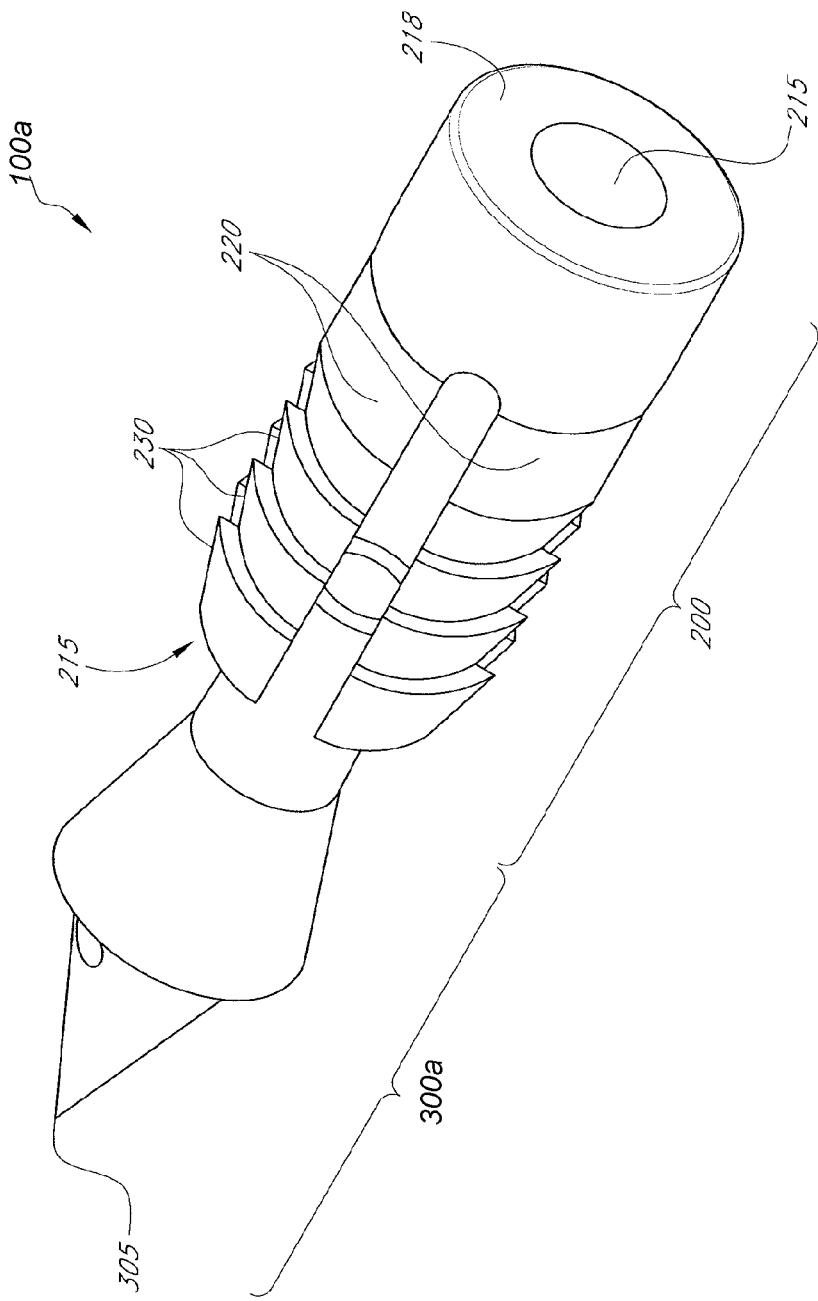
FIG. 1B shows a perspective view of one embodiment of an undeployed tissue capture anchor.
Figure 1D:
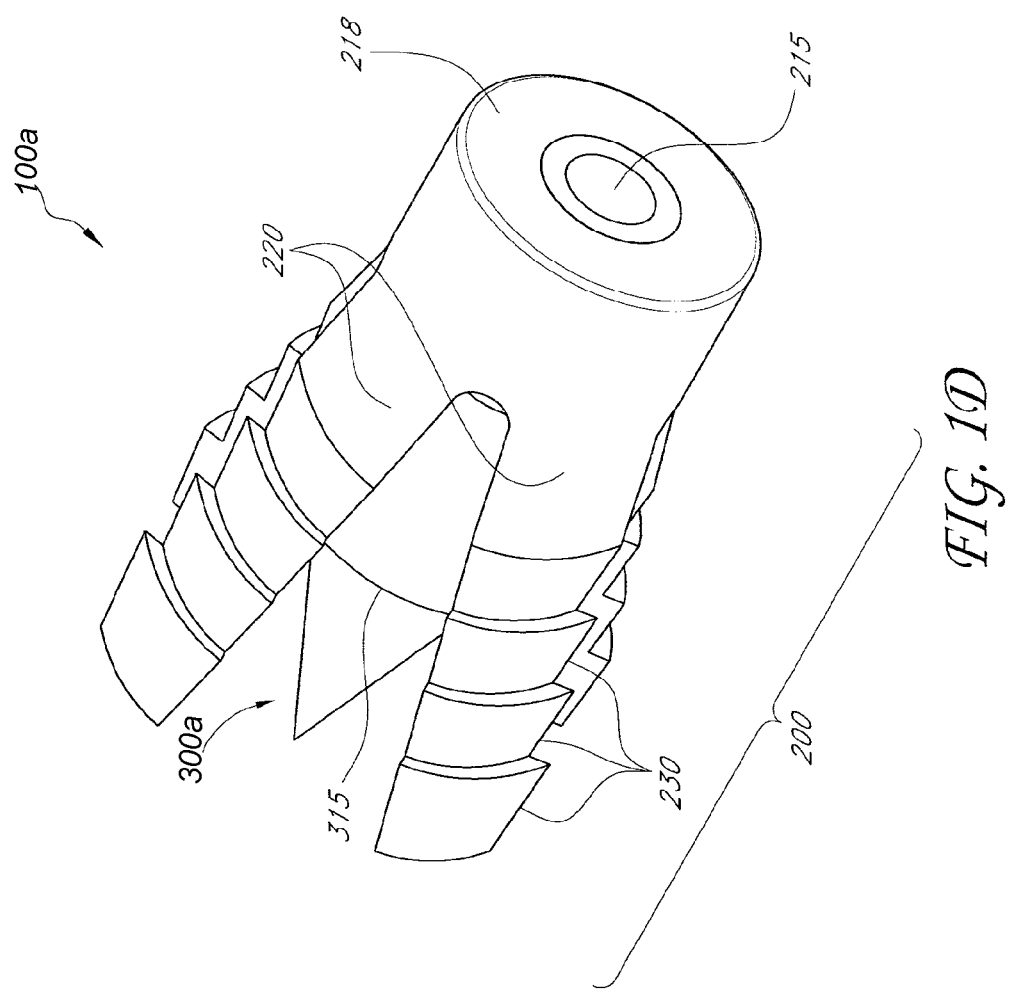
FIG. 1D shows a perspective view of one embodiment of a tissue capture anchor in the deployed or expanded state.
Figure 1E:
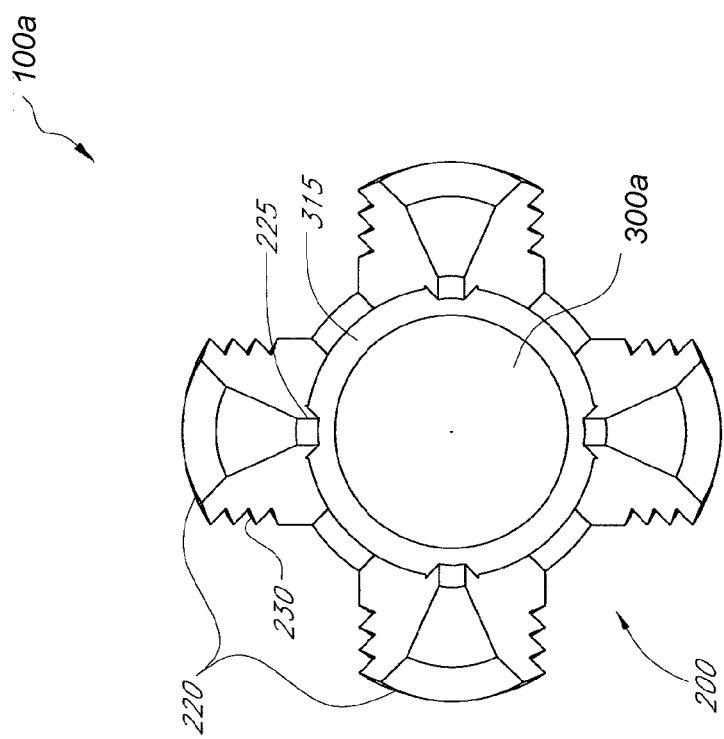
FIG. 1E shows another perspective view of one embodiment of a tissue capture anchor in the deployed or expanded state.
Figure 1F:
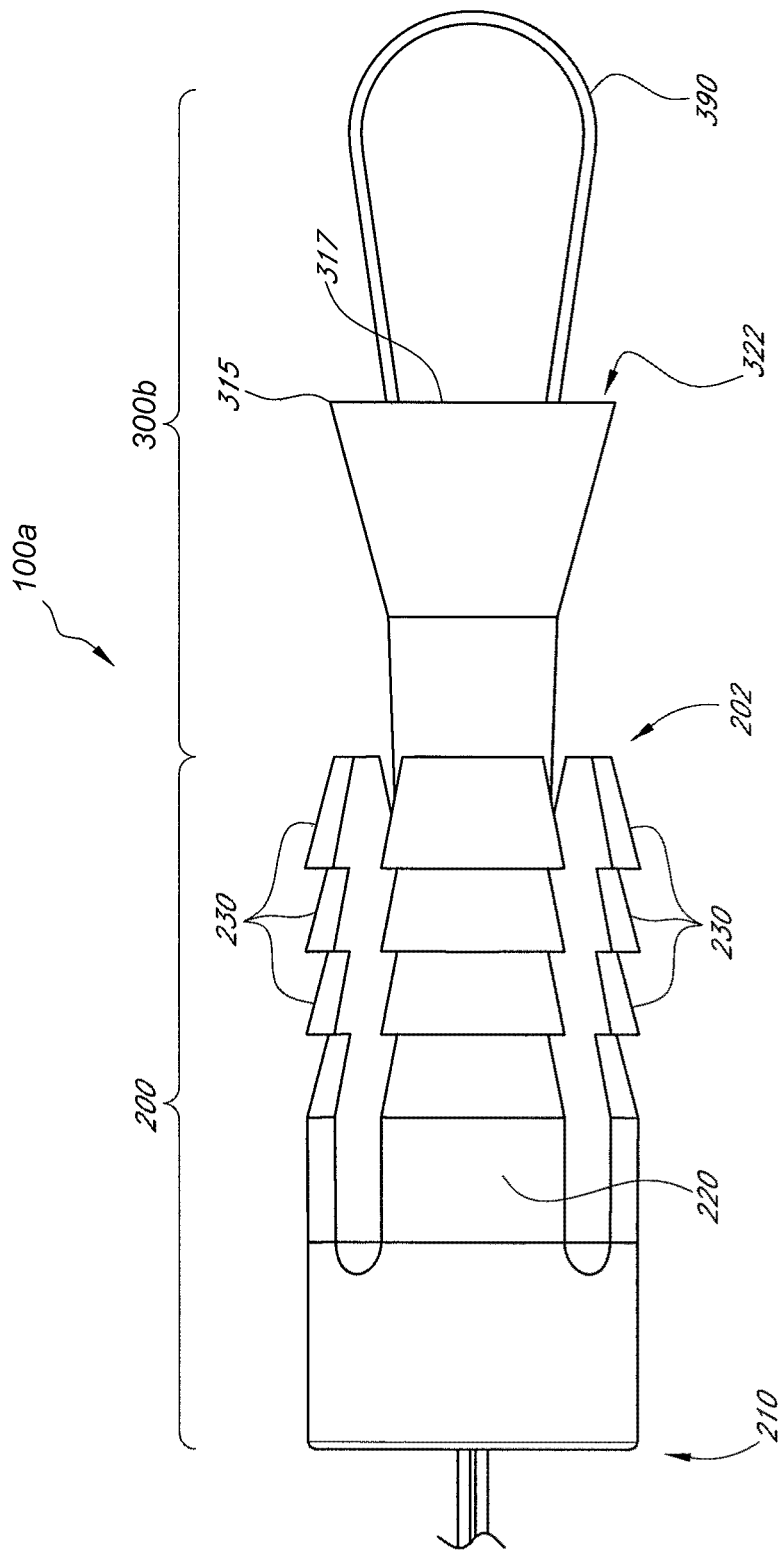
FIG. 1F shows a side view of one embodiment of a tissue capture anchor in an undeployed or unexpanded state.
Figure 1G:
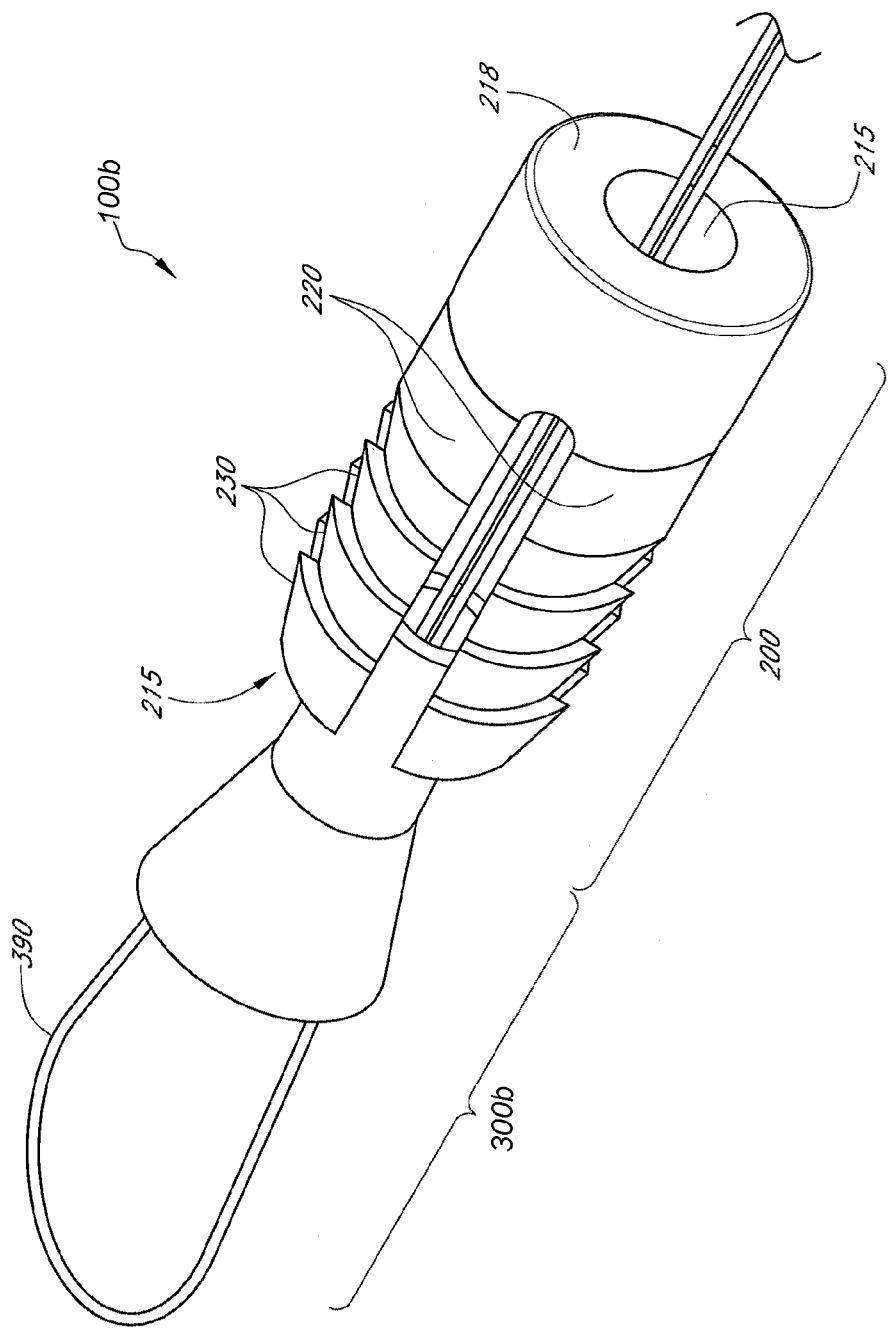
FIG. 1G shows a perspective view of one embodiment of an undeployed tissue capture anchor.

FIGS. 1B and 1G show a perspective view of the unexpanded tissue capture anchor 100. In this embodiment, the spreader 300 is slightly inserted in the central hole 215 at the distal end of the anchor body 200.

FIGS. 1C and 1H show a side view of the tissue capture anchor 100 in the deployed or expanded position. In the deployed or expanded position, the spreader 300 has been drawn up into the anchor body 200 causing the tines 220 to expand from the distal end of the anchor body 200. When deployed, the teeth 230 engage with the bone surface trapping tissue between the bone and the bone anchor 100.

The inside surface of the anchor body 200 may comprise a grooved surface 225 to engage with the ridge 315 of the spreader 300 to lock the spreader 300 into place when the anchor body 200 is fully deployed. The grooved surface 225 is oriented such that the distal end of the spreader 300 can be easily moved in the proximal direction in central hole 215 of the anchor body 200 with the ridge 315 snapping into the groove 225 as the distal end is moved proximally. However, when the ridge 315 is snapped into groove 225, proximal movement of distal end is inhibited. In some embodiments, the groove 225 can exist at different locations of the surface of the central hole or else even along substantially the entire surface of the central hole 215. In some embodiments the anchor body 200 may be coupled to the spreader 300 in several positions. In other words, in one embodiment the spreader 300 need not be inserted into the anchor body 200 as far as it will go for it to be secured to the anchor body 200.

Although a grooved surface is illustrated, it will be appreciated that other shapes are also contemplated, including multiple concentric grooves, a series of protruding ridges, or any other suitable structure that permits a spreader 300 to be securely locked within the central hole of the anchor body 200.

Figure 1I:
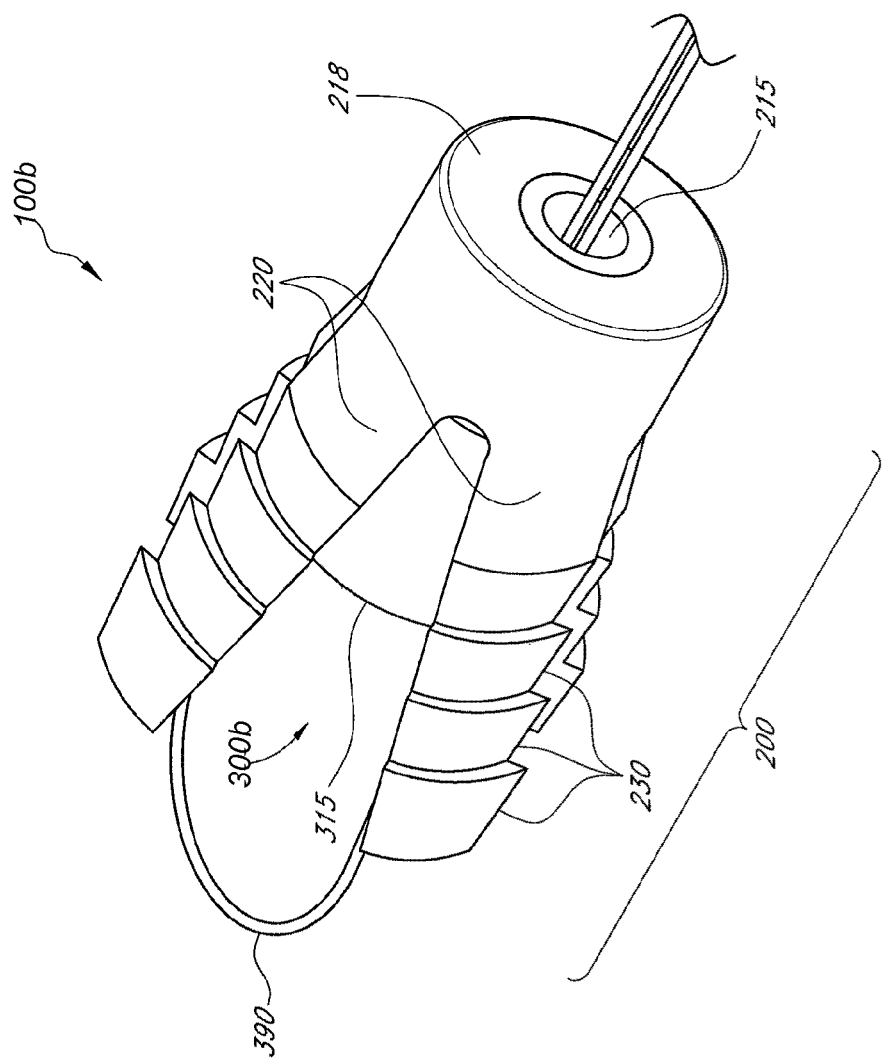
FIG. 1I shows a perspective view of one embodiment of a tissue capture anchor in the deployed or expanded state.

With reference to FIGS. 1D and 1I, which are each a perspective view of the top and side of anchor body 200 engaged with the spreader 300, the top (proximal end) comprises a hole 215 in the center for receiving the spreader 200. In some embodiments, the top surface 218 of the anchor body 200 may be textured such as with a scallop shape or grooves so as to inhibit movement of an insertion tool against the surface of the anchor body.

During deployment, the spreader 300 is drawn into the anchor body 200 causing the tines 220 to expand from the distal end of the anchor body 200. Also during deployment, the spreader 300 is drawn into the anchor body 200 until the ridge 315 of the spreader 300 passes a groove 225 in the anchor body 200. When the spreader passes this point, the ridge 330 and groove 225 engage or click and the spreader 300 is locked into place and the anchor body 200 cannot undeploy or reverse and the spreader 300 cannot reverse direction.

Figure 1J:
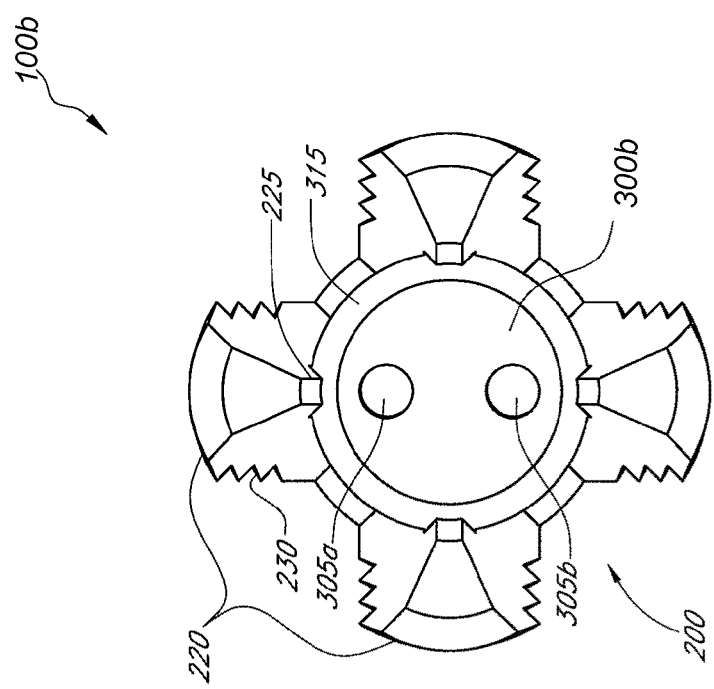
FIG. 1J shows another perspective view of one embodiment of a tissue capture anchor in the deployed or expanded state.

FIGS. 1E and 1J each show a distal end view of the tissue capture anchor 100. In this view the anchor body 200 is fully deployed. The spreader 300 is securely fixed into the anchor body 200 and the ridge 315 and groove 225 of the anchor body 200 will keep the spreader 300 from being uninserted or reversed from the anchor body 200. The tines 220 are fully expanded. Since the teeth 230 are facing the opposite direction from the view of FIGS. 1E and 1J, only their edges are visible along the edges of the tines 220.

Figure 2A:
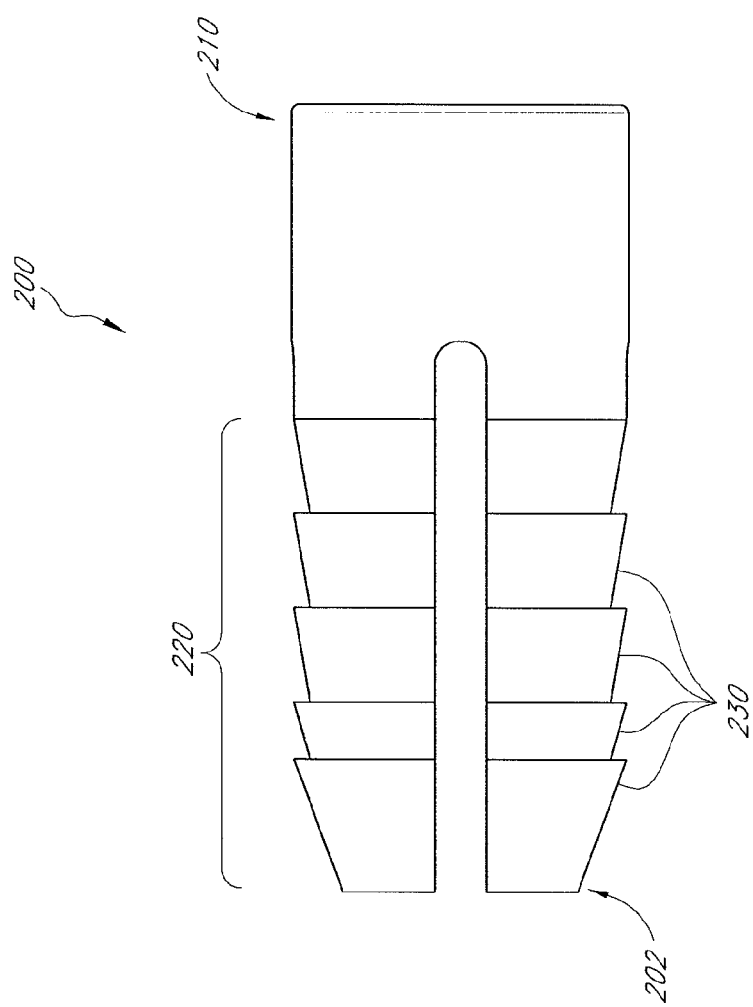
FIG. 2A depicts a side view of one embodiment of an anchor body.
Figure 2B:
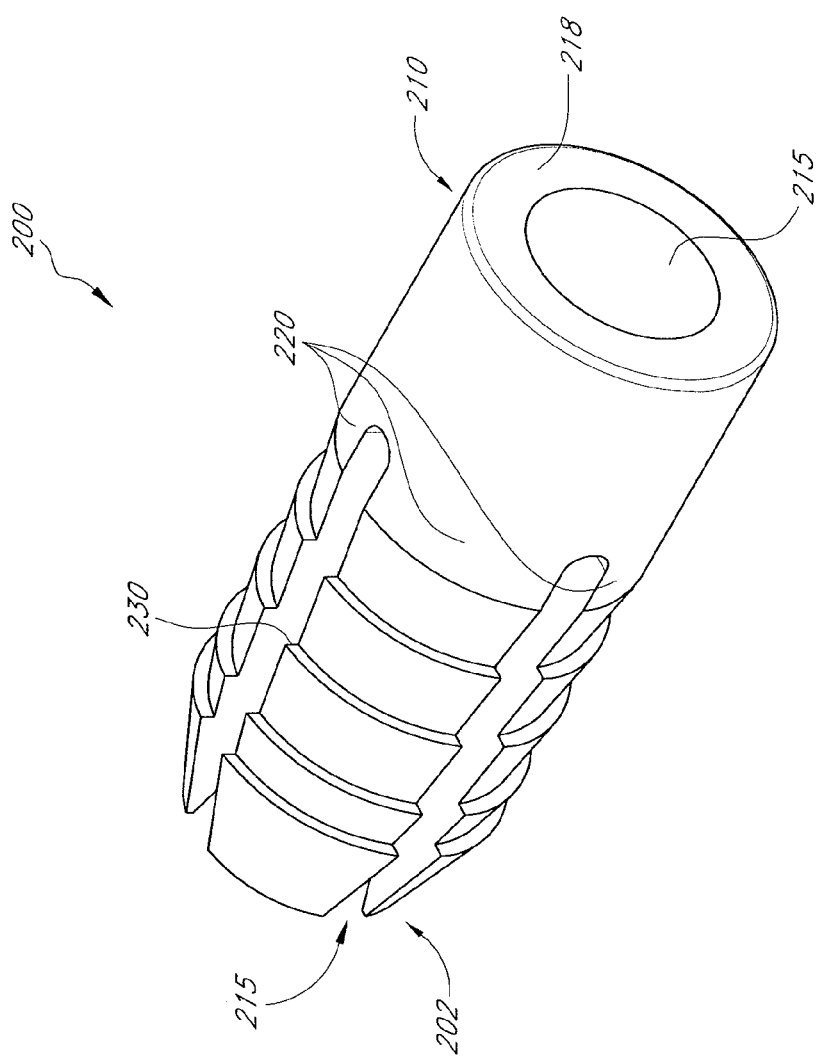
FIG. 2B depicts a perspective view of one embodiment of an anchor body.
Figure 2D:
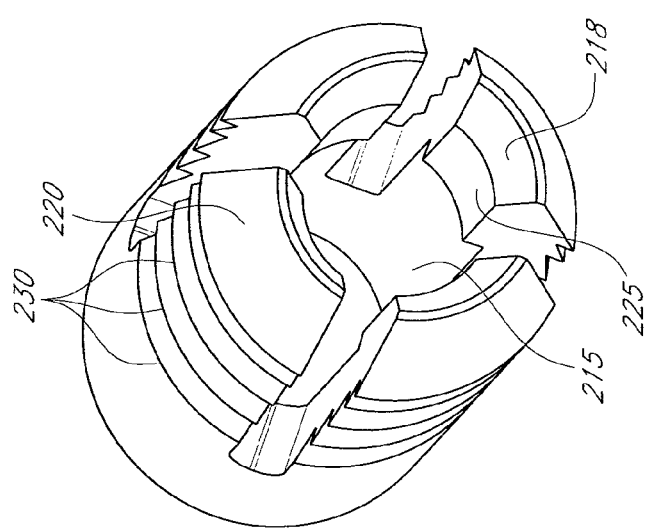
FIG. 2D depicts a perspective distal view of one embodiment of an anchor body.

FIGS. 2A-2D depict an embodiment of an undeployed anchor body 200. FIG. 2A depicts a side view of the anchor body 200. FIG. 2B depicts a perspective view of an embodiment of the anchor body 200. FIG. 2C depicts a view from the proximal end of the anchor body 200, and FIG. 2D depicts a perspective view from the distal end of the anchor body 200. The proximal end 210 of the undeployed anchor body 200 is generally cylindrical in shape with a diameter larger than distal end 202. With reference to FIGS. 2B-2D, a hole 215 may advantageously be provided in the center of proximal end 210. With reference to FIG. 2B, the bottom of distal end 202 also contains a hole 215. Hole 215 comprises a central opening that extends through the anchor body 200. In some embodiments the anchor body 200 comprises a groove 225 in its inner surface, as shown in FIGS. 2C-2D. Thus, the inner surface of the anchor body 200 is not flat. In some embodiments, some or all of these surfaces may be textured such as with a scallop shape or grooves so as to inhibit movement of spreader 300 once it is withdrawn into the anchor body. In some embodiments, texturing in the inner surfaces of anchor body 200 matches texturing in the outer surfaces of the spreader 300. It will be appreciated that the illustrated embodiments represent only one possibility; thus, other shapes for the surface of proximal end 210 may also be used.

The distal end 202 of the anchor body 200 is configured to receive the spreader 300. Hole 215 in anchor body 200 is an opening into a central ("axial") bore into and through the anchor body 200. The sides of the opening preferably include a groove for engaging with the spreader 300. It will be appreciated that other methods of securing the spreader 300 within the anchor body 200 may be used, such as a frictional fit or threading.

The anchor body 200 is comprised of tines 220 which spread outwardly when engaged with the spreader 200. The tines 220 engage with the bone fixedly securing the anchor body 200 in the bone. The tines comprise a number of teeth 230 which further engage with the tissue and bone in the deployed tissue capture anchor 100. The number of tines 220 and teeth 230 can vary. In one embodiment, there are four tines 200 with five teeth 230 per tine 220. The proximal end 210 of the anchor body 200 is configured to receive an inserter component, which is inserted through the hole 215 in the center of the anchor body 200 and is coupled with a spreader 300.

The distal end 202 of the anchor body 200 may advantageously be tapered to facilitate insertion of the anchor body 200 into bone. The anchor body 200 has at its widest point, a diameter not larger than the widest point of the spreader 300.

Figure 2F:
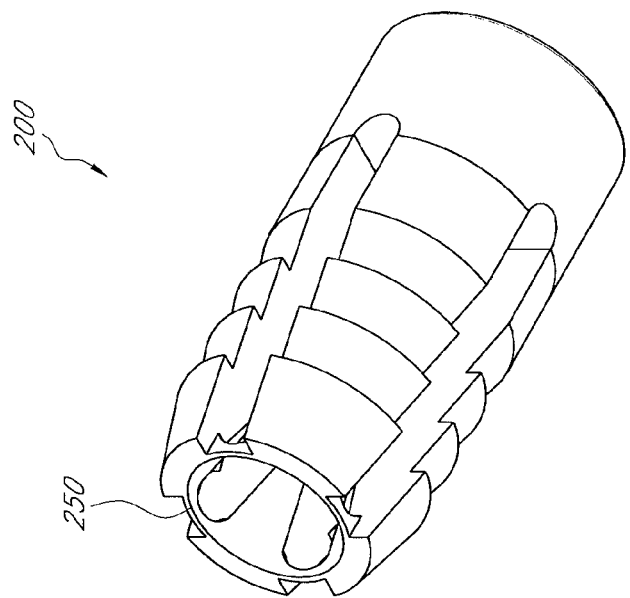
FIGS. 2E and 2F depict an alternate embodiment of an anchor body.
Figure 2E:
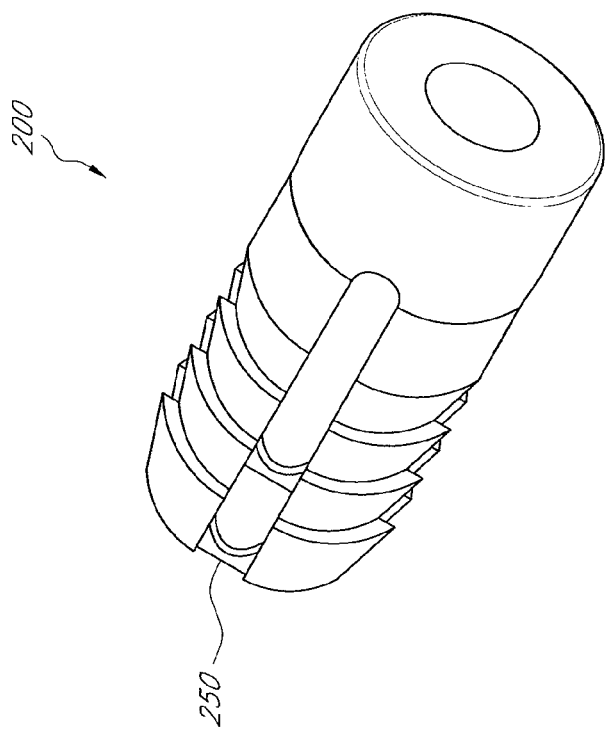

FIGS. 2E and 2F depict an alternate embodiment of an anchor body 200. In this embodiment, the anchor body also comprises webbed portions 250 across the distal ends of the tines 230. These webs 250 are easily broken when the spreader 300 is engaged with the anchor body 200. The webs 250 protect against premature deployment of the anchor upon insertion into the bone by keeping the tines 220 intact until they are expanded via the spreader 300.

Figure 3A:
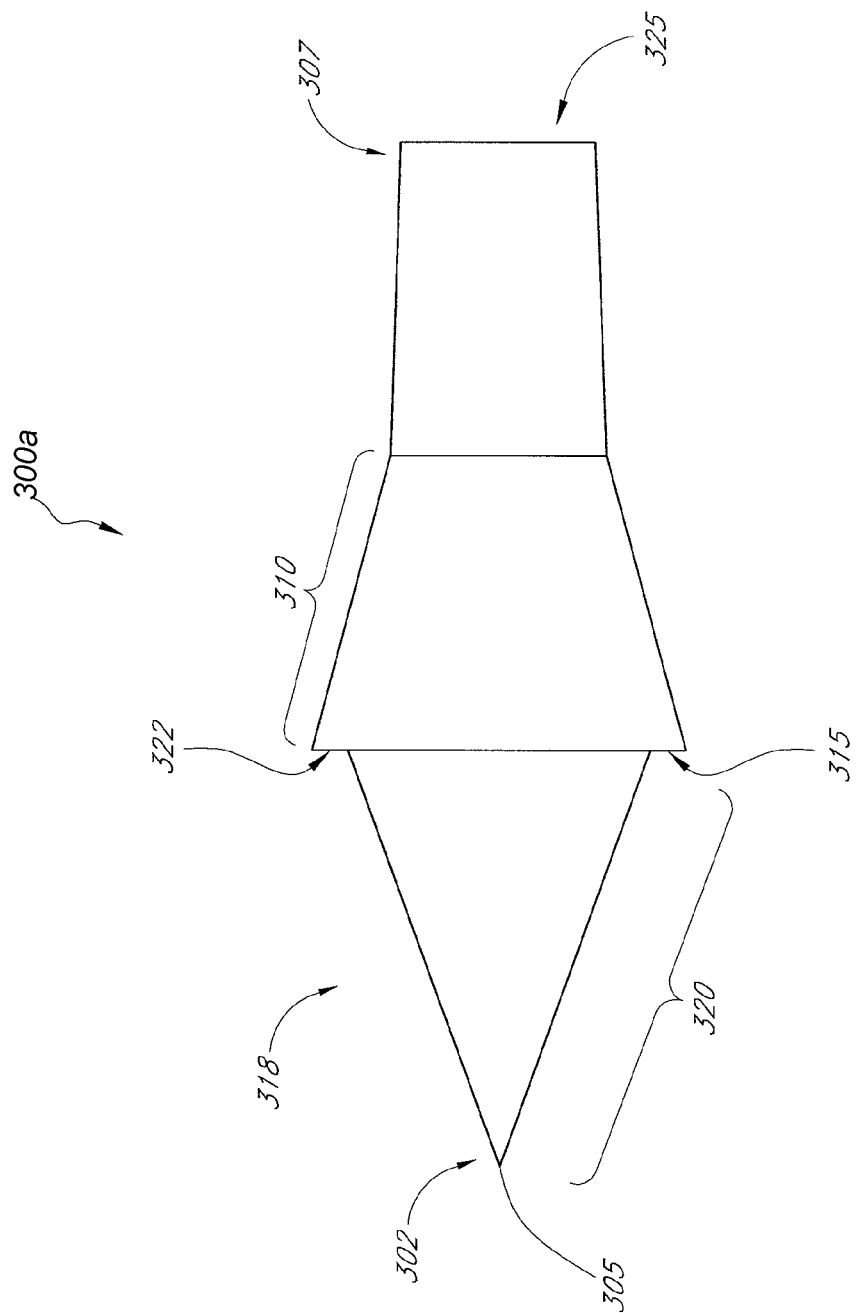
FIG. 3A depicts a side view of one embodiment of a spreader.
Figure 3B:
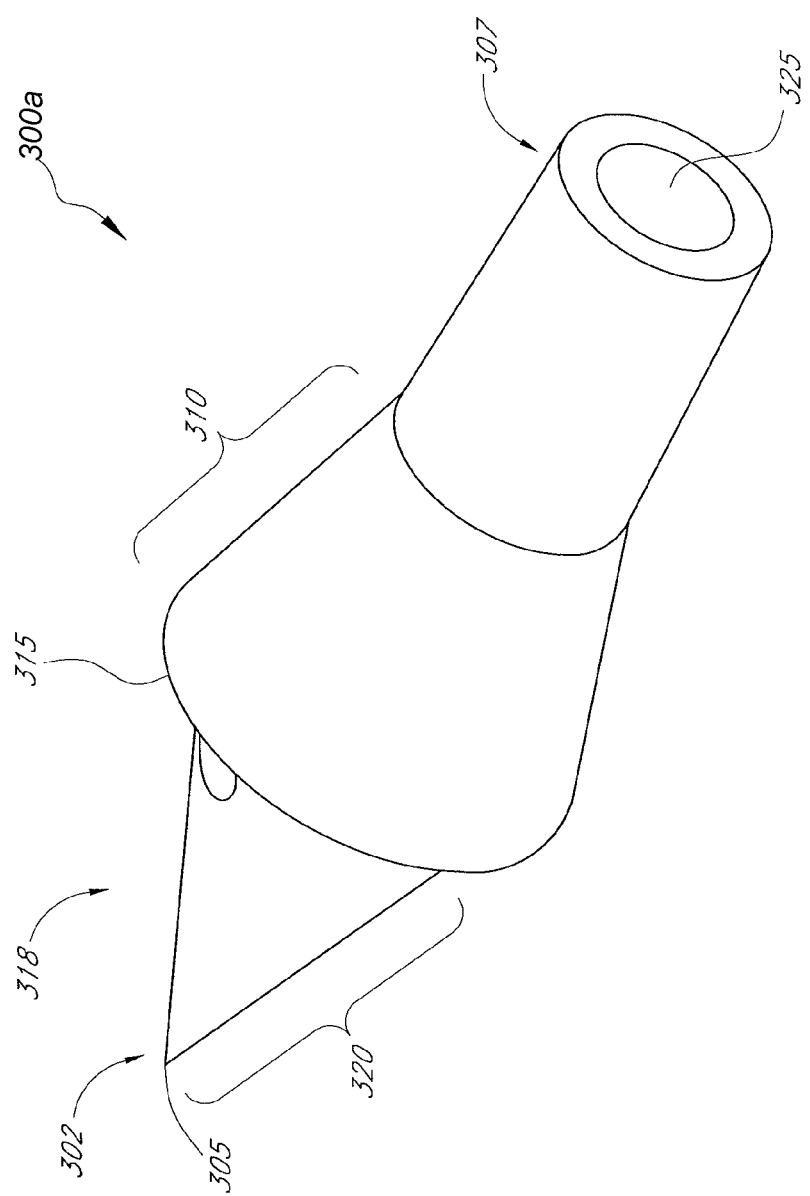
FIG. 3B depicts a perspective view of one embodiment of a spreader.
Figure 3D:
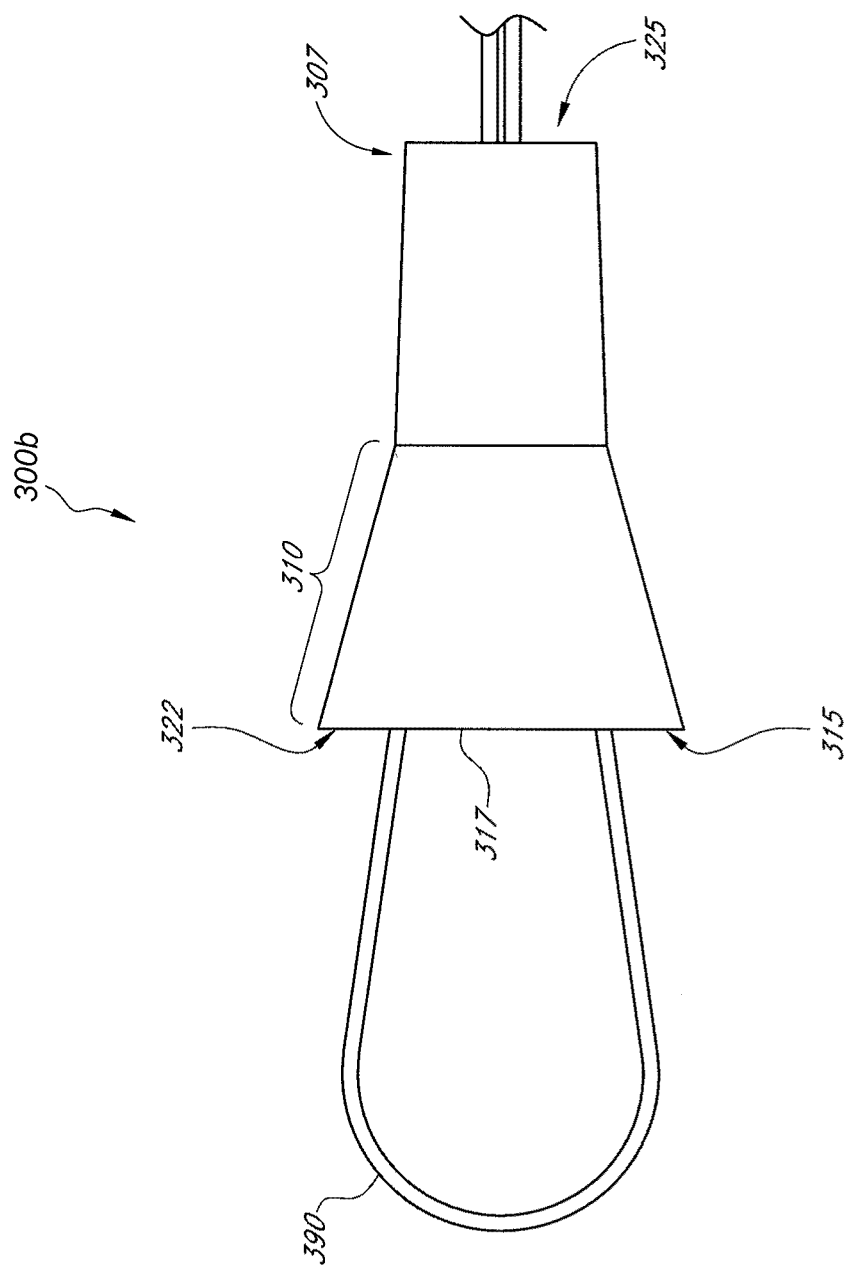
FIG. 3D depicts a side view of one embodiment of a spreader.
Figure 3E:
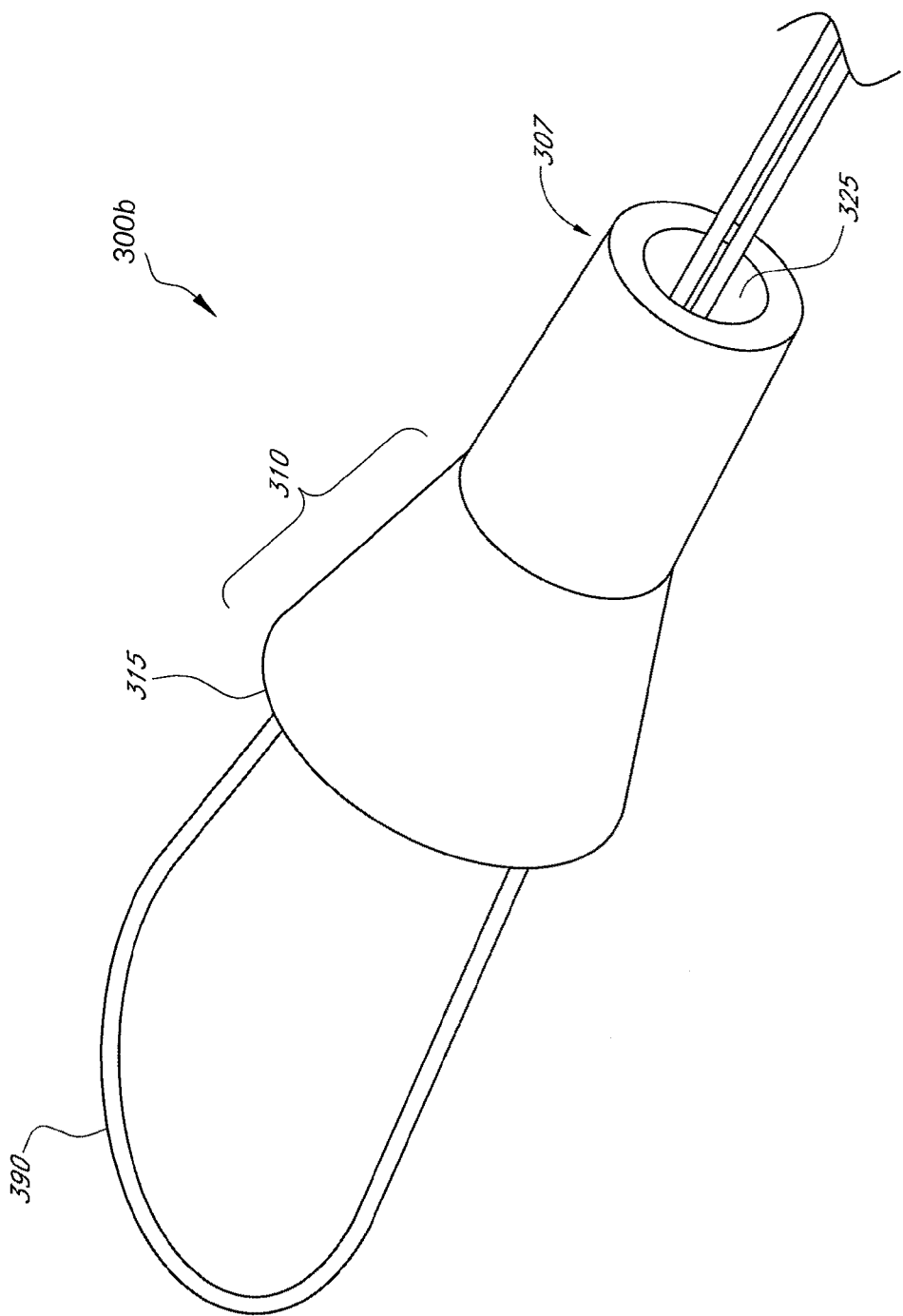
FIG. 3E depicts a perspective view of one embodiment of a spreader.
Figure 3F:
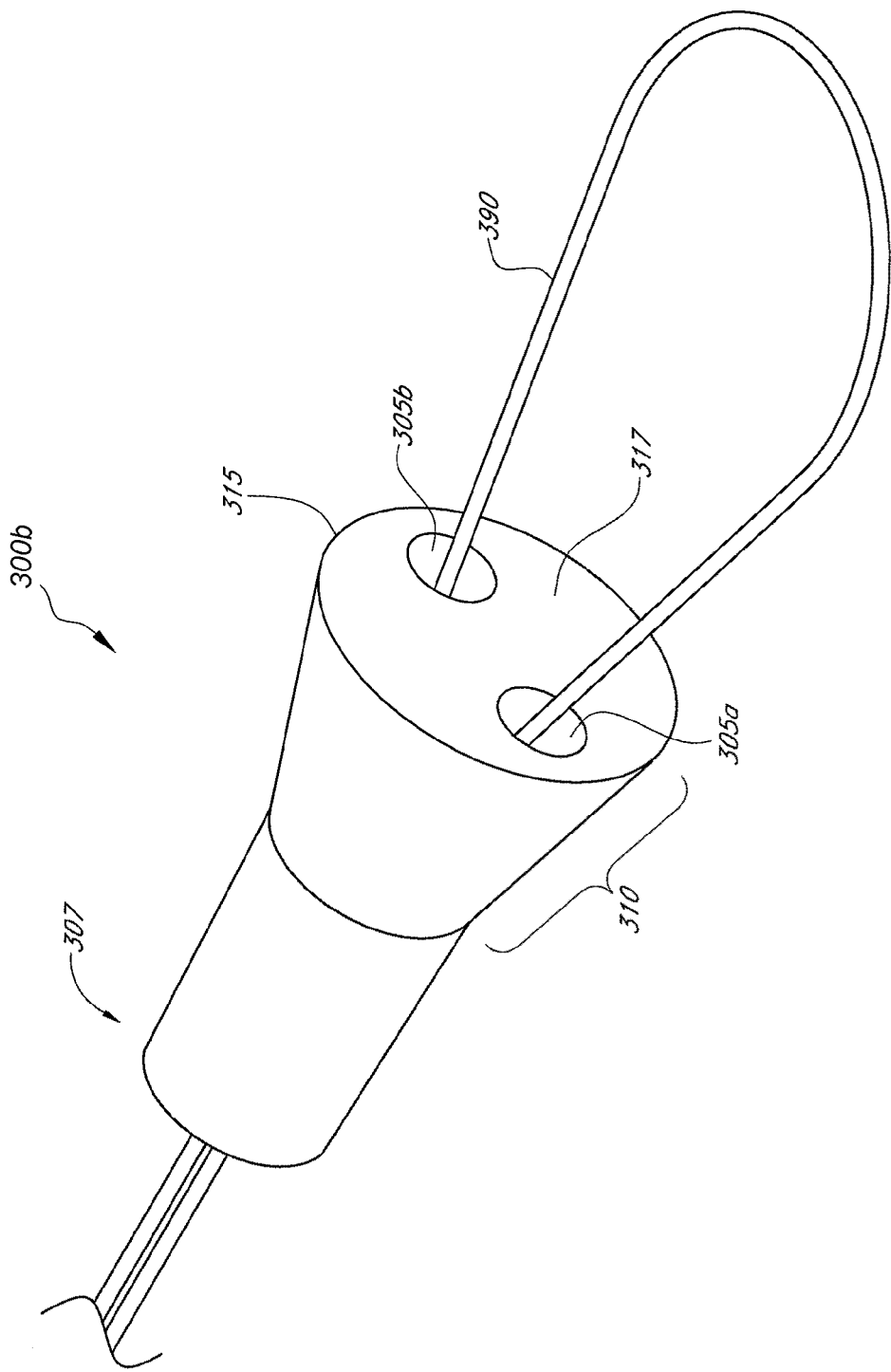
FIG. 3F depicts another perspective view of one embodiment of a spreader.

FIGS. 3A-3C depict one embodiment of a spreader 300a with a pointed tip. FIGS. 3D-3F depict another embodiment of a spreader 300b with a flat face and comprising a suture loop.

FIG. 3A shows a side view of an embodiment of the spreader 300a. FIG. 3B shows a perspective view of the spreader 300a. The spreader 300a comprises a generally cone-shaped 320 pointed distal end 302 and a proximal end 307 with a means 325 for receiving an insertion tool, a central body 310, a ridge 315 and a narrow section 318. The distal end 302 further comprises a tip 305 for engaging the tissue. The proximal end 307 is configured for coupling with an inserter. For instance, in this embodiment, the proximal end 307 of the spreader 300a comprises a hole 325 that receives the inserter tool for coupling.

The spreader 300a further comprises central body 310 which gradually widens from the proximal end and forms a ridge 315 before it narrows again 318 and joins with proximal end of the tip 305. The distal end 302 is generally cone shaped 320, meaning that it gradually widens in a conical shape until it fits with the central body 310 at the site of the ridge 318. In some embodiments, the ridge 315 may be slightly undercut 322 which may result in a stronger lock in the bone when then the anchor is fully deployed.

The tip 305 of the spreader 300a can be sharp and configured to spear or stab tissue and drag it into a bone hole before the tissue capture anchor 100 is deployed.

The spreader 300a is configured to be drawn into the distal end of the anchor body 200 via an insertion tool. As the tissue capture anchor 100 is deployed, the spreader 300 is further advanced into the anchor body 200, spreading the tines 220 of the anchor body 200 until the ridge 315 of the spreader 300a engages the groove 225 in the inside of the anchor body 200 at which point it locks into place. In one embodiment, the ridge 315 is undercut 322 providing even more security for reversing.

In another embodiment, the spreader 300a further comprises a hole 325 that extends longitudinally through the spreader 300a to the distal end. In this embodiment, the tip of the spreader 305 is open to allow the insertion tool to extend through the spreader 300a. In some embodiments, the tip of the insertion tool will be pointed and/or sharp to assist in spearing tissue.

In one alternative embodiment, the spreader 300a comprises a transverse through-hole configured to receive soft tissue. FIG. 3C depicts a side view of a spreader 300a having the through-hole 395. In this embodiment, tissue is captured by the anchor by threading one or more tissue bundles (for example, single or double bundles of tendon) through the through-hole 395. When the anchor with threaded tissue bundles is inserted into bone, the tissue will follow a serpentine path along the sides of the anchor, through the through-hole 395, and back out of the bone. In these embodiments, tissue may be captured by only threading through the through-hole 395 or also by piercing with the tip 305 of the spreader 300 (for example, piercing of other bundles of soft tissue).

In some embodiments, the entire anchor may be enlarged to accommodate a suitably sized through-hole 395 in the spreader 300a. In one non-limiting embodiment, an 8 mm diameter anchor with a 4 mm diameter through-hole 395 is used. In one embodiment, the through-hole is approximately 6 mm in diameter. Other sizes of through hole are contemplated.

FIG. 3D shows a side view of an embodiment of the spreader 300b. FIG. 3E shows a perspective distal view of the spreader 300b, and FIG. 3F shows a perspective proximal view. The spreader 300b comprises a generally flat face at distal end 17 and a proximal end 307 with a means for receiving an insertion tool 325, a central body 310, and a ridge 315. The distal end 302 further comprises two holes 305a and 305b for receiving the limbs of a suture loop 390. The proximal end 307 is configured for coupling with an inserter. For instance, in this embodiment, the proximal end 307 of the spreader 300b comprises a hole 325 that receives the inserter tool.

The spreader 300b further comprises central body 310 which gradually widens from the proximal end and forms a ridge 315 around the face 317. The spreader 300b comprises a tube shaped base 310 at the proximal end 307 with a axial bore 325 for receiving sutures 390 and an insertion tool, a generally conical shaped spreader at the distal end which is wider than the proximal end, and an optional ridge 315 at the tip of the distal end. The distal end can further comprise a flat area around the axial bore 325. The proximal end 307 is configured for receiving sutures and coupling with an inserter. For instance, in this embodiment, the proximal end 307 of the spreader 300b comprises a hole 325 that receives the inserter tool for coupling and sutures 390.

The spreader 300b comprises the base section which joins with the gradually expanding distal spreader end 302. The distal end is generally 310, meaning that it gradually widens in a conical shape from the base section to the distal end of the spreader 300b, which comprises a flat area 317 and through which the axial bore 325 extends into two openings 305a, 305b. In one embodiment, the distal end may also comprise a ridge 315, which may optionally be slightly undercut 322 to result in a stronger lock in the bone anchor when the anchor is fully deployed.

The axial bore 325 may be used to receive sutures (see FIGS. 1f-1J). In one embodiment, a loop of suture is secured through the axial bore 325 such that a loop of suture extends from the spreader for use in a surgical procedure. The distal end of the spreader 300b comprises two openings 305a, 305b to the axial bore 325 through which the suture loop 390 extends. The resulting length of suture extends from the proximal end of the spreader through the axial bore 325 and through to the distal end where it is threaded through hole 305a and then back through 305b and back through the proximal end, forming a loop. The suture loop 390 extending through the distal end of the spreader 300b is freely slidable, for example, such that it can be moved or adjusted back through the axial bore 325.

The spreader 300b is configured to be drawn into the distal end of the anchor body 200 via an insertion tool. As the tissue capture anchor 100 is deployed, the spreader 300b is further advanced into the anchor body 200, spreading the tines 220 of the anchor body 200 until the ridge 315 of the spreader 300b engages the groove 225 in the inside of the anchor body 200 at which point it locks into place. In one embodiment, the ridge 315 is undercut 322 providing even more security against reversing.

As discussed above, the tines 220 in the anchor may be in a low-profile streamlined position prior to insertion into bone. A spreader 300b is used after insertion to expand the tines 220 such that their teeth 225 engage bone. The spreader 300b may comprise any suitable shape configured to be inserted through the axial bore 215 in the anchor body 200 and make contact with the tines 225. The spreader 300b may be at least partially positioned within the axial bore of the anchor prior to tine expansion as depicted in FIG. 1G. As the spreader 300b is moved from a first lower position to a second upper position, the proximal end of the spreader 300b is designed to spread or force the tines 220 from a first low-profile position (for example, an internal lateral position) to a second external lateral position. In one embodiment, the proximal end of the spreader 300b may have ridges to assist in preventing slippage or mis-alignment.

The spreader 300b will remain in the anchor with the tines 220 in their fully spread position. The force provided by the tines' 220 interaction with the bone keeps the spreader 300b tightly engaged. Further protection against slipping or tilting of the spreader 300b is provided by the optionally ridged sides of the spreader 300b. In one embodiment, the spreader 300b may have ridges or indentations to assist in a tight fit such that accidental slipping or adjustments are minimized. In one embodiment, one or more of the tines 220 have an indentation on a side facing the central axis of the anchor. A ridge on the spreader can then engage the indentation, thereby stabilizing the spreader 300b and preventing the spreader 300b from being advanced too far into the anchor. In an alternative embodiment, the spreader comprises an indentation (for example, an indentation in a ridge on the spreader 300b) that can engage with a protrusion on a side of a tine facing the central axis of the anchor. In addition to stabilizing the spreader 300b and preventing over insertion, this feature also prevents rotation of the spreader 300b relative to the anchor.

In this embodiment, tissue is captured by the anchor by threading one or more tissue bundles (for example, single or double bundles of tendon) through the suture loop 390. The suture loop is tightened around the tendon such that the tendon is secured to the face 317 of the spreader 300b. Securing the tissue can be accomplished by pulling or advancing the suture loop so that it secured the tissue to the anchor 100. When the anchor with threaded tissue bundles is inserted into bone, the tissue is held in place at the distal end of the spreader and will be held secure against the sides of the bone hole and further secured by the expanded tines, as described herein, along the sides of the anchor, and back out of the bone. In these embodiments, tissue may be captured by only threading through the suture loop 390. In some embodiments, the suture loop may additionally comprise a knot on the end.

In a preferred embodiment, the tissue capture anchor 100 is made entirely of a biocompatible engineering plastic such as polyether-ether-ketone (PEEK). Other embodiments include a tissue capture anchor entirely or in part of a non-metallic substance that is biocompatible. Biocompatible materials such as poly ether ketone (PEK), polyetherimide (ULTEM), ultrahigh molecular weight polyethylene (UHMPE), polyphenylene, or some other engineering polymer materials known to those of skill in the art may be used. A non-metallic anchor system may provide certain advantages such as, for example, eliminating MRI artifacts.

Figure 4:
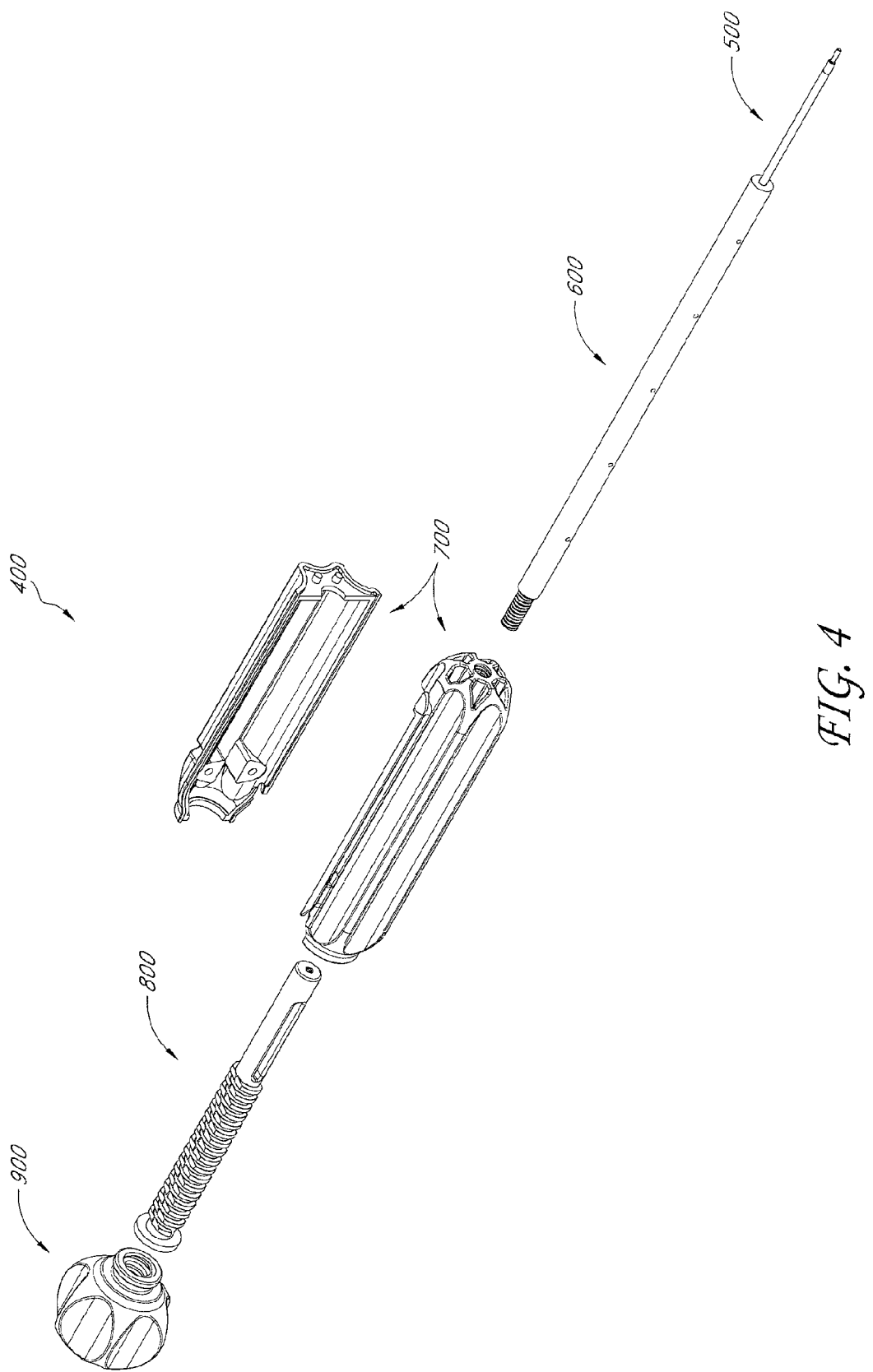
FIG. 4 shows an exploded view of one embodiment of an inserter tool.

FIG. 4 depicts individual components of an inserter tool. The inserter tool comprises an inner rod or tube 500, an outer tube 600, a handle body 700, a threaded actuator shaft 800, and a deployment knob 900. In some embodiments, the inserter 400 is coupled to the tissue capture anchor 100 during manufacturing. In a preferred embodiment, the inserter tool is disposable.

The inserter tool 400 is designed to insert and manipulate a tissue capture anchor such the tissue capture anchor 100 described in FIGS. 1A, 1B, 1F and 1G. In some embodiments, the tissue capture anchor 100 is manufactured to be attached to inserter tool before packaging. In other embodiments, the tissue capture anchor is coupled to the inserter tool prior to insertion. In a basic configuration, the inserter tool is assembled as follows: the inserter tool 400 is configured such that the inner rod 500 is disposed within the outer tube 600. The outer tube is configured to fit against the proximal end of the stabilizer. The inner rod 500 extends through outer tube 600 and is configured to attach to the spreader 300 via threading on both the proximal hole in the spreader 300 and threading on the distal end of the inner rod 500. The proximal end of the outer tube 600 is connected to a handle 700 and the inner rod 500 extends through the proximal end of the outer tube 600 and screws into the threaded actuator shaft 800. The actuator shaft 800 extends just past the proximal end of the handle 700 where it is configured to secure with a deployment knob 900.

The individual components of the inserter tool are further described in detail below.

Figure 5:
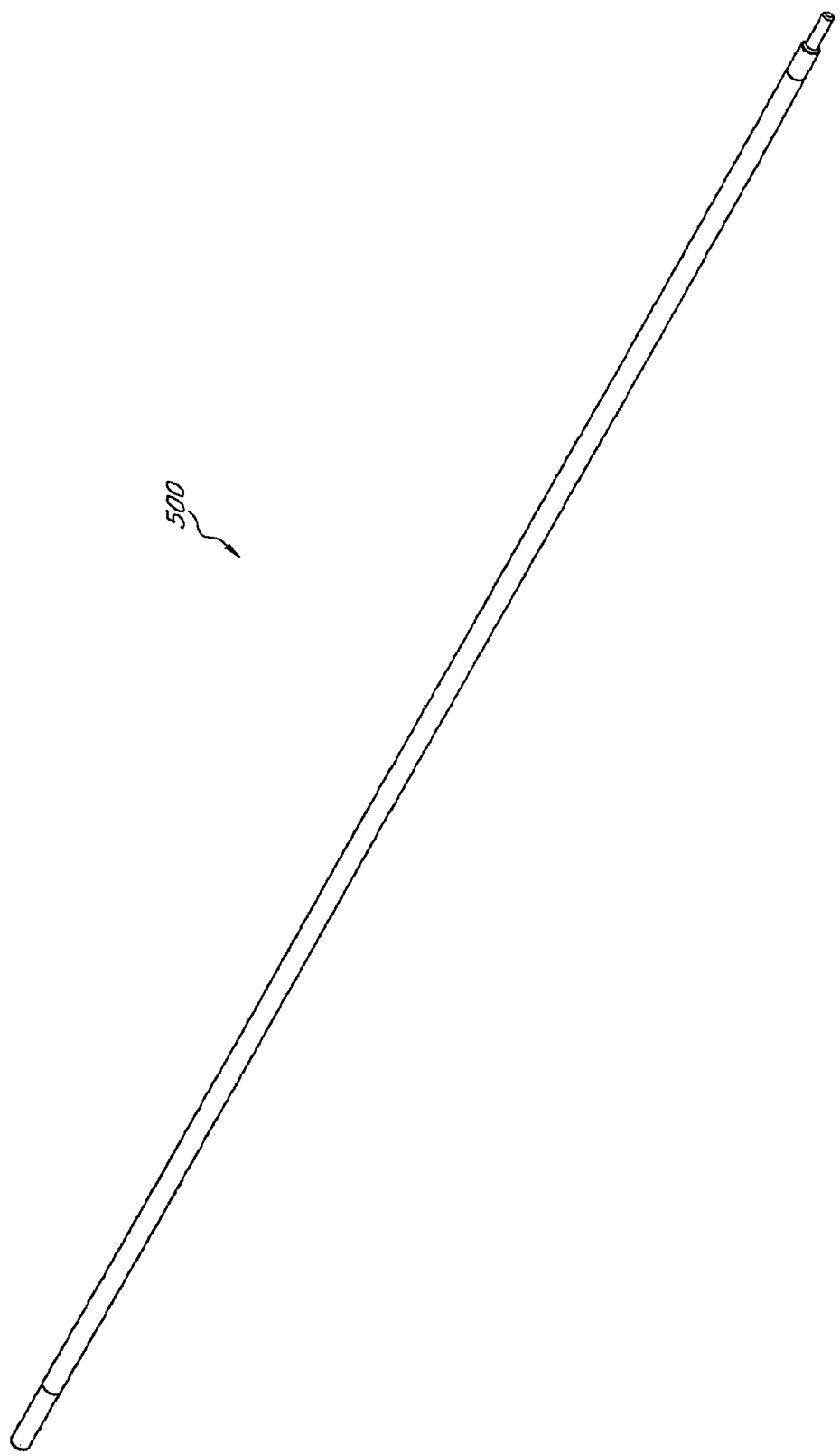
FIG. 5 shows a perspective view of one embodiment of an inner rod component of an insertion tool.

FIG. 5 shows a perspective view and a side view of an embodiment of the inner rod 500, respectively. In some embodiments, the inner rod is an inner tube. The inner rod comprises a distal end configured to secure to the spreader 300, a proximal end which is configured to interact with the other components of the inserter, for instance the actuator shaft 800. The inner rod 500 is configured that a proximal end is advanced through the outer tube 600 and into the handle 700 where it is further secured within the actuator shaft 800 via threading. The distal end of the inner rod 500 is configured to be advanced through the central hole in the anchor body 200 and then secured to the spreader 300 until the tissue capture anchor 100 is fully deployed and the inner rod 500 is separated from the anchor 200.

The inner rod 500 extends through the central hole 225 in the anchor body 200 before coupling with the spreader 300. In one embodiment, the inner rod 500 couples with the spreader 300 through threads on the end of the inner rod 500 and within the proximal end of the spreader 300. In other embodiments, the inner rod 500 may couple to the spreader 300 through other securing mechanisms such as adhesives, welding or frictional fit.

Figure 6:
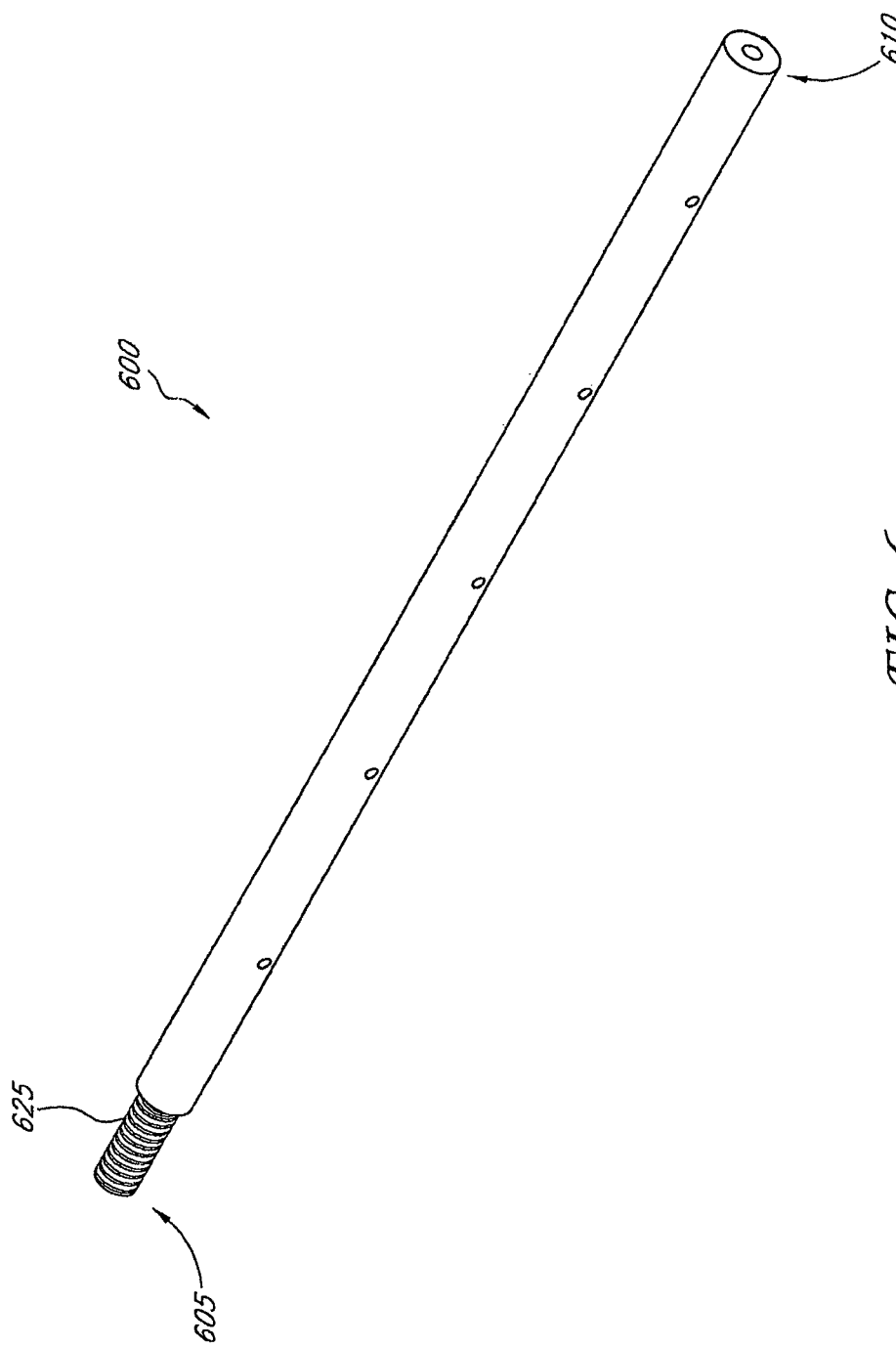
FIG. 6 shows a side view of one embodiment of an outer tube component of an insertion tool.

FIG. 6 shows an embodiment of the outer tube 600. The outer tube 600 is attached at its proximal end 605 to the distal end of handle 700 via threading 625. The distal end 610 of the outer tube 600 is configured such that the inner rod 500 is drawn into the outer tube 600 and through the distal end 610 of outer tube 600 where it is secured to the spreader 300. When the inner tube 500 is advanced far enough that the spreader 300 locks into place or cannot advance anymore, the outer tube 600 distal surface is surface-to-surface with the proximal surface of the anchor body 200. When the inner rod 500 withdraws further into the outer tube upon the continued rotation of the deployment knob and advancement of the actuator shaft, the inner rod 500 strips the threading from the spreader 300 and the inserter tool 400 detaches from the anchor.

Figure 7A:
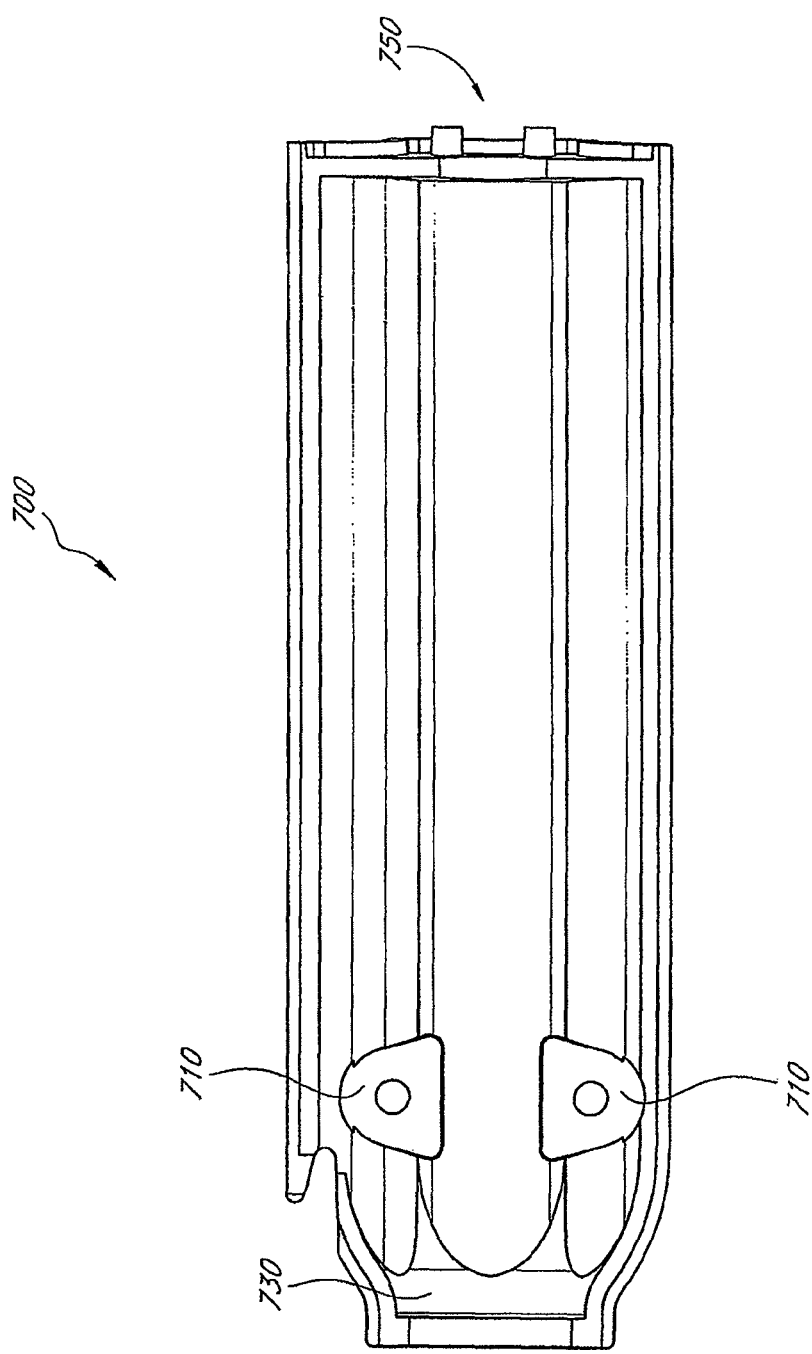
FIG. 7A shows a side view of one embodiment of a handle component of an insertion tool.
Figure 7B:
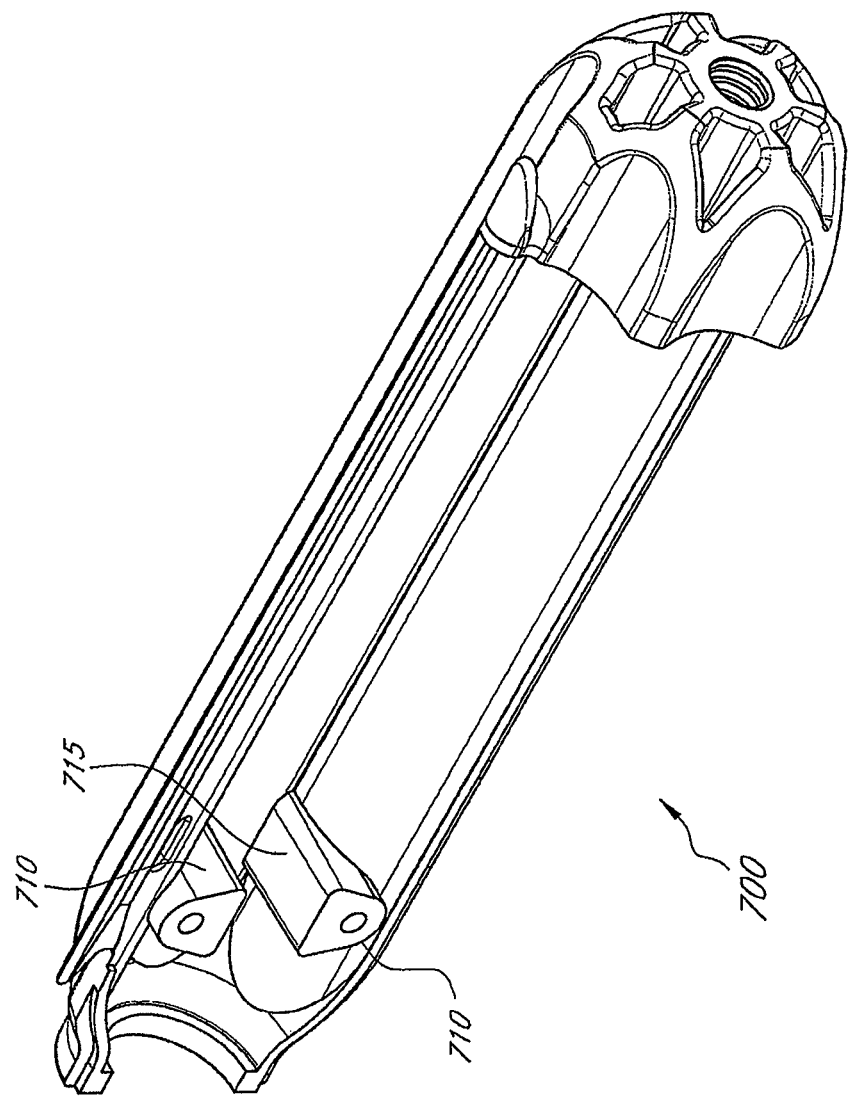
FIG. 7B shows a perspective view of one embodiment of a handle component of an insertion tool.

FIGS. 7A and 7B show embodiments of a handle body 700. FIG. 7A is a cut-away view of the handle body 700. The proximal end of the handle 700 is configured to receive the deployment knob 900 via the ridges 730 which hold the knob 900 secure. The actuator shaft 800 is housed within the handle body 700. A set of flat brackets or braces 710 secure the actuator shaft 800 within the handle 700. The distal end of the handle is configured to receive the outer tube 600 via threads 625 at opening 750. The outer tube 600 is permanently affixed to the handle 700 at its distal end.

FIG. 7B depicts a cross-sectional view of one embodiment of a handle 700. In FIG. 7B the flat surface 715 of the bracket 710 is shown.

Figure 8:
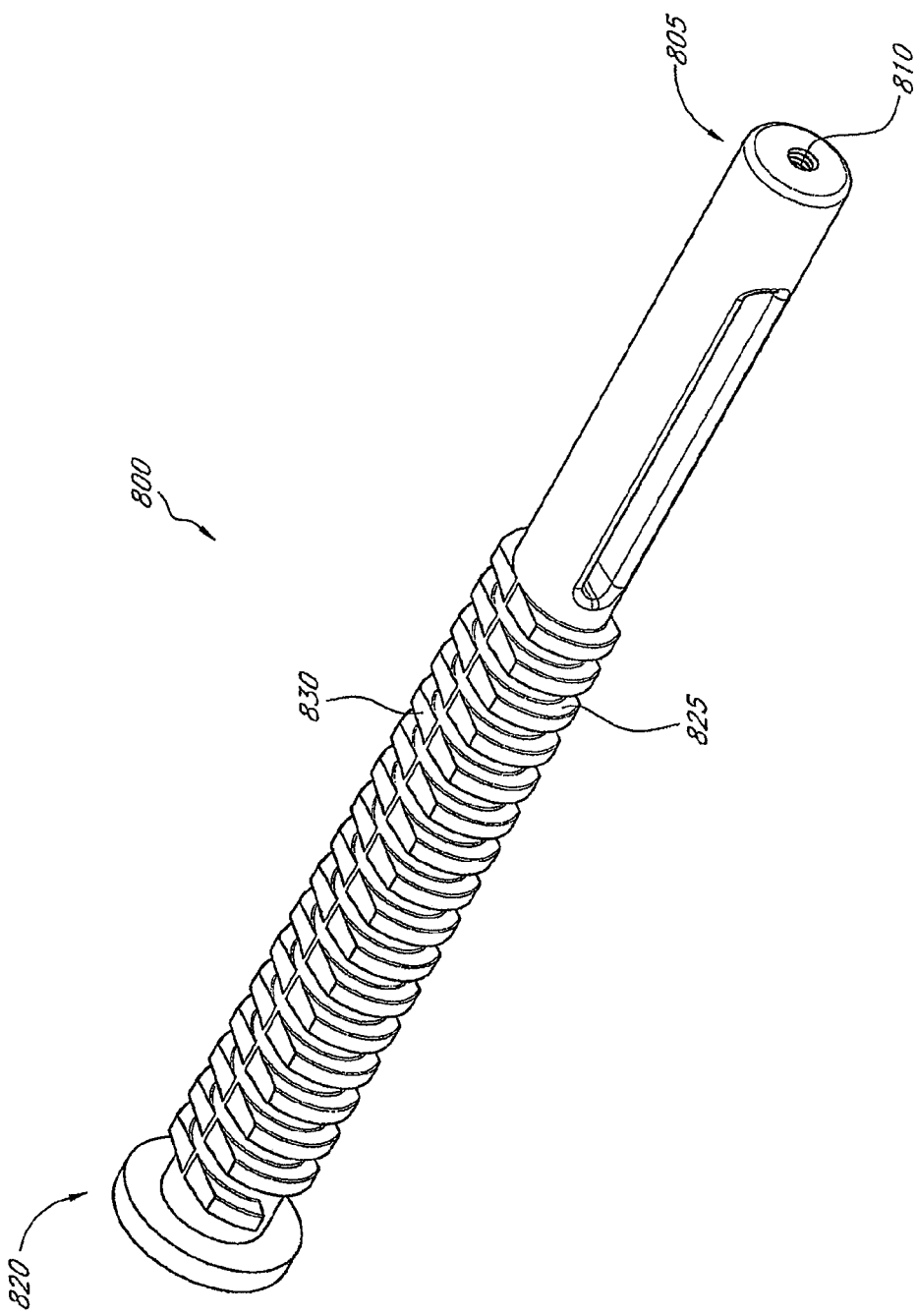
FIG. 8 shows one embodiment of an actuator shaft component of an insertion tool.

FIG. 8 depicts the threaded actuator shaft 800. The actuator shaft 800 is comprised of a distal end 805 comprising a threaded hole 810 which is configured to receive the inner rod 500, a second threaded portion 825 on the body of the shaft configured to advance the inner rod 500, and a proximal end 820 configured to secure within the deployment knob 900. The threading 825 of the actuator 800 has two flat areas 830, one on each side, where there is no threading. These flat areas 830 fit within the flat brackets 710 of the handle such that the actuator 800 cannot rotate within the handle.

The body of the actuator shaft 800 is configured with threading 825 to permit the shaft 800 to advance the inner tube 500. The body of the actuator shaft 800 is not perfectly round, but rather is oval shaped with flat sides 830 that are fit into the handle body 700 in such a way that the actuator shaft 800 cannot itself rotate when the deployment knob 900 is turned and the shaft 800 advances via knob 900. Thus, the threads do not go all the way around the shaft but rather flatten out on the flattened sides of the shaft. The actuator shaft is configured as a coaxial system. That is, the spreader 300, inner tube 500 and actuator 800 are configured to operate as one piece. The flat brackets 710 in the handle make the actuator shaft 800 stay on plane such that the actuator shaft 800 itself cannot rotate within the handle 700. The proximal end of the inner tube 500 couples with the distal end of the actuator shaft 800 via threading.

Figure 9:
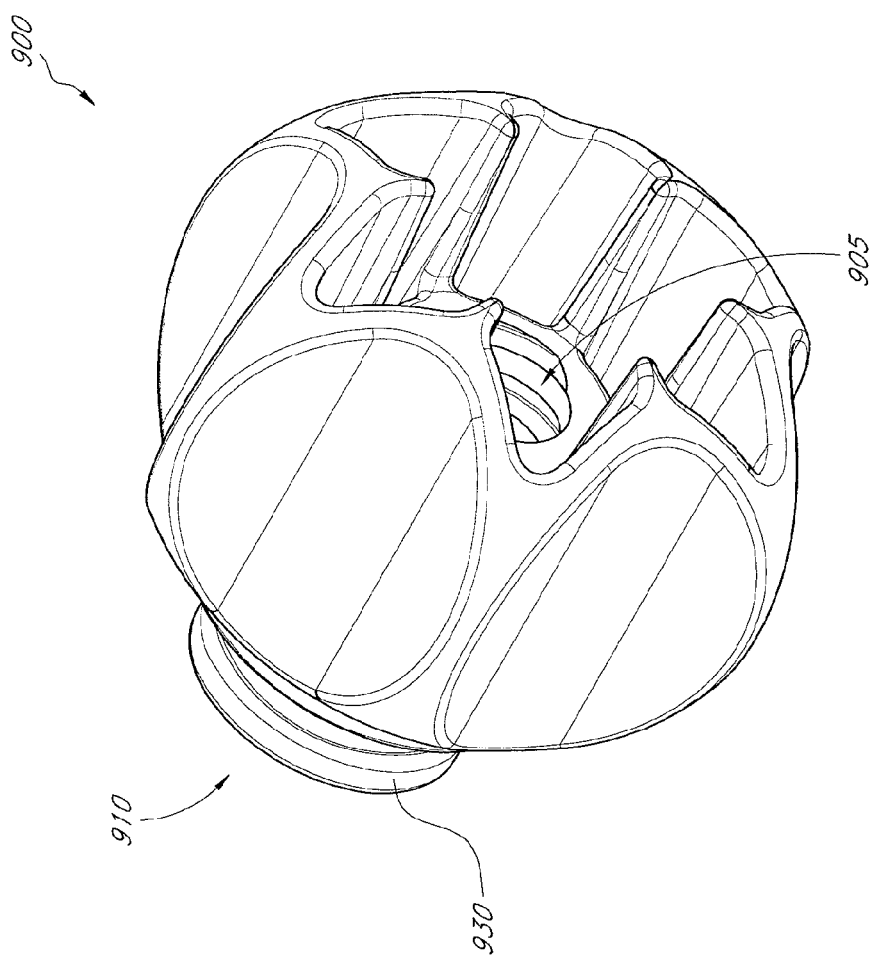
FIG. 9 shows one embodiment of a deployment knob component of an insertion tool.

Moving to FIG. 9, a deployment knob 900 is shown. The deployment knob 900 comprises a central hole 910 which is configured with threading 905, and a groove 930 configured to be received by a corresponding ridge 730 of the handle 700. The threading 905 in the central hole 910 is configured to receive the actuator shaft 800. The deployment knob 900 is configured to advance, relative to the deployment knob 900, the inner rod 500 via the actuator shaft 800. The actuator shaft 800 is joined at its proximal end to the distal end of the deployment knob 900 via threading 905 in the central hole 910. The actuator shaft 800 is attached to the inner rod 500 by way of the proximal end of the inner rod 500 advancing into the distal end of the actuator shaft via threading so that when the deployment knob 900 is rotated, the mechanism of the shaft 800 advances the inner rod 500 proximally such that the spreader 300 is then advanced into the anchor body 200 to expand the anchor body 200 into bone and secure the tissue capture anchor 100.

In one embodiment, the deployment knob 900 is threaded 905 to receive the actuator shaft via the groove 930 of knob 900 fitting with the proximal end ridge 730 of the handle body 700 As the deployment handle is turned, the actuator shaft 800 is advanced in a proximal direction until the anchor body 200 is deployed and locked into place.

Figure 10:
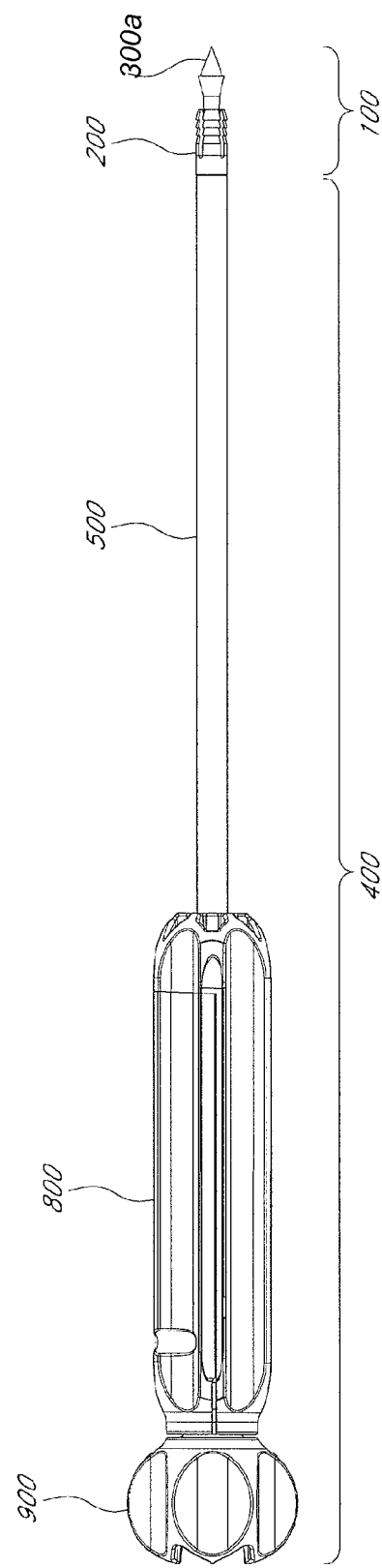
FIG. 10 shows the coupled inserter tool and tissue capture anchor devices in an unexpanded or undeployed state.
Figure 11:
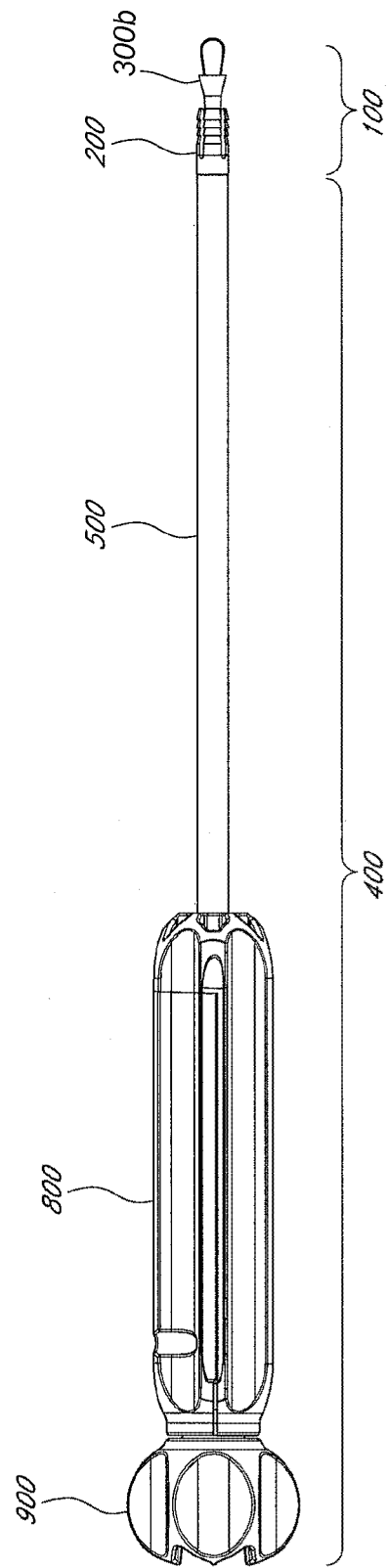
FIG. 11 shows the coupled inserter tool and tissue capture anchor devices in an unexpanded or undeployed state.

FIGS. 10-11 show a tissue capture anchor 100 coupled to the inserter tool 400. The tissue capture anchor 100 comprises the anchor body 200 and the spreader 300. The inserter tool 400, as shown, includes the outer tube 600, the handle 800 and the deployment knob 900. The inner rod 500 is positioned within the outer tube 600, and the outer tube is flush with the anchor body 200. The outer tube 600 may hold the anchor body 200 steady during insertion and deployment. The inner rod 500 extends through the anchor body 200 and couples with the spreader 300 via threading. The spreader 300 is configured to be advanced through the distal end of the anchor body 200 by the inner rod 500 via a rotating the deployment knob 900.

In another embodiment, the inner rod 500 extends through the spreader 300 which is configured such that the central hole 325 extends through the spreader tip 305. The inner rod 500 is configured with a sharp, pointed tip such that the tip of the inner rod 500 spears or captures tissue to secure into the bone hole before the anchor body 200 is fully deployed.

The inner rod 500 provides the mechanism to draw the spreader 300 into the central hole 225 in the anchor body 200 to fully expand the anchor body 200. During deployment of the tissue capture anchor 100, the inner rod 500 is continually advanced via a screwing motion until the spreader locks with the anchor body. As the deployment knob 900 continues to turn and the inner rod 500 continues to pull on the threads of the spreader 300, the inner rod 500 strips the threads from the inside of the spreader 300 and the insertion tool 400 releases from the anchor body 200. Any thread shavings are contained within the outer tube 600.

Figure 12:
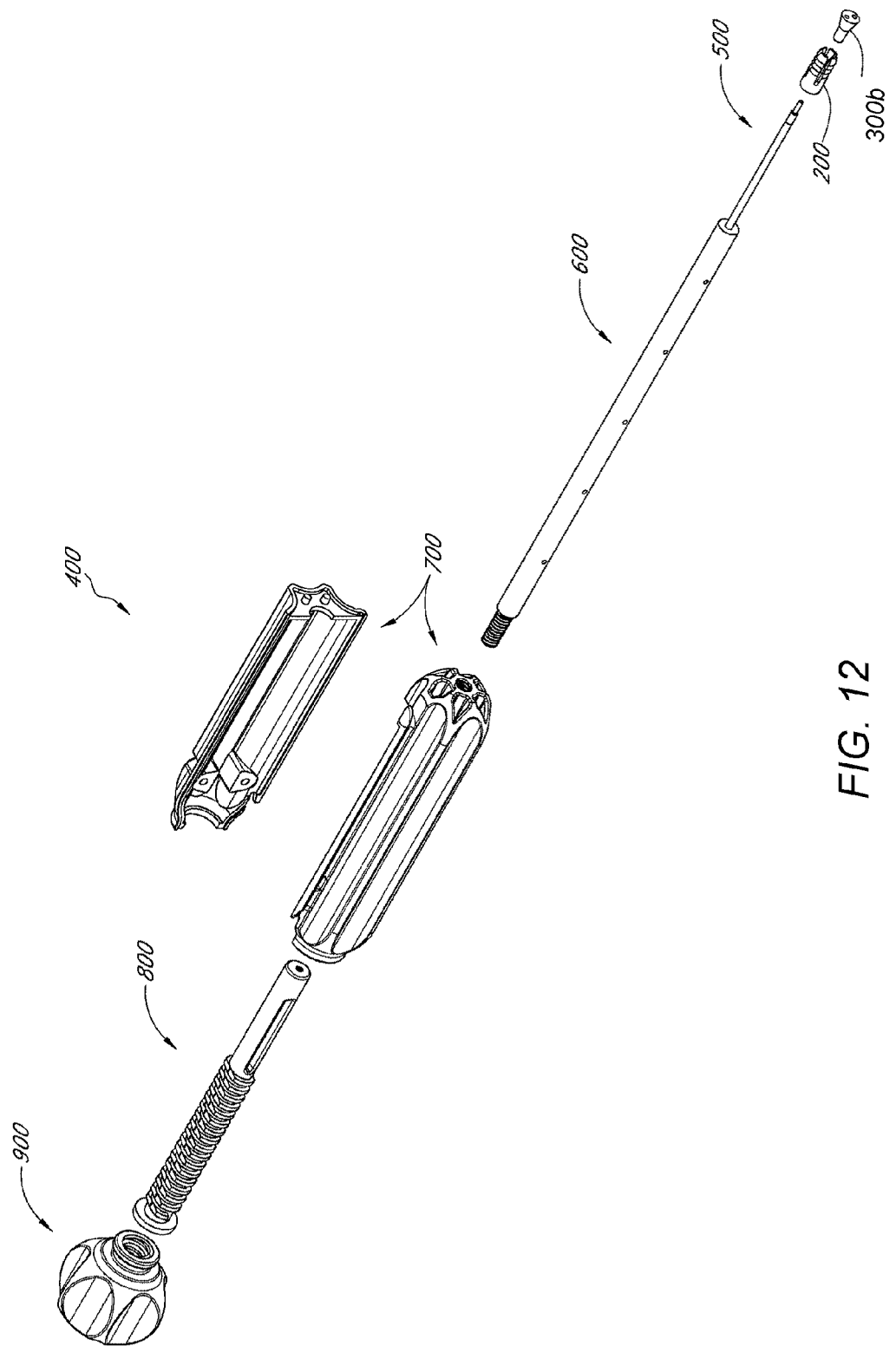
FIG. 12 shows the coupled inserter tool and tissue capture anchor devices in an unexpanded or undeployed state.

FIG. 12 illustrates an exploded view of the anchor 100 and the inserter 400. The tissue capture anchor 100 comprises the anchor body 200 and the spreader 300. The inserter tool 400, as shown, includes the outer tube 600, the handle 800 and the deployment knob 900. The inner rod 500 is positioned within the outer tube 600, and the outer tube is flush with the anchor body 200. The outer tube 600 may hold the anchor body 200 steady during insertion and deployment. The inner rod 500 extends through the anchor body 200 and couples with the spreader 300 via threading. The spreader 300 is configured to be advanced through the distal end of the anchor body 200 by the inner rod 500 via a rotating the deployment knob 900.

The inner rod 500 provides the mechanism to draw the spreader 300 into the central hole 225 in the anchor body 200 to fully expand the anchor body 200. During deployment of the tissue capture anchor 100, the inner rod 500 is continually advanced via a screwing motion until the spreader locks with the anchor body. As the deployment knob 900 continues to turn and the inner rod 500 continues to pull on the threads of the spreader 300, the inner rod 500 strips the threads from the inside of the spreader 300 and the insertion tool 400 releases from the anchor body 200. Any thread shavings are contained within the outer tube 600. Once the anchor is deployed, the sutures are then removed via pulling them free or else cut at the top of the anchor.

In some embodiments, a pre-attached delivery handle is provided. In some embodiments, the insertion tool or delivery handle is disposable. In other embodiments, the insertion tool can be sterilized, reloaded and reused.

Those of skill in the art will appreciate other inserters and mechanisms that may be used to insert and deploy the tissue capture anchor 100 described herein.

Although a particular inserter device for inserting and manipulating tissue capture anchor 100 has been described, it should be understood that other inserter designs may be used for manipulating the parts of tissue capture anchor 100 described above to insert the anchor into bone and tissue to the bone. For example, it may be possible to use separate tools for inserting the anchor and deploying the anchor.

It will be appreciated that there are numerous combinations of anchors and their placement that may be used to secure soft tissue to bone by the methods and devices described herein. These variations as well as variations in the design of the above described anchor devices and inserter devices are within the scope of the present disclosure.

Tissue Capture Anchor with Flat Sides and Suture Loop

In another embodiment, anchors as described herein are used for anterior cruciate ligament (ACL) repair. In one embodiment, a femoral tunnel is drilled in the femur. One or two bundles of tendon are then fed through the suture loop 1390 of the spreader 1300. The anchor 1000 is then inserted into the bone and deployed as discussed below.

Figure 13A:
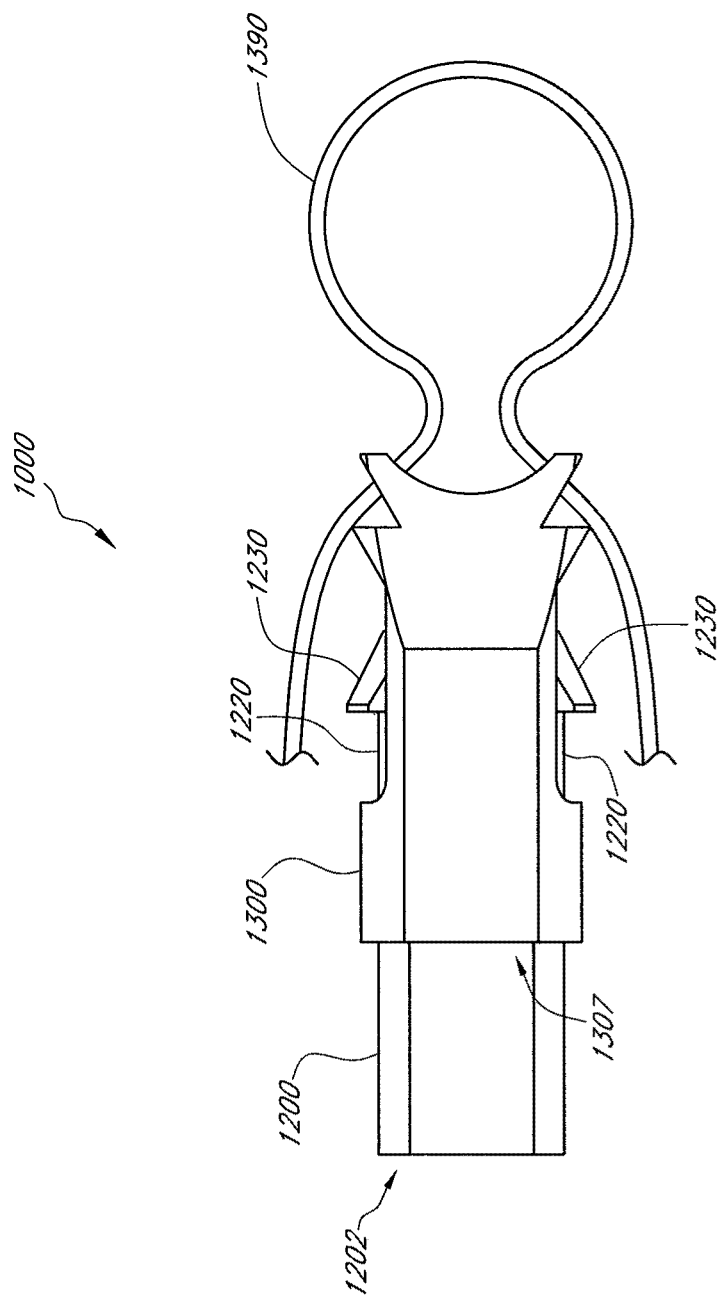
FIG. 13A shows a side view of one embodiment of a tissue capture anchor in an undeployed or unexpanded state.

In various embodiments, soft tissue may be attached to bone utilizing one or more tissue capture anchors. In one non-limiting example, depicted in FIGS. 13A-13E, a suture loop is coupled to the distal end of the anchor. FIG. 13A depicts a side view of a tissue capture anchor 1000 comprising an anchor body 1200, a spreader 1300, and a suture loop 1390. The anchor body 1200 is comprised of tines 1220 and one or more teeth 1230. The tines 1220 expand from the distal end of the anchor body 1200 when the spreader 1300 is engaged with the anchor body 1200. The proximal end of the spreader 1300 is configured to fit around the outside of the proximal end 1202 of the anchor body 1200. In FIG. 13A, the tissue capture anchor 1000 is in the undeployed, or unexpanded position.

Figure 13B:
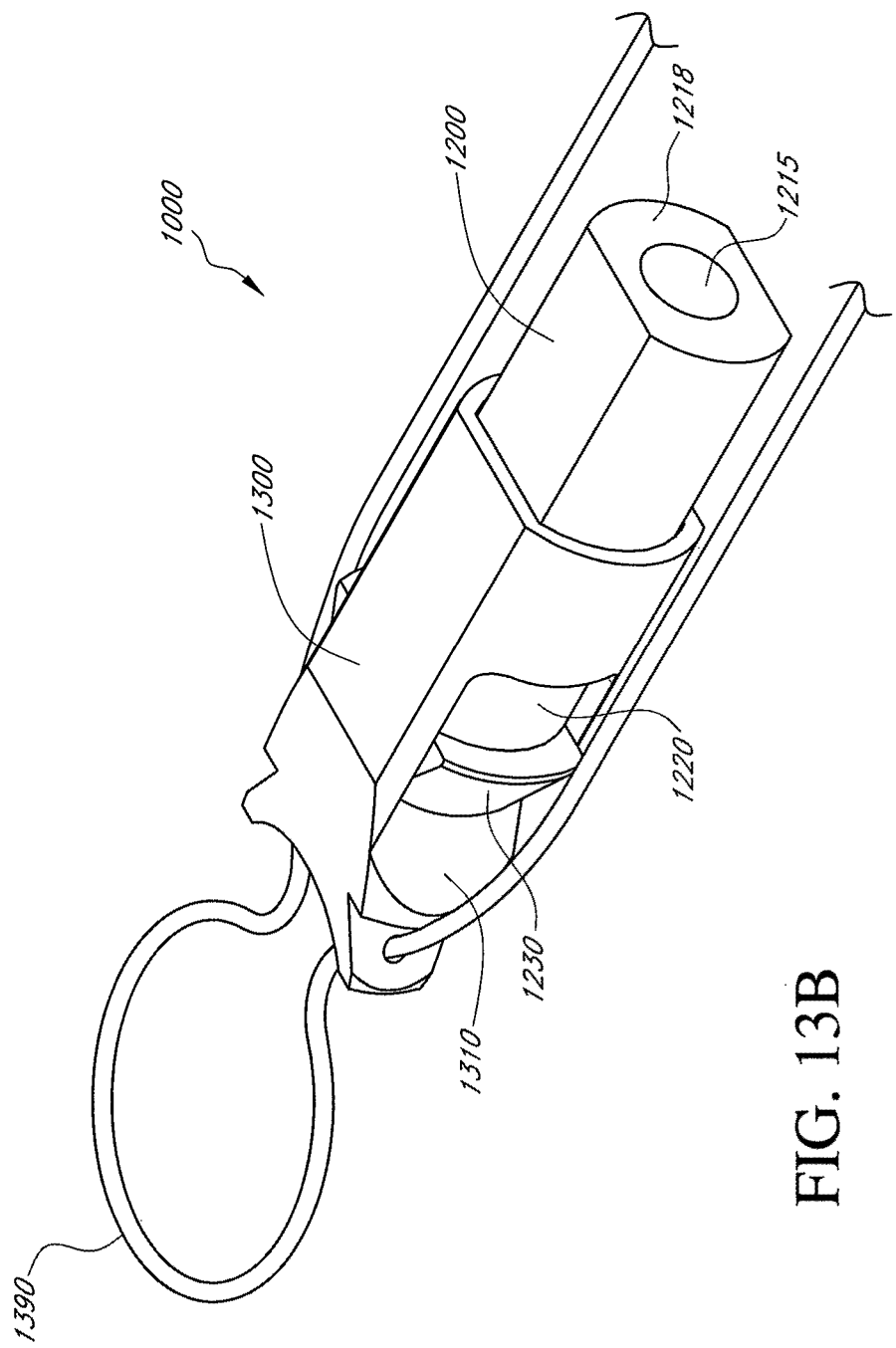
FIG. 13B shows a perspective view of one embodiment of an undeployed tissue capture anchor.

FIG. 13B shows a perspective view of the unexpanded tissue capture anchor 1000. In this embodiment, the anchor body 1200 is slightly inserted in the central hole 1215 at the proximal end of the spreader 1300.

Figure 13C:
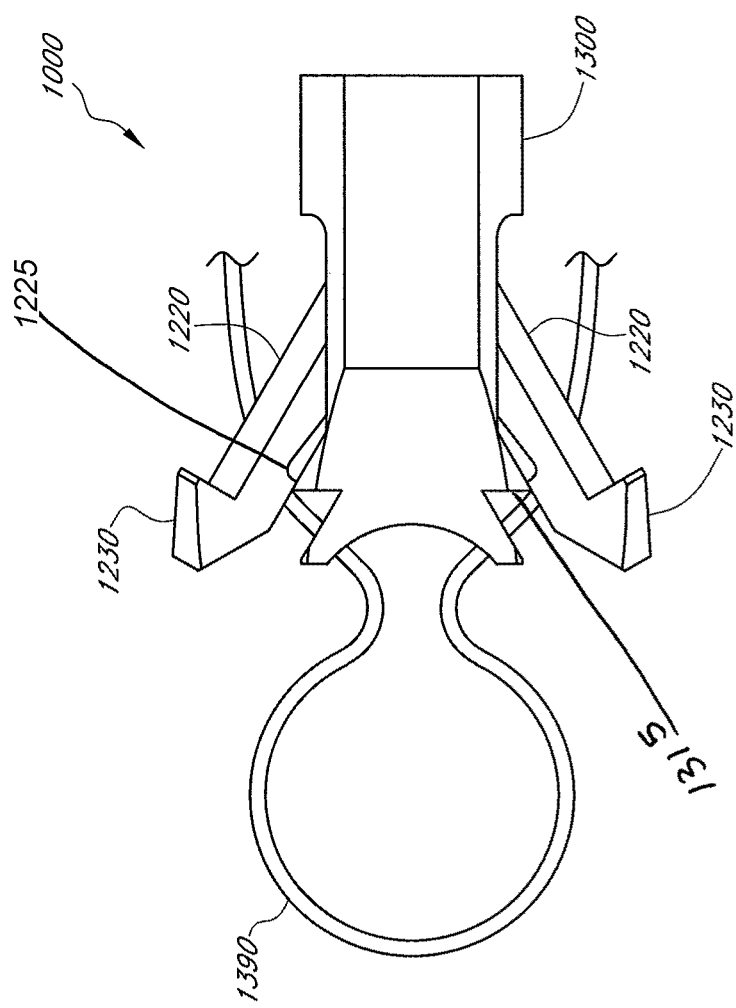
FIG. 13C shows a side view of one embodiment of a tissue capture anchor in the deployed or expanded state.

FIG. 13C shows a side view of the tissue capture anchor 1000 in the deployed or expanded position. In the deployed or expanded position, the spreader 1300 has been drawn up in between the tine 1220 causing them to expand from the distal end of the anchor body 1200 through openings in the spreader 1300. When deployed, the one or more teeth 1230 engage with the bone surface trapping tissue between the bone and the bone anchor 1000.

The distal end of the anchor body 1200 may comprise a grooved surface 1225 to engage with the ridge 1325 of the spreader 1300 to lock the spreader 1300 into place when the anchor body 1200 is fully deployed. The grooved surface 1225 is oriented such that the distal end of the spreader 1300 can be easily moved in the proximal direction in between the tines 1230. The spreader 1300 fits over the proximal end of the anchor body 1200, via the central hole 1315 of the spreader 1300 with the ridge 1325 snapping into the groove 1225 as the distal end of the spreader 1300 is moved proximally. However, when the ridge 1325 is snapped into groove 1225, proximal movement of distal end is inhibited. In some embodiments, the groove 1225 can exist at different locations of the surface of the central hole or else even along substantially the entire surface of the central hole 1215. In some embodiments the anchor body 1200 may be coupled to the spreader 1300 in several positions. In other words, in one embodiment the spreader 300 need not be inserted over the anchor body 1200 as far as it will go for it to be secured to the anchor body 1200.

It will be appreciated that other shapes are also contemplated, including multiple concentric grooves, a series of protruding ridges, or any other suitable structure that permits an anchor 1200 to be securely locked within the central hole of the spreader 1300.

Figure 13D:
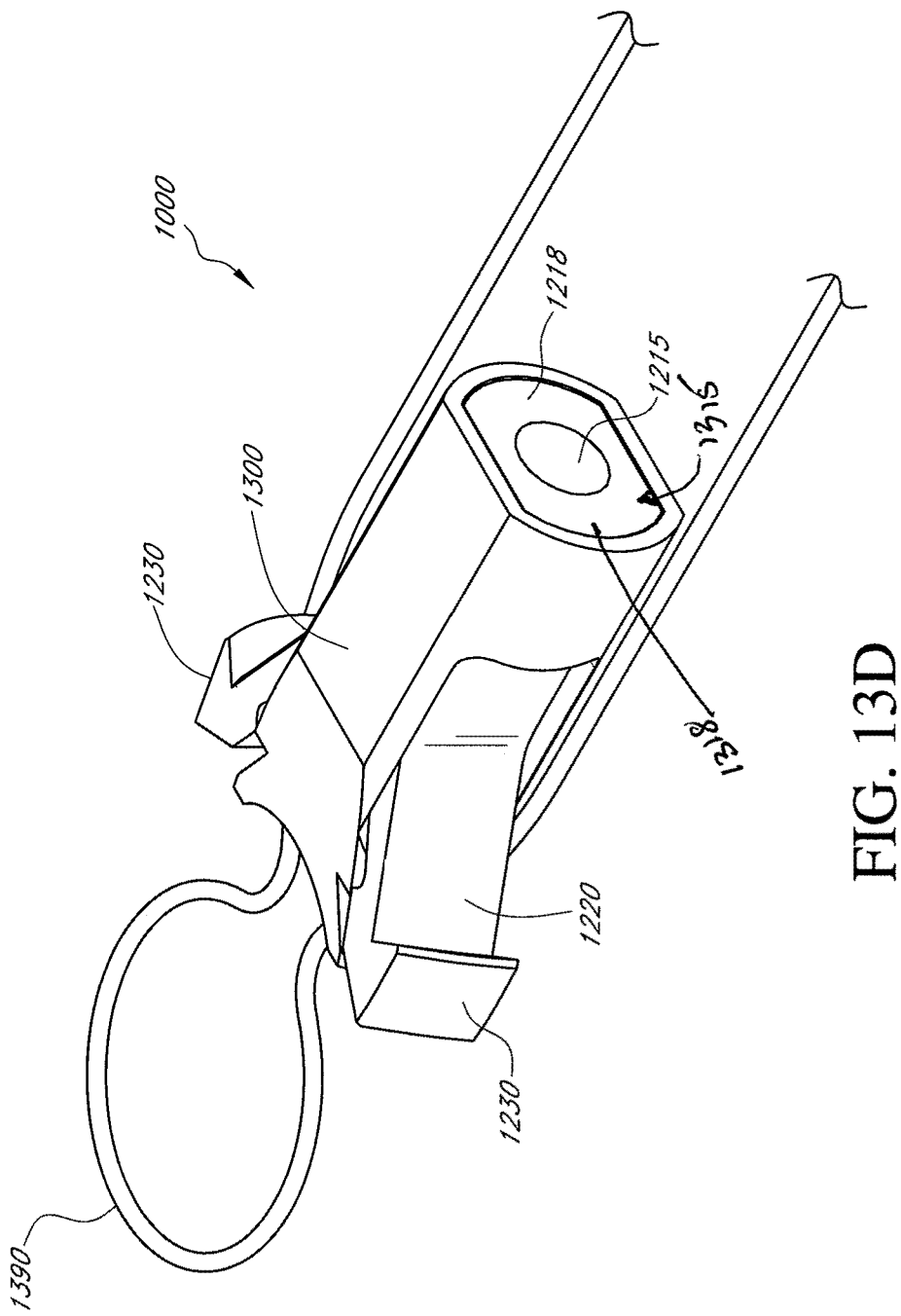
FIG. 13D shows a perspective view of one embodiment of a tissue capture anchor in the deployed or expanded state.

With reference to FIG. 13D, which is a perspective view of the top and side of anchor body 1200 engaged with the spreader 1300, the top (proximal end) of the spreader 1300 comprises a hole 1315 in the center for receiving the anchor body 1200. In some embodiments, the top surface 1318 of the spreader 1300 may be textured such as with a scallop shape or grooves so as to inhibit movement of an insertion tool against the surface of the spreader.

During deployment, the spreader 1300 is drawn proximally in between the tines 1230 causing them to expand from the distal end of the anchor body 1200. Also during deployment, the spreader 1300 is drawn proximally until the ridge 1325 of the spreader 1300 passes a groove 1225 in the anchor body 1200. When the spreader passes this point, the ridge 1325 and groove 1225 engage or click and the spreader 1300 is locked into place and the anchor body 1200 cannot undeploy or reverse and the spreader 1300 cannot reverse direction.

Figure 13E:
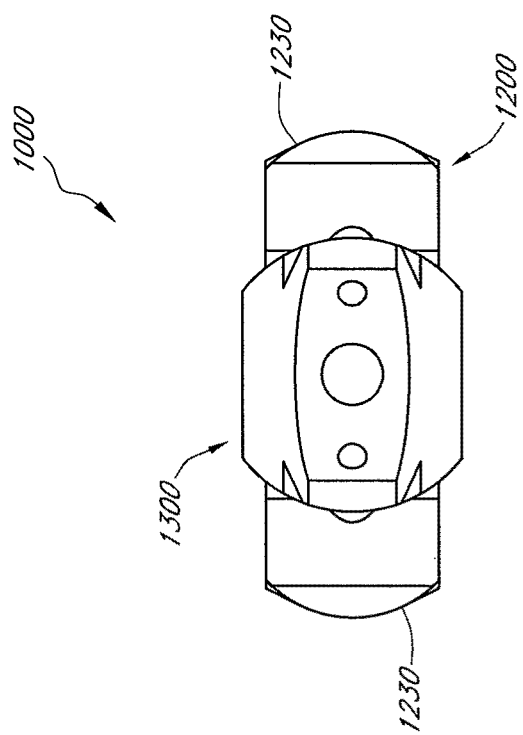
FIG. 13E shows another perspective view of one embodiment of a tissue capture anchor in the deployed or expanded state.

FIG. 13E shows a distal end view of the tissue capture anchor 1000. In this view the anchor body 1200 is fully deployed. The spreader 1300 is securely fixed between the tines 1230 and the ridge 1325 and groove 1225 of the anchor body 1200 will keep the spreader 1300 from being uninserted or reversed from the anchor body 1200. The tines 1220 are fully expanded. Since the teeth 1230 are facing the opposite direction from the view of FIG. 13E, only their edges are visible along the edges of the tines 1220.

Figure 14A:
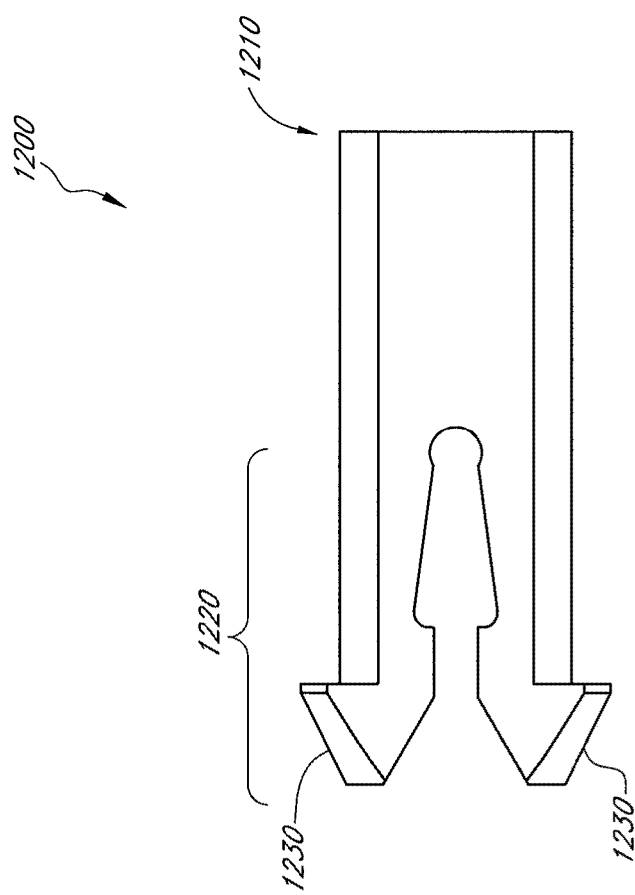
FIG. 14A depicts a side view of one embodiment of an anchor body.
Figure 14B:
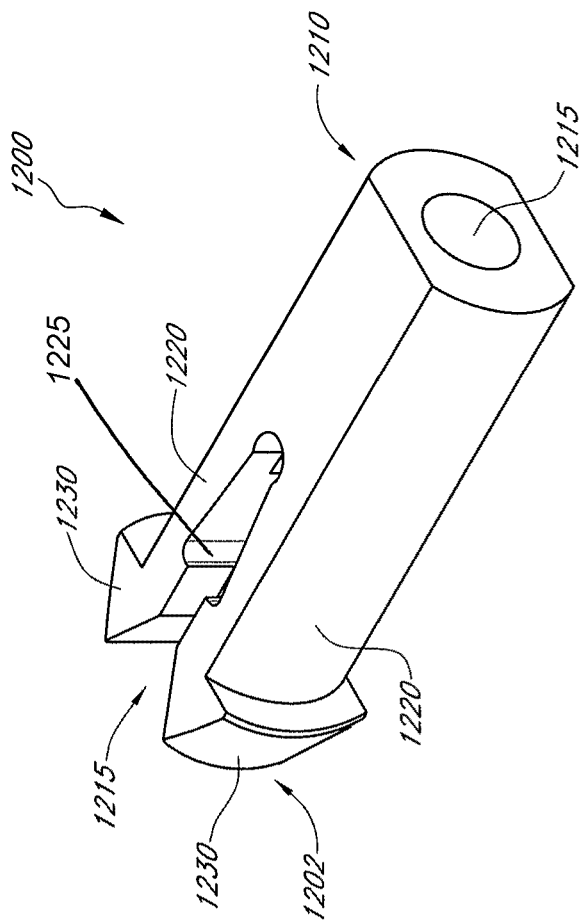
FIG. 14B depicts a perspective view of one embodiment of an anchor body.
Figure 14C:
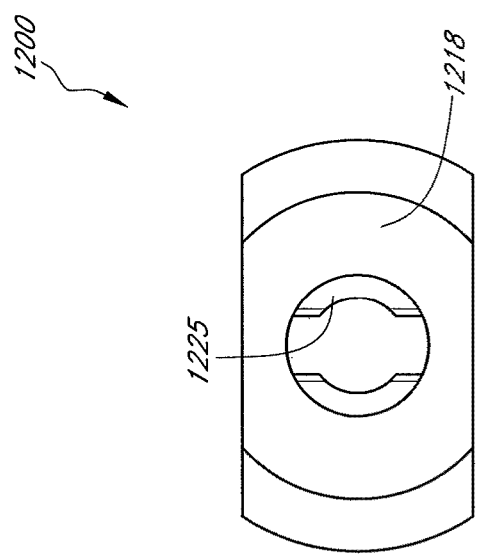
FIG. 14C depicts another perspective proximal view of one embodiment of an anchor body.
Figure 14D:
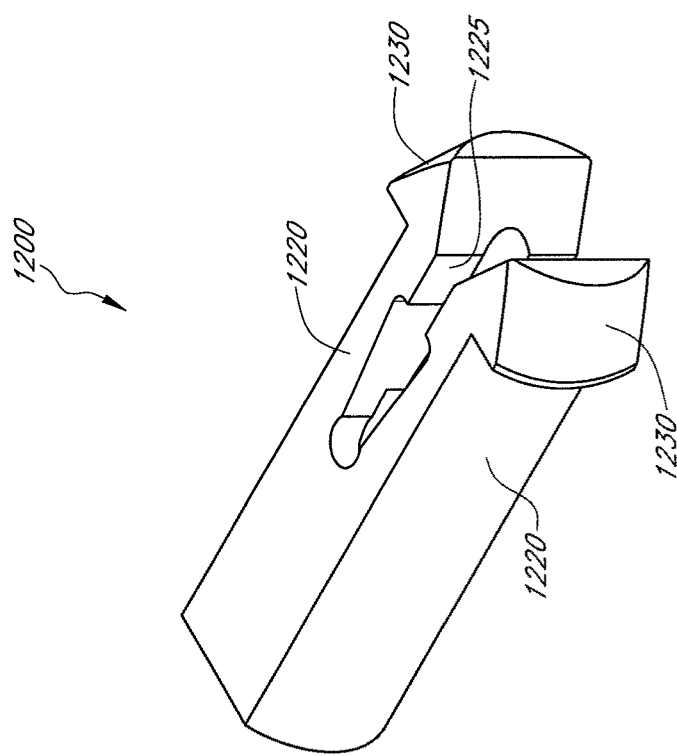
FIG. 14D depicts a perspective distal view of one embodiment of an anchor body.

FIGS. 14A-14D depict an embodiment of an undeployed anchor body 1200. FIG. 14A depicts a side view of the anchor body 1200. FIG. 14B depicts a perspective view of an embodiment of the anchor body 1200. FIG. 14C depicts a view from the proximal end, or base, of the anchor body 1200, and FIG. 14D depicts a perspective view from the distal end, or tines, of the anchor body 1200. The proximal end of the undeployed anchor body 1200 is generally comprised of a slightly rectangular shaped structure which is flat on at least two sides. The anchor body 1200 tapers distally into at least two tines. The anchor body 1200 generally comprises a shape complementary with the spreader, with flat sides and with a diameter larger than distal end 1202. In some embodiments, the proximal end of the anchor body is rounded. In other embodiments, the proximal end of the anchor body is rectangular. With reference to FIGS. 14B-14D, a hole 1215 may advantageously be provided in the center of proximal end 1210. With reference to FIG. 14B, the bottom of distal end 1202 includes two tines 1200, or projections which originate from about half to a third of the way distally from the proximal end of the bone anchor 1200. At the point where the tines begin to project from the proximal end of the anchor body, is the other end of hole 1215. Central hole 1215 comprises a central opening that extends through the anchor body 1200. In some embodiments the anchor body 1200 comprises a groove 1225 in its inner surface, as shown in FIGS. 14C-14D. Thus, the inner surface of the anchor body 1200 is not flat. In some embodiments, some or all of these surfaces may be textured such as with a scallop shape or grooves so as to inhibit movement of the wedge portion 1399 of spreader 1300 once it is withdrawn into the anchor body. In some embodiments, texturing in the outer surfaces of anchor body 1200 matches texturing in the inner surfaces of the spreader 1300. It will be appreciated that the illustrated embodiments represent only one possibility; thus, other shapes for the surface of proximal end 1210 may also be used.

During assembly, the distal end 1202 of the anchor body 1200 is configured to be received within the proximal end of spreader 1300. Hole 1215 in anchor body 1200 is an opening into a central ("axial") bore into and through the proximal end of the anchor body 1200.

The sides of the tines 1220 preferably include a groove for engaging with the spreader 1300. It will be appreciated that other methods of securing the wedge portion 1399 of the spreader 1300 within the anchor body 1200 may be used, such as a frictional fit or threading.

The anchor body 1200 is comprised of one or more tines 1220 which spread outwardly when engaged with the spreader 1200. In one embodiment shown in these figures, there are two tines. The tines 1220 engage with the bone, fixedly securing the anchor body 1200 in the bone. The tines comprise a number of teeth 1230 which further engage with the tissue and bone in the deployed tissue capture anchor 1000. The number of tines 1220 and teeth 1230 can vary. In one embodiment, there are two tines 1200 with one tooth 1230 per tine 1220. The proximal end 1210 of the anchor body 1200 is configured to receive an inserter component, which is inserted through the hole 1215 in the center of the anchor body 1200 and is coupled with a spreader 1300. In one embodiment, the spreader is attached and deployed as disclosed above.

Figure 15A:
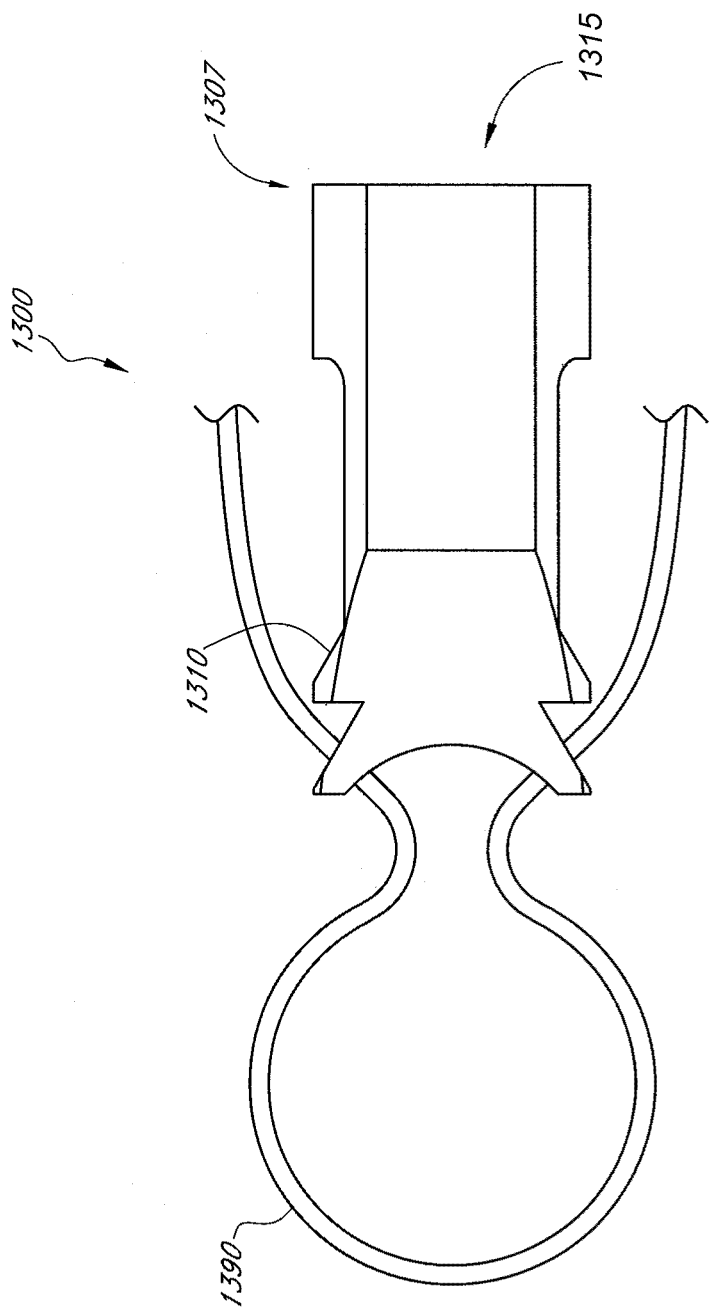
FIG. 15A depicts a side view of one embodiment of a spreader.
Figure 15B:
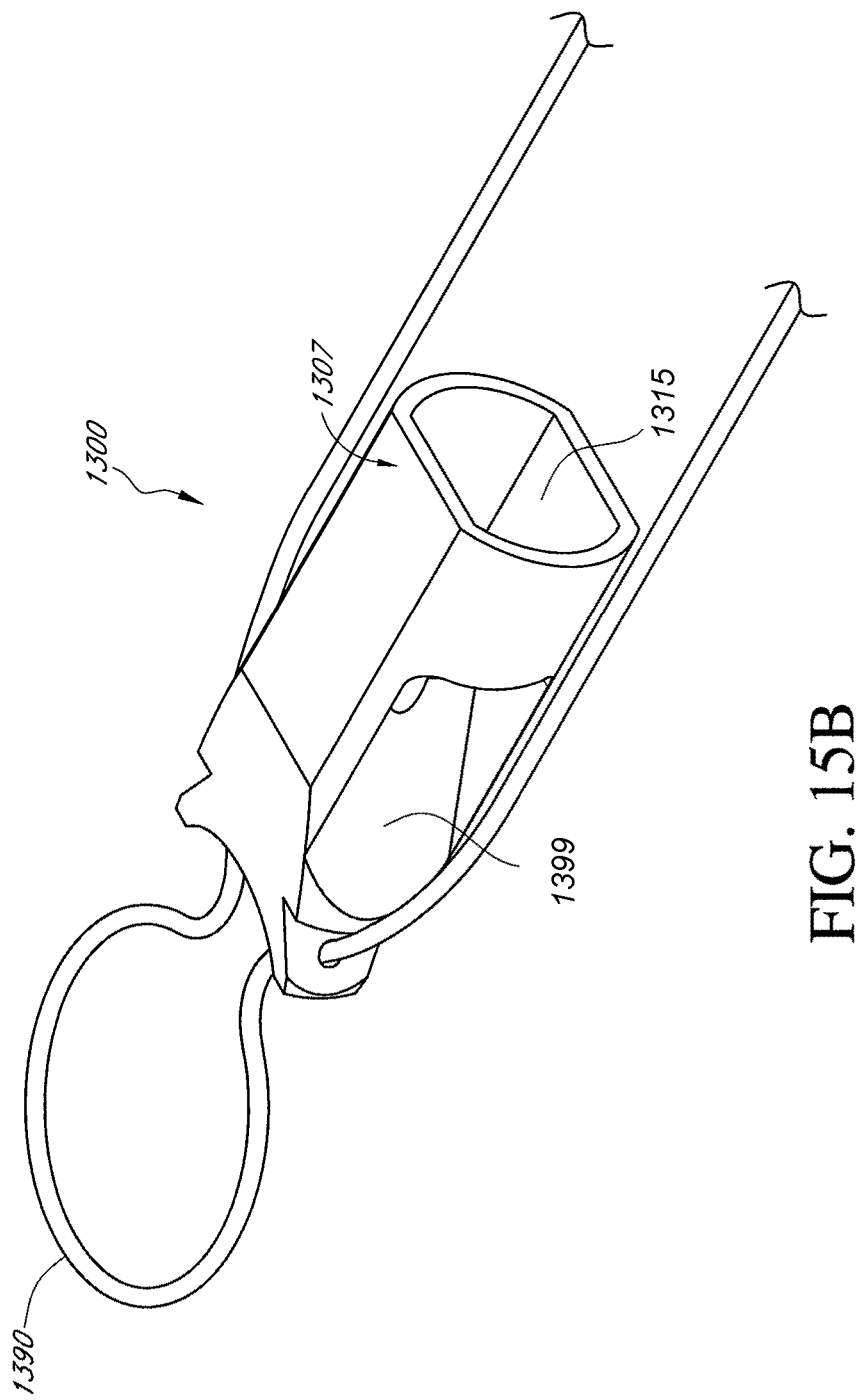
FIG. 15B depicts a perspective view of one embodiment of a spreader.
Figure 15C:
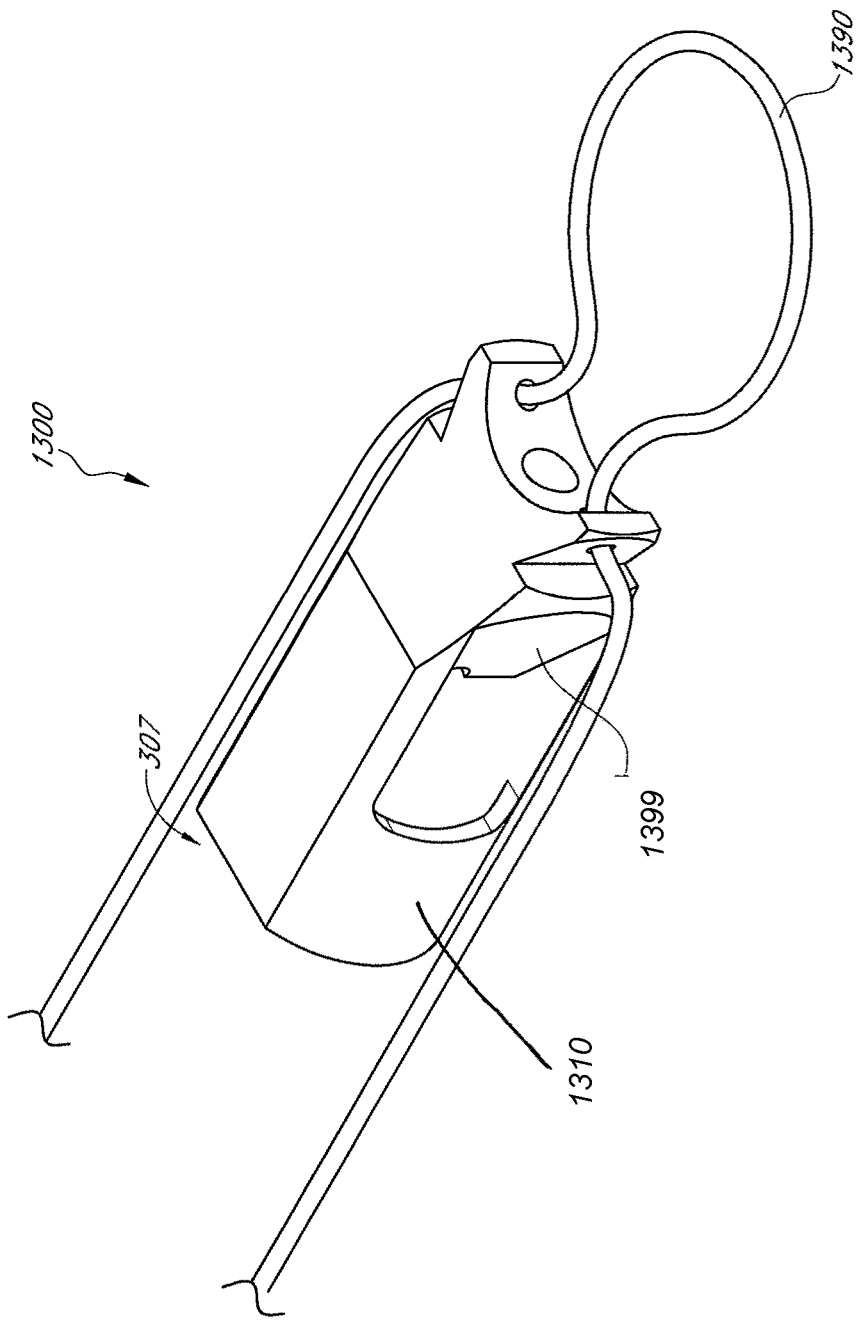
FIG. 15C depicts a side view of an alternative embodiment of a spreader comprising a through-hole.

FIG. 15A shows a side view of an embodiment of the spreader 1300. FIG. 15B shows a perspective view of the spreader 1300. The spreader 1300 comprises a generally inwardly curved face at distal end 1317 and a proximal end 1307 comprising an axial bore 1315 for receiving an insertion tool 400, a central body 1310, a triangular-shaped expander portion 1399, and a ridge 1325. The distal end 1302 further comprises two holes 1305a and 1305b for receiving a suture loop 1390. The proximal end of the wedge 1399 is configured for coupling with an inserter. In one embodiment, the inserter used is as described above. For instance, in this embodiment, the proximal end 1307 of the spreader 1300 comprises a hole 1315 that receives the inserter tool for coupling.

The distal end 1302 of the spreader 1300 may advantageously be tapered to facilitate insertion of the spreader 1300 into bone.

The spreader 1300 further comprises central body 1310 which gradually narrows from the proximal end The distal portion of the spreader forms a ridge (or groove) 1325 just proximal to the curved face at distal end 1317. The distal end 1302 of spreader 1300 comprises axial bores 1305a and 1305b for receiving sutures 1390 and axial bore 1315 which optionally receives an insertion tool. The distal end comprises a rounded area 1317 for securing tissue in place. The proximal end 1307 is configured for coupling with an anchor body 1200 and optionally receives an inserter. For instance, in this embodiment, the proximal end 1307 of the spreader 1300 comprises a hole 1315 that receives the anchor body 1200. In one embodiment, sutures 1390 are received into one of holes 1305a and 1305b from a location exterior to the inserter, looped, threaded into the other of holes 1305a and 1305b and returned along the exterior of the insertion tool to the proximal end of the insertion tool where the surgeon can secure the sutures 1390.

The spreader 1300 comprises a proximal section comprising a hole for receiving the bone anchor 1200. The spreader 1300 comprises a distal section which further comprises a wedge 1399 at the interior distal end of the spreader. This distal portion of the spreader including the wedge-shaped portion 1399 is configured to fit between the tines 1220 of the anchor and advance the tines outward as the insertion tool deploys the anchor 1000.

In one embodiment, a loop of suture is secured through the axial bores 1305a and 1305b from a location exterior to the insertion tool such that a loop of suture extends from the spreader for use in a surgical procedure. The distal end of the spreader 1300 comprises two openings 1305a, 1305b through which the suture loop 1390 extends. The resulting length of suture extends from the proximal end of the inserter tool 400 to the distal end where the suture 1390 is threaded through hole 1305a forms a loop, and then back through 1305b and extending once again to the proximal end of the insertion tool. The suture loop 1390 extending through the distal end of the spreader 1300 is freely slidable, for example, such that it can be moved or adjusted back through the holes 1305a and 130b. In one alternate embodiment, the axial bore 1315 may be used to receive sutures.

The spreader 1300 is configured to be drawn in between the tines 1220 via an insertion tool. As the tissue capture anchor 1000 is deployed, the spreader 1300 is advanced, such that the wedge shaped portion 1399 of spreader 1300 is advanced between the tines 1220 of the distal end of anchor body 1200, spreading the tines 1220 of the anchor body 1200 until the ridge 1325 of the spreader 1300 engages the groove 1225 in the inside of the anchor body 1200 at which point it locks into place. In one embodiment, the ridge 1325 is undercut 1322 providing even more security for reversing.

As discussed above, the tines 1220 in the anchor may be in a low-profile streamlined position prior to insertion into bone. A spreader 1300 is used after insertion to expand the tines 1220 such that their one or more teeth 1225 engage bone. The wedge portion 1399 of the spreader 1300 may comprise any suitable shape configured to be inserted through the axial bore 1215 in the anchor body 1200 and make contact with the tines 1220. The wedge portion 1399 of the spreader 1300 may be at least partially positioned within the axial bore of the bone anchor prior to tine expansion as depicted in FIG. 13B. As the spreader 1300 is moved from a first lower position to a second upper position, the proximal end of the wedge 1399 of spreader 1300 is designed to spread or force the tines 1220 from a first low-profile position (for example, an internal lateral position) to a second external lateral position. In one embodiment, the proximal end of the spreader 1300 may have ridges to assist in preventing slippage or mis-alignment.

The spreader 1300 will remain in a locked position with the anchor body 1200 with the tines 1220 in their fully spread position. The force provided by the tines' 1220 expansion and compression interaction with the bone walls keeps the spreader 1300 tightly engaged. Further protection against slipping or tilting of the spreader 1300 is provided by the optionally ridged sides of the spreader 1300. In one embodiment, the spreader 1300 may have ridges or indentations to assist in a tight fit such that accidental slipping or adjustments are minimized. In one embodiment, one or more of the tines 1220 have an indentation on a side facing the central axis of the anchor. A ridge on the spreader can then engage the indentation, thereby stabilizing the spreader 1300 and preventing the spreader 1300 from being advanced too far into the anchor. In an alternative embodiment, the spreader comprises an indentation (for example, an indentation in a ridge on the spreader 1300) that can engage with a protrusion on a side of a tine facing the central axis of the anchor. In addition, to stabilizing the spreader 1300 and preventing over insertion, this feature also prevents rotation of the spreader 1300 relative to the anchor.

In this embodiment, tissue is captured by the anchor by threading one or more tissue bundles (for example, single or double bundles of tendon) through the suture loop 1390. The suture loop is secured around the tendon such that the tendon is secured to or within the curved portion 1317 of the spreader 1300. When the anchor with threaded tissue bundles is inserted into bone, the tissue is held into place at the distal end of the spreader and will be held secure against the sides of the bone hole and further secured by the expanded tines, as described herein, along the sides of the anchor, and back out of the bone. In these embodiments, tissue may be captured by only threading through the suture loop 1390

In the preferred embodiment, the tissue capture anchor 1000 is made entirely of a biocompatible engineering plastic such as polyether-ether-ketone (PEEK). Other embodiments include a tissue capture anchor entirely or in part of a non-metallic substance that is biocompatible. Biocompatible materials such as poly ether ketone (PEK), polyetherimide (ULTEM), ultrahigh molecular weight polyethylene (UHMPE), polyphenylene, or some other engineering polymer materials known to those of skill in the art may be used. A non-metallic anchor system may provide certain advantages such as, for example, eliminating MRI artifacts.

The inserter tool shown in FIG. 4 depicts individual components of an inserter tool used in conjunction with the anchor 1000. The inserter tool comprises an inner rod or tube 500, an outer tube 600, a handle body 700, a threaded actuator shaft 800, and a deployment knob 900. In some embodiments, the inserter 400 is coupled to the tissue capture anchor 1000 during manufacturing. In a preferred embodiment, the inserter tool is disposable.

The inserter tool 400 is designed to insert and manipulate a tissue capture anchor such the tissue capture anchor 1000 described in FIG. 13A and FIG. 13B. In some embodiments, the tissue capture anchor 1000 is manufactured to be attached to the inserter tool before packaging. In other embodiments, the tissue capture anchor is coupled to the inserter tool prior to insertion. In a basic configuration, the inserter tool is assembled as follows: the inserter tool 400 is configured such that the inner rod 500 is disposed within the outer tube 600. The outer tube is configured to fit against the proximal end of the anchor body 1300. The inner rod 500 extends through outer tube 600 and is configured to attach to the spreader 300 via threading within the hole in the spreader 300 and threading on the distal end of the inner rod 500. The proximal end of the outer tube 600 is connected to a handle 700 and the inner rod 500 extends through the proximal end of the outer tube 600 and screws into the threaded actuator shaft 800. The actuator shaft 800 extends just past the proximal end of the handle 700 where it is configured to secure with a deployment knob 900. Suture 390 is threaded through the around the cleat in the handle and is permitted to freely extend down the exterior of the outer tube to the distal end of the spreader where it is threaded through holes 1305a and 1305b forming a loop and extending back up the length of the outer tube to the proximal end of the inserter tool. In some embodiments, the suture 1390 is wound around the cleat on the handle.

The individual components of the inserter tool are described above, and illustrated in FIGS. 5-9.

Figure 16A:
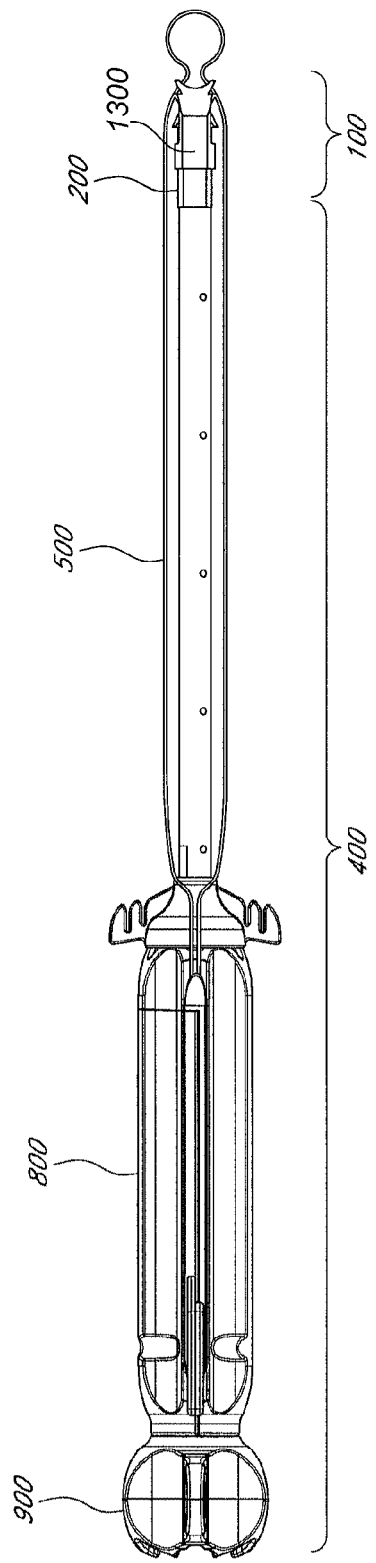
FIGS. 16A and 16B show exploded views of one embodiment of an inserter tool.
Figure 16B:
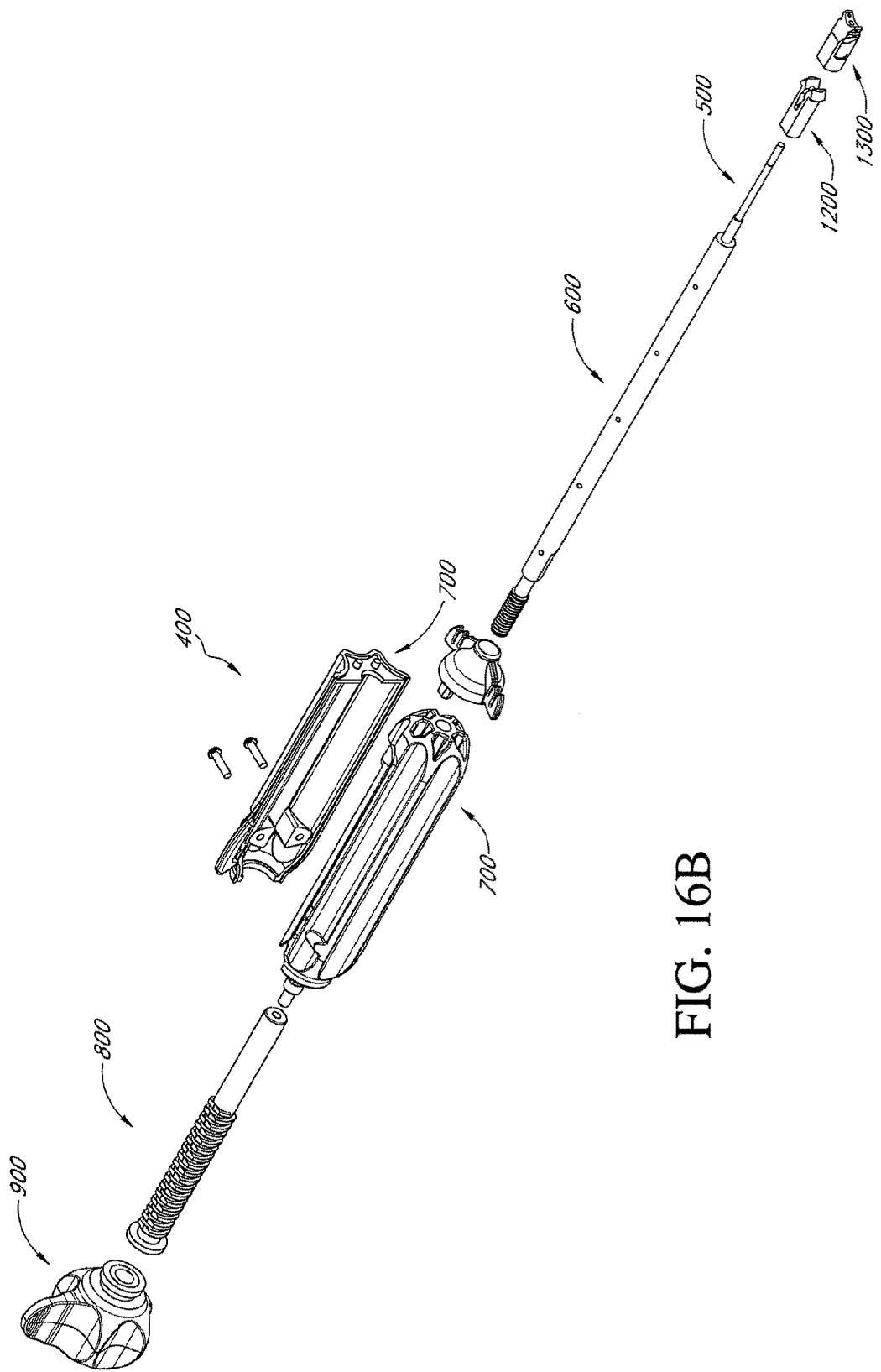

FIG. 16A shows an exploded view of the tissue capture anchor and the inserter. FIG. 16B shows a tissue capture anchor 1000 coupled to the inserter tool 400. The tissue capture anchor 1000 comprises the anchor body 1200 and the spreader 1300. The inserter tool 400, as shown, includes the outer tube 600, the handle 800 and the deployment knob 900. The inner rod 500 is positioned within the outer tube 600, and the outer tube is flush with the anchor body 1200. The outer tube 600 may hold the anchor body 1200 steady during insertion and deployment. The inner rod 500 extends through the anchor body 1200 and couples with the spreader 1300 via threading. The spreader 1300 is configured to be advanced through the distal end of the anchor body 1200 by the inner rod 500 via rotating the deployment knob 900.

The inner rod 500 provides the mechanism to draw the spreader 1300 into the central hole 1225 in the anchor body 1200 to fully expand the anchor body 1200. During deployment of the tissue capture anchor 1000, the inner rod 500 is continually advanced via a screwing motion until the spreader locks with the anchor body. As the deployment knob 900 continues to turn and the inner rod 500 continues to pull on the threads of the spreader 1300, the inner rod 500 strips the threads from the inside of the spreader 1300 and the insertion tool 400 releases from the anchor body 1200. Any thread shavings are contained within the outer tube 600.

In some embodiments, a pre-attached delivery handle is provided. In some embodiments, the insertion tool or delivery handle is disposable. In other embodiments, the insertion tool can be sterilized, reloaded and reused.

Those of skill in the art will appreciate other inserters and mechanisms that may be used to insert and deploy the tissue capture anchors 100 and 1000 described herein.

Although a particular inserter device for inserting and manipulating tissue capture anchors 100 and 1000 have been described, it should be understood that other inserter designs may be used for manipulating the parts of tissue capture anchors 100 and 1000 described above to insert the anchor into bone and tissue to the bone. For example, it may be possible to use separate tools for inserting the anchor and securing tissue capture anchor.

It will be appreciated that there are numerous combinations of anchors and their placement that may be used to secure soft tissue to bone by the methods and devices described herein. These variations as well as variations in the design of the above described anchor devices and inserter devices are within the scope of the present disclosure.

Methods of Attaching Soft Tissue to Bone

Various embodiments include methods for attaching soft tissue to bone. In some embodiments, the methods include using the tissue capture anchors described above. In one preferred embodiment, a biceps tenodesis procedure is performed arthroscopically.

The biceps tendon connects the biceps muscle to the bone. The biceps tendon connects the biceps muscle to the bone. The tendon passes from the muscle to the shoulder joint. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

A biceps tenodesis is often, but not always, performed in patients with significant biceps tendon symptoms, and evidence at the time of arthroscopy of biceps tendon inflammation or tears.

The procedure using a tissue capture anchor described herein merely requires drilling the bone hole and capturing the tendon with the anchor and dragging the tendon into the bone hole. In some embodiments, a further advantage when using an awl to make the bone hole is that the whole procedure can be percutaneous.

Figure 17:
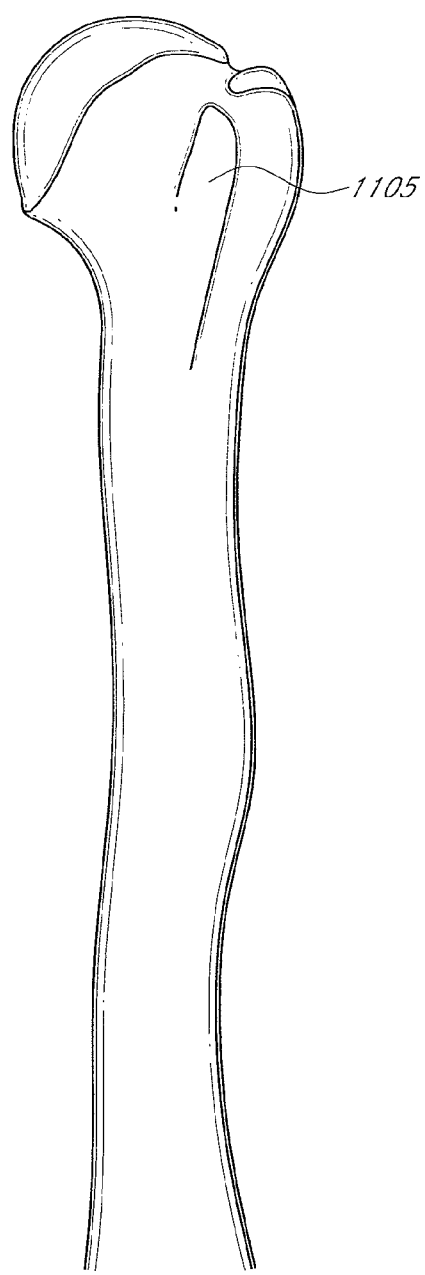
FIG. 17 shows the bicipital groove of the shoulder.
Figure 18:
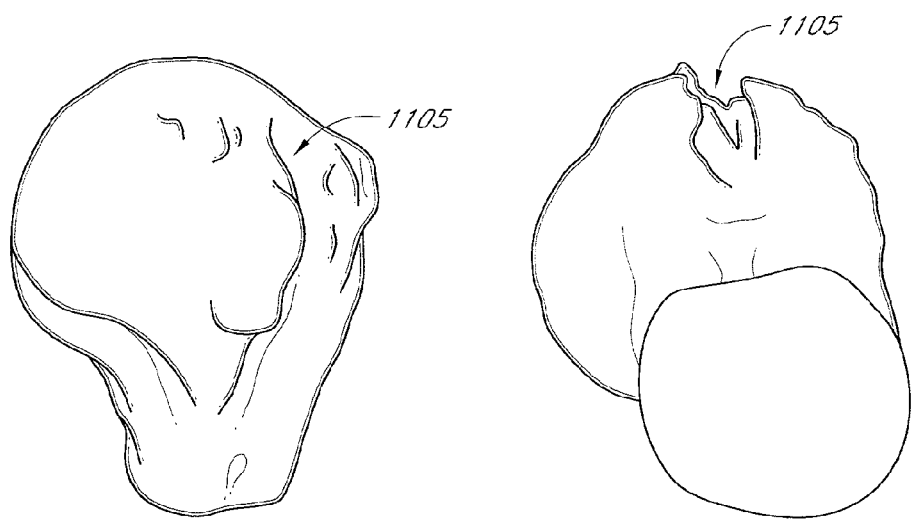
FIG. 18 illustrates another example of the bicipital groove of the shoulder

In a preferred method, the procedure is performed arthroscopically. A percutaneous approach may be used in the alternative. In one embodiment, a 6 mm PEEK tissue capture anchor is used, although different sizes and materials may be used. In some instances the hole into which the tissue capture anchor will be inserted is made by making a clearance hole for the anchor in the superior portion of the bicipital groove 1105 using a drill bit or suitably sized awl. In one embodiment, the hole is made by the spreader 300 tip after the spreader 300 captures the tissue to be secured. The hole may also be made in any other suitable position depending on pathology of the tendon, etc. FIGS. 17 and 18 show different views of the bicipital groove and surrounding bone of the shoulder and biceps. The bicipital groove is a furrow on the upper part of the humerus occupied by the long head of the biceps and is also called the intertubercular groove. In some embodiments a 7 mm drill bit is used; however in other embodiments, a different sized drill bit can be used. In one embodiment, the clearance hole can range from 5 mm wide to 9 mm wide. In other embodiments, the size of the clearance hole will vary, as the size depends on the size of the anchor. Depending on the softness of the bone and the size of the anchor, the hole can be from 8 mm-22 mm deep. For example, in one embodiment, a 6 mm tissue capture anchor is used, and for soft bone, the hole can be at least 11 mm deep. For average bone, the hole can be approximately 10-12 mm deep. For very soft bone, the hole can be approximately 20 mm.

Figure 19:
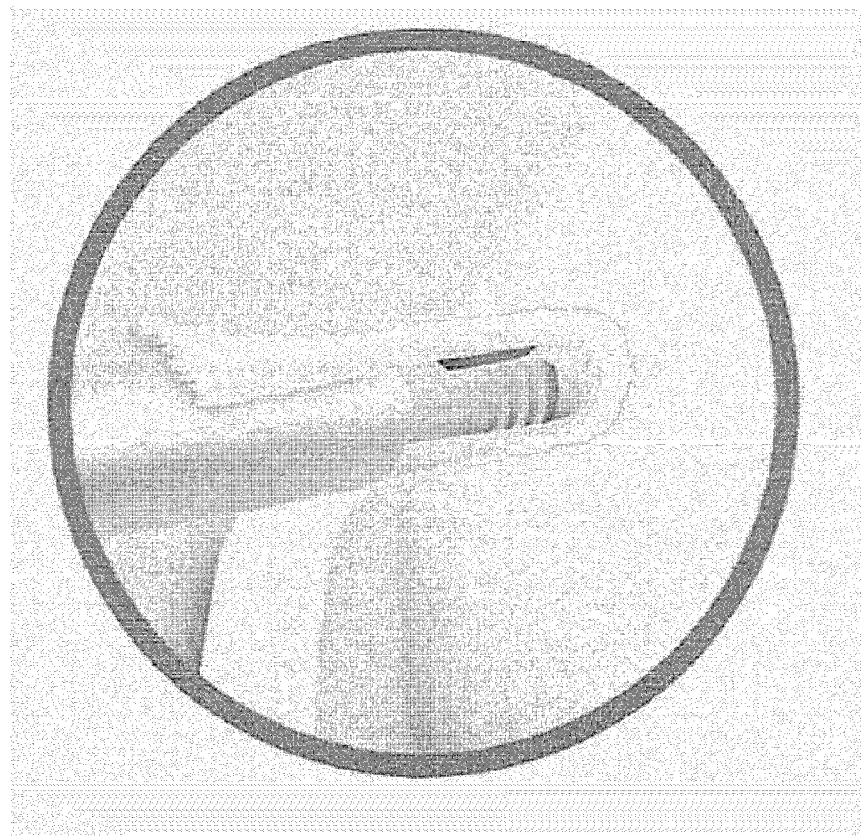
FIG. 19 illustrates one embodiment of an undeployed anchor inserted in a bone hole.
Figure 20:
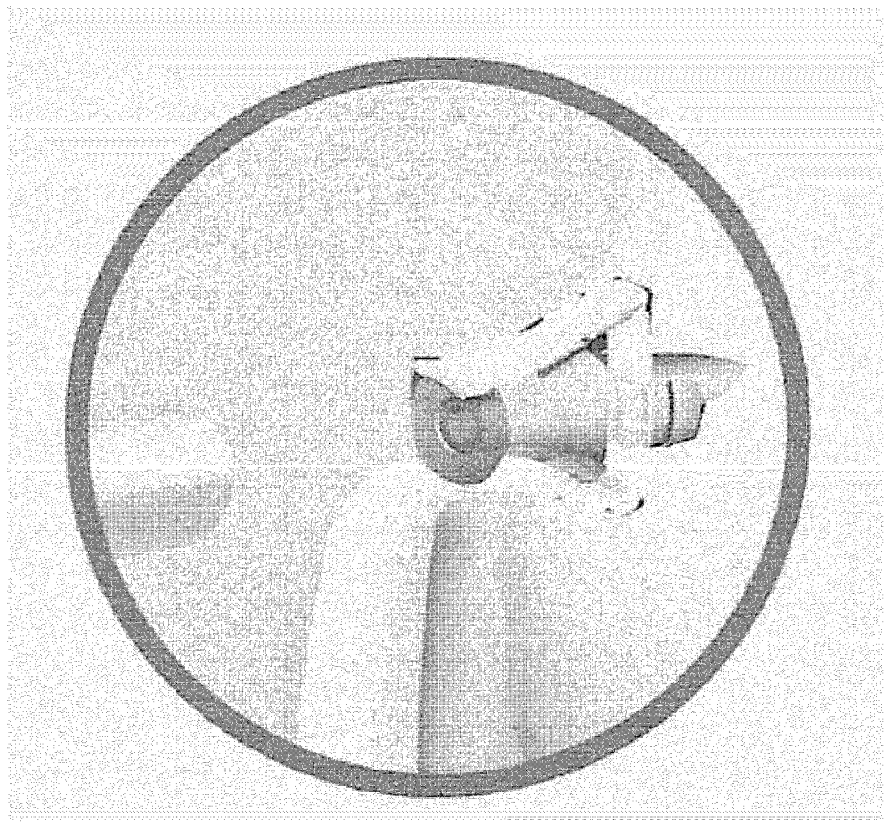
FIG. 20 illustrates one embodiment of a deployed anchor inserted in a bone hole.
Figure 21:
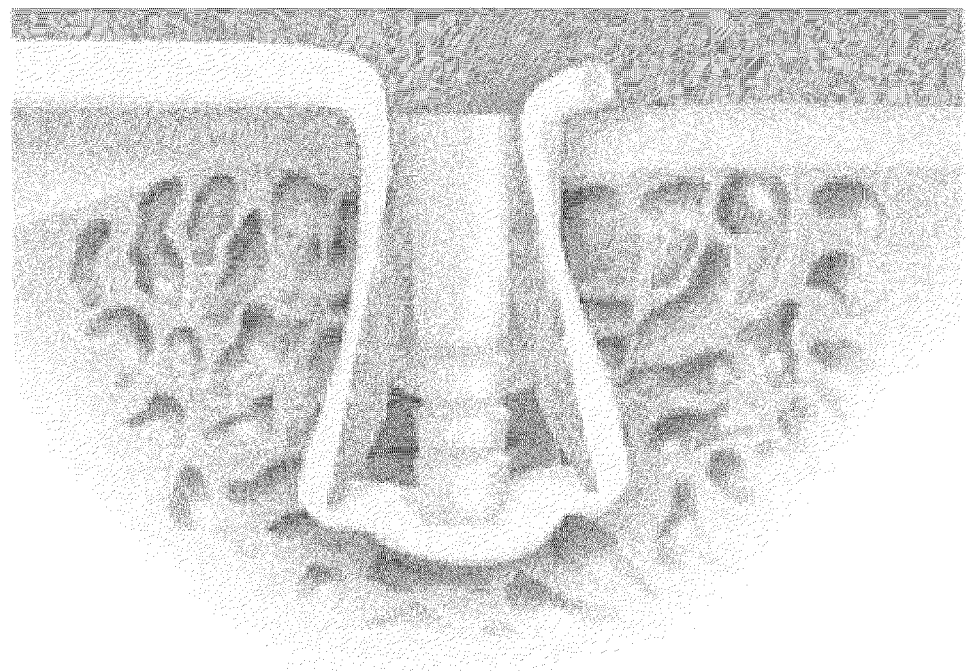
FIG. 21 illustrates one embodiment of a deployed bone anchor.

The implantation site is cleared of any soft tissue in the region of the bone hole using a bur or other suitable means. When the hole in the bone is pre-drilled, the hole is advantageously drilled with a diameter smaller than the diameter of anchor body 200 and spreader 300 so that the tines can engage the bone through the sides of the hole. Angled protrusions or teeth may be used that provide greater resistance to removal of the anchor body 200 than to insertion. As shown in FIG. 19, the tendon will then be captured by the anchor and forced into the clearance hole and the anchor deployed as shown in FIG. 20. As shown in FIG. 21, the tendon is essentially folded around the anchor longitudinally resulting in a double surface contact. As described above, the tendon may be captured using a variety of methods including spearing with the anchor of FIG. 1A, threading tissue through the through-hole in the anchor of FIG. 3C, and threading tissue through the suture loop in the anchors of FIGS. 1G and 13C.

In one nonlimiting embodiment, the shoulder preparation is as that used by Richards and Bruthkhart ("A Biomechanical Analysis of Two Biceps Tesodesis Fixation Techniques" Arthoscopy. The Journal OF Arthroscopic and Related Surgery Vol 21, No 7 (July), 2005: pp 861-866) which is incorporated by herein by reference in its entirety. The shoulder will undergo soft tissue dissection to the level of the rotator cuff. At this point, the surpraspinatus tendon insertion is reflected by sharp dissection and the long head biceps tendon inspected for any evidence of pathology. The tendon of the LHB is then sharply incised, freeing from its intra-articular origin at the superior aspect of the glenoid as well as dividing it as the musculotendinous junction so that the biceps tendon is a free segment. In other embodiments, other methods of shoulder preparation are used.

Repairs are complete by drilling a clearance hole for the anchor in the superior portion of the bicipital groove using a standard drill bit. As shown in FIGS. 19-21, the tendon will then be captured by the anchor and forced in to the clearance hole and the anchor placed to capture the tendon. The tendon will be essentially folded around the anchor longitudinally, resulting in a double surface contact. The proximal surface of the anchor will be situated flush with the cortical surface.

In another embodiment, anchors as described below are used for anterior cruciate ligament (ACL) repair. In this embodiment, a femoral tunnel is drilled in the bone. One or two bundles of hamstring tendon are captured by the anchor. The anchor is then inserted into the bone and deployed as discussed above. As described above, the tendon may be captured using a variety of methods including spearing with the anchor of FIG. 1A, threading tissue through the through-hole in the anchor of FIG. 3C, and threading tissue through the suture loop in the anchors of FIGS. 1G and 13C.

The bone anchor is made of any acceptable material. In one embodiment, the anchor is made of PEEK. The procedure using the PEEK tissue capture anchor merely requires drilling the bone hole and "capturing" the tendon within the suture loop of the anchor, dragging the tendon into the bone hole. In some embodiments, the tendon is captured using a spear tip. In one embodiment, the suture loop is used to capture and secure the tendon. In some embodiments, a further advantage when using an awl to make the bone hole is that the whole procedure can be percutaneous.

In one embodiment, a hole is drilled in to the bone at a diameter of about 9 mm. The anchor is positioned such that a grasper tool can be implemented to grasp a tendon through the suture loop and secure the suture around the tendon. The tendon can then be manipulated and moved or positioned. In one embodiment, a double bundle of tendons is inserted into a single bone tunnel in the femur. In one embodiment, a gracilis and a semitendinosus tendon are both doubled over for insertion into the bone hole. The anchor, which, in one embodiment may be about 8 mm or 9 mm in diameter, is inserted into the bone hole with the doubled over tendons. Due to the size of the hole, the anchor, which may be 8 or 9 mm in diameter is inserted with the doubled over tendons draped over its tip into the hole. The anchor is also suited for single bundle single tunnel and single bundle double tunnel procedures. In other embodiments, the bone hole and the anchor can be difference sizes as needed.

In one embodiment, the surgeon drills through the tibia and up into the femur and loads the anchor plus tendons through the tibial tunnel. In one embodiment, an anteromedial portal is used to drill the femoral tunnel and a separate tibial tunnel.

It will be appreciated by those of skill in the art that the tissue capture anchors 100 and 1000 and inserter tool 400 provide a system for easy attachment of a tendon or tissue to bone. The anchors 100 or 1000 may be inserted into bone with minimal disruption of surrounding tissue. Only an access route having the diameter of the outer tube 704 and the anchor body 200 is required. Furthermore, the anchor can be securely attached to the bone without having to insert additional instrumentation into the site or without performing any cumbersome attachment maneuvers such as knot tying.

Although the invention has been described with reference to embodiments and examples, it should be understood that numerous and various modifications can be made without departing from the spirit of the invention. Accordingly, the invention is limited only by the following claims.

What is claimed is:

1. A method of attaching soft tissue to bone, comprising:
    capturing a soft tissue with an anchor, wherein the anchor comprises a distal capture member and a proximal anchor member comprising a central hole adapted to receive a portion of the distal capture member, wherein the distal capture member comprises a distally facing flat face comprising two holes with separate openings positioned on the distally facing flat face thereof, wherein each separate opening comprises a separate perimeter, and receiving two limbs of a suture loop formed on the distally facing flat face and positioned distally of the distal capture member, and wherein capturing the soft tissue comprises threading the soft tissue through the formed suture loop and tightening the suture loop around the soft tissue to secure the soft tissue to the distal capture member, wherein the distal capture member comprises a proximal portion and a distal portion, wherein the proximal portion of the distal capture member comprises an axial bore, and wherein the two suture limbs extend through the two holes in the distally facing flat face of the distal capture member into the axial bore and exit the axial bore at a proximal end of the distal capture member;
    inserting the proximal anchor member and the distal capture member with captured soft tissue into a bone hole in a bone; and
    moving the distal capture member proximally into the central hole of the proximal anchor member, thereby causing expansion of the proximal anchor member to engage with the bone and fixedly secure the anchor in the bone hole;
    wherein during insertion of the distal capture member, the soft tissue folds around the anchor longitudinally such that the soft tissue runs along one side of the anchor from a proximal end of the anchor to a distal end of the anchor, continues around the distal end of the anchor, and continues along another side of the anchor from the distal end of the anchor to the proximal end of the anchor.

2. The method of claim 1, wherein relatively moving the distal capture member proximally into the proximal anchor member comprises using an insertion tool, wherein the insertion tool comprises a rod configured to extend through a central hole in the proximal anchor member and couple to the distal capture member.

3. The method of claim 1, wherein the proximal anchor member is tapered such that a proximal end of the proximal anchor member includes a larger diameter than a distal end of the proximal anchor member.

4. The method of claim 3, wherein the proximal anchor member further comprises angled protrusions configured to provide greater resistance to removing than to inserting the proximal anchor member in the bone hole.

5. The method of claim 1, further comprising drilling the bone hole into a bicipital groove.

6. The method of claim 1, further comprising drilling the bone hole into a femur.

7. The method of claim 1, further comprising clearing the bone of any soft tissue in the region of the bone hole.

8. The method of claim 1, wherein expansion of the proximal anchor member comprises expansion of a plurality of tines against the soft tissue and bone.

9. The method of claim 1, wherein the soft tissue is secured without the use of knots.

10. The method of claim 1, wherein the method is conducted arthroscopically or in open surgery.

11. The method of claim 1, wherein the soft tissue is secured within the bone by forcing the anchor within the bone after the tissue has been secured to the distal capture member.

12. The method of claim 1, wherein expansion of the proximal anchor member comprises expansion from a diameter of about 9 mm to a diameter of about 15 mm.

13. The method of claim 1, wherein tightening the suture loop secures the soft tissue against the distally facing flat face.

14. The method of claim 1, wherein the proximal portion of the distal capture member is tube shaped and the distal portion of the distal capture member is generally conical shaped and wherein the distal capture member increases in diameter distally.

15. The method of claim 1, wherein the proximal anchor member comprises a central hole in its proximal end through which the two suture limbs extend.

* * * * *